US011684757B2

(12) United States Patent
Chng et al.

(10) Patent No.: US 11,684,757 B2
(45) Date of Patent: Jun. 27, 2023

(54) VALVED CATHETER ASSEMBLIES AND RELATED METHODS

(71) Applicant: B. Braun Melsungen AG, Melsungen (DE)

(72) Inventors: Hang Khiang Chng, Bishan (SG); Wen Jenn Lim, Penang (MY); Khai Tick Sim, Penang (MY); Yueh Shiuan Ghoo, Penang (MY); Hui Kuun Teoh, Penang (MY); Meng Mun Chong, Penang (MY); Zi Lai Lim, Penang (MY); Boon Ping Neoh, Penang (MY); Jarryd Keng Gene Ng, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 388 days.

(21) Appl. No.: 16/323,379

(22) PCT Filed: Aug. 18, 2017

(86) PCT No.: PCT/EP2017/070934
§ 371 (c)(1),
(2) Date: Feb. 5, 2019

(87) PCT Pub. No.: WO2018/033626
PCT Pub. Date: Feb. 22, 2018

(65) Prior Publication Data
US 2021/0113824 A1    Apr. 22, 2021

(30) Foreign Application Priority Data

Aug. 18, 2016 (WO) ................ PCT/EP2016/069619
Aug. 18, 2016 (WO) ................ PCT/EP2016/069643

(51) Int. Cl.
*A61M 25/06* (2006.01)
*A61M 39/06* (2006.01)
(Continued)

(52) U.S. Cl.
CPC ..... *A61M 25/0606* (2013.01); *A61B 5/15003* (2013.01); *A61M 25/0618* (2013.01);
(Continued)

(58) Field of Classification Search
CPC ................ A61M 39/045; A61M 39/26; A61M 39/0693; A61M 2039/062;
(Continued)

(56) References Cited

U.S. PATENT DOCUMENTS 4,387,879 A * 6/1983 Tauschinski ........ A61M 39/045
137/846
4,424,833 A  1/1984 Spector et al.
(Continued)

FOREIGN PATENT DOCUMENTS

CN  101610809 A  12/2009
CN  101808692 A  8/2010
(Continued)

OTHER PUBLICATIONS

International Preliminary Report on Patentability (Chapter 1) on corresponding PCT application (PCT/EP2017/070934) from International Searching Authority (EPO) dated Feb. 28, 2019.
(Continued)

*Primary Examiner* — Scott J Medway
(74) *Attorney, Agent, or Firm* — KOS IP Law LLP

(57) ABSTRACT

Valves are described for intravenous (IV) catheter assemblies for controlling fluidic flow. The valve can prevent blood leakage in multiple access use situations. A thinner area of the valve around a slit is provided. The thicker area of the valve is to provide rigidity to the valve so that it is able to return to a closed configuration when a Luer connector is removed.

45 Claims, 30 Drawing Sheets

(51) Int. Cl.
*A61M 39/02* (2006.01)
*A61B 5/15* (2006.01)

(52) U.S. Cl.
CPC .... *A61M 39/0208* (2013.01); *A61M 39/0247* (2013.01); *A61M 39/06* (2013.01); *A61M 39/0613* (2013.01); *A61M 39/0693* (2013.01); *A61M 25/0693* (2013.01); *A61M 2039/027* (2013.01); *A61M 2039/0258* (2013.01); *A61M 2039/062* (2013.01); *A61M 2039/064* (2013.01); *A61M 2039/0666* (2013.01); *A61M 2207/00* (2013.01)

(58) Field of Classification Search
CPC .... A61M 2039/064; A61M 2039/0633; A61M 2039/0036; A61M 25/0102
See application file for complete search history.

(56) References Cited

U.S. PATENT DOCUMENTS

| | | | |
|---|---|---|---|
| 4,436,519 A * | 3/1984 | O'Neill | A61M 39/0606 604/175 |
| 4,512,766 A * | 4/1985 | Vailancourt | A61M 39/14 251/149.1 |
| 4,673,393 A | 6/1987 | Suzuki et al. | |
| 4,683,916 A * | 8/1987 | Raines | F16K 15/148 137/854 |
| 4,842,591 A * | 6/1989 | Luther | A61M 39/26 285/3 |
| 4,874,377 A * | 10/1989 | Newgard | A61M 39/045 604/167.02 |
| 4,909,798 A * | 3/1990 | Fleischhaker | A61M 39/0606 137/846 |
| 4,917,668 A * | 4/1990 | Haindl | A61M 39/26 604/167.03 |
| 5,053,014 A * | 10/1991 | Van Heugten | A61M 39/26 604/167.03 |
| 5,062,836 A * | 11/1991 | Wendell | A61M 39/045 604/167.04 |
| 5,064,416 A * | 11/1991 | Newgard | A61M 39/045 604/167.03 |
| 5,085,645 A * | 2/1992 | Purdy | A61M 39/26 604/167.03 |
| 5,114,408 A | 5/1992 | Fleischhaker et al. | |
| 5,134,996 A | 8/1992 | Bell | |
| 5,154,703 A | 10/1992 | Bonaldo | |
| 5,188,607 A | 2/1993 | Wu | |
| 5,234,410 A * | 8/1993 | Graham | A61M 39/0606 251/149.1 |
| 5,242,393 A * | 9/1993 | Brimhall | A61M 39/26 604/249 |
| 5,254,098 A | 10/1993 | Ulrich et al. | |
| 5,269,763 A * | 12/1993 | Boehmer | A61M 39/0606 251/149.1 |
| 5,269,768 A | 12/1993 | Cheung | |
| 5,300,043 A | 4/1994 | Devlin et al. | |
| 5,330,435 A | 7/1994 | Vaillancourt | |
| 5,342,315 A * | 8/1994 | Rowe | A61B 17/3462 604/167.06 |
| 5,342,316 A * | 8/1994 | Wallace | A61M 39/045 137/845 |
| 5,349,950 A | 9/1994 | Ulrich et al. | |
| 5,350,363 A * | 9/1994 | Goode | A61M 39/0606 604/167.04 |
| 5,409,461 A | 4/1995 | Steinman | |
| 5,419,766 A | 5/1995 | Chang et al. | |
| 5,419,769 A | 5/1995 | Devlin et al. | |
| 5,429,616 A | 7/1995 | Schaffer | |
| 5,456,284 A * | 10/1995 | Ryan | A61B 1/00137 137/522 |
| 5,458,640 A * | 10/1995 | Gerrone | A61B 17/3417 604/158 |
| 5,460,613 A | 10/1995 | Ulrich et al. | |
| 5,476,451 A | 12/1995 | Ensminger et al. | |
| 5,480,385 A | 1/1996 | Thorne et al. | |
| 5,490,503 A | 2/1996 | Hollister | |
| 5,501,674 A | 3/1996 | Trombley, III et al. | |
| 5,514,116 A * | 5/1996 | Vaillancourt | A61M 39/26 604/537 |
| 5,531,720 A | 7/1996 | Atkins | |
| 5,533,708 A * | 7/1996 | Atkinson | A61M 39/045 251/149.1 |
| 5,542,927 A | 8/1996 | Thorne et al. | |
| 5,542,933 A | 8/1996 | Marks | |
| 5,607,407 A | 3/1997 | Tolkoff et al. | |
| 5,611,782 A | 3/1997 | Haedt | |
| 5,613,663 A | 3/1997 | Schmidt et al. | |
| 5,628,732 A * | 5/1997 | Antoon, Jr. | A61B 17/3462 604/167.06 |
| 5,685,866 A * | 11/1997 | Lopez | A61M 5/14 604/249 |
| 5,688,253 A | 11/1997 | Paradis | |
| 5,704,914 A | 1/1998 | Stocking et al. | |
| 5,727,770 A * | 3/1998 | Dennis | A61B 17/3462 251/149.1 |
| 5,749,857 A | 5/1998 | Cuppy | |
| 5,755,709 A | 5/1998 | Cuppy | |
| 5,759,179 A | 6/1998 | Balbierz | |
| 5,792,104 A | 8/1998 | Speckman et al. | |
| 5,797,880 A | 8/1998 | Erskine | |
| 5,800,395 A | 9/1998 | Botich et al. | |
| 5,810,835 A | 9/1998 | Ryan et al. | |
| 5,817,069 A | 10/1998 | Arnett | |
| 5,830,228 A | 11/1998 | Knapp et al. | |
| 5,833,662 A | 11/1998 | Stevens | |
| 5,843,046 A | 12/1998 | Motisi et al. | |
| 5,853,394 A | 12/1998 | Tolkoff et al. | |
| 5,858,002 A | 1/1999 | Jesch | |
| 5,865,806 A | 2/1999 | Howell | |
| 5,911,706 A | 6/1999 | Estabrook et al. | |
| 5,911,710 A | 6/1999 | Barry et al. | |
| 5,935,110 A | 8/1999 | Brimhall | |
| 5,954,698 A | 9/1999 | Pike | |
| 5,968,068 A * | 10/1999 | Dehdashtian | A61F 2/958 604/164.08 |
| 5,976,110 A | 11/1999 | Greengrass et al. | |
| 6,007,519 A | 12/1999 | Rosselli | |
| 6,013,058 A | 1/2000 | Prosl et al. | |
| 6,024,727 A | 2/2000 | Thorne et al. | |
| 6,024,729 A * | 2/2000 | Dehdashtian | A61M 39/0606 604/167.04 |
| 6,056,760 A | 5/2000 | Koike et al. | |
| 6,074,371 A | 6/2000 | Fischell | |
| 6,113,572 A | 9/2000 | Gailey et al. | |
| 6,132,402 A | 10/2000 | Tessmann et al. | |
| 6,171,287 B1 * | 1/2001 | Lynn | A61M 39/02 251/149 |
| 6,213,978 B1 | 4/2001 | Voyten | |
| 6,217,554 B1 | 4/2001 | Green | |
| 6,217,556 B1 | 4/2001 | Ellingson et al. | |
| 6,258,065 B1 * | 7/2001 | Dennis | A61B 17/3462 604/167.01 |
| 6,299,602 B1 | 10/2001 | Miller et al. | |
| 6,352,520 B1 | 3/2002 | Miyazaki | |
| 6,371,963 B1 | 4/2002 | Nishtala et al. | |
| 6,379,337 B1 | 4/2002 | Mohommad | |
| 6,482,186 B1 | 11/2002 | Douglas et al. | |
| 6,485,473 B1 | 11/2002 | Lynn | |
| 6,506,181 B2 | 1/2003 | Meng et al. | |
| 6,533,759 B1 | 3/2003 | Watson et al. | |
| 6,544,235 B2 | 4/2003 | Motisi et al. | |
| 6,610,045 B2 | 8/2003 | Chavez et al. | |
| 6,616,630 B1 | 9/2003 | Woehr et al. | |
| 6,620,136 B1 | 9/2003 | Pressley, Sr. et al. | |
| 6,699,221 B2 | 3/2004 | Vaillancourt | |
| 6,719,726 B2 | 4/2004 | Meng et al. | |
| 6,740,063 B2 | 5/2004 | Lynn | |
| 6,746,420 B1 | 6/2004 | Prestidge et al. | |
| 6,764,468 B1 | 7/2004 | East | |

(56) References Cited

U.S. PATENT DOCUMENTS

| | | | |
|---|---|---|---|
| 6,860,869 B2 * | 3/2005 | Dennis | A61B 17/3462 604/167.03 |
| 6,921,386 B2 | 7/2005 | Shue et al. | |
| 6,921,391 B1 | 7/2005 | Barker et al. | |
| 6,981,969 B2 | 1/2006 | Chavez et al. | |
| 7,008,404 B2 | 3/2006 | Nakajima | |
| 7,048,729 B2 | 5/2006 | Meglin et al. | |
| 7,052,507 B2 | 5/2006 | Wakuda et al. | |
| 7,120,487 B2 | 10/2006 | Nelson | |
| 7,125,396 B2 | 10/2006 | Leinsing et al. | |
| 7,156,827 B2 | 1/2007 | McNary et al. | |
| 7,163,525 B2 * | 1/2007 | Franer | A61B 17/3462 604/167.03 |
| 7,214,215 B2 | 5/2007 | Heinzerling et al. | |
| 7,270,649 B2 | 9/2007 | Fitzgerald | |
| 7,311,708 B2 | 12/2007 | McClurken | |
| 7,347,839 B2 | 3/2008 | Hiejima | |
| 7,470,254 B2 * | 12/2008 | Basta | A61M 25/01 604/167.04 |
| 7,537,595 B2 | 5/2009 | McClurken | |
| 7,625,346 B2 | 12/2009 | Grigoryants et al. | |
| 7,632,243 B2 | 12/2009 | Bialecki et al. | |
| 7,632,262 B2 | 12/2009 | Bates | |
| 7,635,357 B2 * | 12/2009 | Mayer | A61M 39/045 604/249 |
| 7,641,669 B2 | 1/2010 | Roychowdhury et al. | |
| 7,666,166 B1 | 2/2010 | Emmert et al. | |
| 7,670,317 B2 | 3/2010 | Cindrich et al. | |
| 7,670,322 B2 * | 3/2010 | Fangrow, Jr. | A61M 39/24 604/247 |
| 7,691,093 B2 | 4/2010 | Brimhall | |
| 7,695,458 B2 | 4/2010 | Belley et al. | |
| 7,713,257 B2 | 5/2010 | Brimhall et al. | |
| 7,736,337 B2 | 6/2010 | Diep et al. | |
| 7,736,339 B2 | 6/2010 | Woehr et al. | |
| 7,758,514 B2 | 7/2010 | Grigoryants et al. | |
| 7,789,861 B2 * | 9/2010 | Franer | A61B 17/3462 604/167.06 |
| 7,806,869 B2 | 10/2010 | Nilsson et al. | |
| 7,901,379 B2 * | 3/2011 | Argentine | A61M 39/0606 604/167.06 |
| 7,914,494 B2 | 3/2011 | Hiejima | |
| 7,914,496 B2 * | 3/2011 | Brockmeier | A61B 17/3498 604/167.06 |
| 7,955,346 B2 | 6/2011 | Mauch et al. | |
| 8,002,750 B2 * | 8/2011 | Smith | A61B 17/3462 604/167.03 |
| 8,006,953 B2 | 8/2011 | Bennett | |
| 8,016,791 B2 * | 9/2011 | Sugiki | F16K 15/1825 604/167.04 |
| 8,029,472 B2 | 10/2011 | Leinsing et al. | |
| 8,042,689 B2 | 10/2011 | Frojd et al. | |
| 8,048,039 B2 | 11/2011 | Carlyon et al. | |
| 8,056,756 B2 | 11/2011 | Okiyama | |
| 8,066,670 B2 * | 11/2011 | Cluff | A61M 25/00 604/126 |
| 8,066,675 B2 | 11/2011 | Cindrich et al. | |
| 8,123,727 B2 | 2/2012 | Luther et al. | |
| 8,147,413 B2 | 4/2012 | Abraham | |
| 8,147,455 B2 | 4/2012 | Butts et al. | |
| 8,152,755 B1 | 4/2012 | Wach et al. | |
| 8,172,757 B2 | 5/2012 | Jaffe et al. | |
| 8,202,253 B1 | 6/2012 | Wexler | |
| 8,206,357 B2 * | 6/2012 | Bettuchi | A61B 17/3421 604/167.01 |
| 8,206,375 B2 | 6/2012 | Snow | |
| 8,257,313 B2 | 9/2012 | McKinnon et al. | |
| 8,257,339 B1 | 9/2012 | Rosado | |
| 8,262,623 B2 * | 9/2012 | Nijland | A61M 39/06 604/167.03 |
| 8,286,657 B2 | 10/2012 | Belley et al. | |
| 8,308,655 B2 | 11/2012 | Grigoryants et al. | |
| 8,308,691 B2 | 11/2012 | Woehr et al. | |
| 8,323,249 B2 | 12/2012 | White et al. | |
| 8,328,762 B2 | 12/2012 | Woehr et al. | |
| 8,333,735 B2 | 12/2012 | Woehr et al. | |
| 8,337,463 B2 | 12/2012 | Woehr et al. | |
| 8,348,844 B2 | 1/2013 | Kunjan et al. | |
| 8,361,038 B2 * | 1/2013 | McKinnon | A61M 25/0606 604/244 |
| 8,366,684 B2 | 2/2013 | Harding | |
| 8,388,583 B2 | 3/2013 | Stout et al. | |
| 8,419,688 B2 | 4/2013 | Woehr et al. | |
| 8,454,579 B2 * | 6/2013 | Fangrow, Jr. | A61M 39/1011 604/539 |
| 8,460,247 B2 | 6/2013 | Woehr et al. | |
| 8,465,461 B2 | 6/2013 | Wu et al. | |
| 8,469,928 B2 | 6/2013 | Stout et al. | |
| 8,470,025 B2 | 6/2013 | Lenihan et al. | |
| 8,506,533 B2 | 8/2013 | Carlyon et al. | |
| 8,506,534 B2 | 8/2013 | Luther et al. | |
| 8,518,013 B2 | 8/2013 | Kurrus et al. | |
| 8,535,271 B2 | 9/2013 | Fuchs et al. | |
| 8,540,728 B2 | 9/2013 | Woehr et al. | |
| 8,562,520 B2 * | 10/2013 | Rockrohr | A61B 17/3462 600/208 |
| 8,585,651 B2 | 11/2013 | Asai | |
| 8,591,468 B2 | 11/2013 | Woehr et al. | |
| 8,597,249 B2 | 12/2013 | Woehr et al. | |
| 8,597,252 B2 | 12/2013 | Burkholz et al. | |
| 8,608,727 B2 | 12/2013 | Michels et al. | |
| 8,608,728 B2 | 12/2013 | Michels et al. | |
| 8,622,972 B2 | 1/2014 | Nystrom et al. | |
| 8,628,056 B2 * | 1/2014 | LaBean | B65D 51/002 251/149.1 |
| 8,636,695 B2 | 1/2014 | Cluff et al. | |
| 8,641,675 B2 | 2/2014 | Stout et al. | |
| 8,641,676 B2 | 2/2014 | Butts et al. | |
| 8,647,301 B2 | 2/2014 | Bialecki et al. | |
| 8,652,104 B2 | 2/2014 | Goral et al. | |
| 8,663,169 B2 | 3/2014 | Emmert et al. | |
| 8,668,674 B2 | 3/2014 | White et al. | |
| 8,679,063 B2 | 3/2014 | Stout et al. | |
| 8,690,815 B2 | 4/2014 | Porter et al. | |
| 8,690,833 B2 | 4/2014 | Belson | |
| 8,715,242 B2 | 5/2014 | Helm, Jr. | |
| 8,728,030 B2 | 5/2014 | Woehr | |
| 8,740,850 B2 | 6/2014 | Leinsing et al. | |
| 8,771,230 B2 | 7/2014 | White et al. | |
| 8,790,310 B2 | 7/2014 | White et al. | |
| 8,831,707 B2 | 9/2014 | Tekulve et al. | |
| 8,864,715 B2 | 10/2014 | Cluff et al. | |
| 8,882,742 B2 | 11/2014 | Dikeman et al. | |
| 8,926,494 B1 | 1/2015 | Cook et al. | |
| 8,932,257 B2 | 1/2015 | Woehr | |
| 8,932,258 B2 | 1/2015 | Blanchard et al. | |
| 8,932,259 B2 | 1/2015 | Stout et al. | |
| 8,939,938 B2 * | 1/2015 | Funamura | A61M 25/0618 604/164.08 |
| 8,968,252 B2 | 3/2015 | White et al. | |
| 8,979,802 B2 | 3/2015 | Woehr | |
| 8,998,852 B2 | 4/2015 | Blanchard et al. | |
| 9,011,382 B2 | 4/2015 | Nilsson et al. | |
| 9,028,393 B2 | 5/2015 | Farnan | |
| 9,028,425 B2 * | 5/2015 | Burkholz | A61B 5/15 600/577 |
| 9,089,671 B2 * | 7/2015 | Stout | A61M 39/00 |
| 9,095,679 B2 | 8/2015 | Nishimura et al. | |
| 9,108,021 B2 | 8/2015 | Hyer et al. | |
| 9,114,231 B2 * | 8/2015 | Woehr | A61M 39/26 |
| 9,114,241 B2 | 8/2015 | Stout et al. | |
| 9,149,625 B2 | 10/2015 | Woehr et al. | |
| 9,149,626 B2 | 10/2015 | Woehr et al. | |
| 9,155,863 B2 | 10/2015 | Isaacson et al. | |
| 9,155,864 B2 | 10/2015 | Stout et al. | |
| 9,180,275 B2 | 11/2015 | Helm | |
| 9,186,455 B2 | 11/2015 | Moyer | |
| 9,220,833 B2 | 12/2015 | Robert et al. | |
| 9,227,038 B2 | 1/2016 | Woehr | |
| 9,227,047 B2 | 1/2016 | Khalaj | |
| RE45,896 E * | 2/2016 | Stout | A61M 25/0606 |
| 9,272,088 B2 | 3/2016 | Bornhoft | |
| 9,314,201 B2 | 4/2016 | Burkholz et al. | |

(56) References Cited

U.S. PATENT DOCUMENTS

| | | | |
|---|---|---|---|
| 9,320,870 B2 | 4/2016 | Woehr | |
| 9,327,095 B2 | 5/2016 | Ma | |
| 9,352,119 B2* | 5/2016 | Burkholz | A61M 39/0693 |
| 9,370,641 B2 | 6/2016 | Woehr et al. | |
| 9,381,320 B2 | 7/2016 | Vincent et al. | |
| 9,381,324 B2 | 7/2016 | Fuchs et al. | |
| 9,399,116 B2 | 7/2016 | Goral et al. | |
| 9,427,549 B2 | 8/2016 | Wooehr et al. | |
| 9,522,266 B2* | 12/2016 | Sutton | A61M 25/09041 |
| 9,545,632 B2* | 1/2017 | Lentz | B65D 51/002 |
| 9,579,486 B2* | 2/2017 | Burkholz | A61M 25/0097 |
| 9,592,366 B2 | 3/2017 | White et al. | |
| 9,623,210 B2 | 4/2017 | Woehr | |
| 9,737,252 B2 | 8/2017 | Teoh et al. | |
| 9,750,920 B2 | 9/2017 | Vincent et al. | |
| 9,764,085 B2 | 9/2017 | Teoh | |
| 9,844,648 B2 | 12/2017 | Nakajima et al. | |
| 9,919,136 B2 | 3/2018 | Lim et al. | |
| 9,962,525 B2 | 5/2018 | Woehr | |
| 10,004,891 B2 | 6/2018 | Woehr | |
| 10,080,869 B2 | 9/2018 | Woehr et al. | |
| 10,166,370 B2 | 1/2019 | Woehr et al. | |
| 10,173,002 B2 | 1/2019 | Tan et al. | |
| 10,207,081 B2 | 2/2019 | Fuchs et al. | |
| 10,286,185 B2 | 5/2019 | Tanabe et al. | |
| 10,376,686 B2* | 8/2019 | Burkholz | A61M 39/165 |
| 10,449,331 B2 | 10/2019 | Lim et al. | |
| 10,456,572 B2 | 10/2019 | Woehr | |
| 10,463,395 B2* | 11/2019 | Reid | A61B 17/3462 |
| 10,463,839 B2 | 11/2019 | Woehr | |
| 10,493,262 B2 | 12/2019 | Tran et al. | |
| 10,500,376 B2 | 12/2019 | Isaacson et al. | |
| 10,543,343 B2 | 1/2020 | Woehr et al. | |
| 10,549,072 B2 | 2/2020 | Burkolz et al. | |
| 10,646,253 B2* | 5/2020 | Blanc | A61B 17/3462 |
| 2001/0053895 A1* | 12/2001 | Vaillancourt | A61M 25/0606 604/243 |
| 2002/0010425 A1* | 1/2002 | Guo | A61M 39/06 604/167.04 |
| 2002/0128604 A1* | 9/2002 | Nakajima | A61M 39/0693 604/164.01 |
| 2004/0210194 A1 | 10/2004 | Bonnette et al. | |
| 2005/0256500 A1* | 11/2005 | Fujii | A61M 39/045 604/523 |
| 2006/0118749 A1* | 6/2006 | Ryan | F16K 51/00 251/149.7 |
| 2006/0155245 A1* | 7/2006 | Woehr | A61M 39/0693 604/164.08 |
| 2007/0083162 A1 | 4/2007 | O'Reagan et al. | |
| 2007/0225647 A1 | 9/2007 | Luther et al. | |
| 2007/0233007 A1* | 10/2007 | Adams | A61M 25/0097 604/168.01 |
| 2008/0058720 A1* | 3/2008 | Spohn | A61M 5/007 604/140 |
| 2008/0108944 A1* | 5/2008 | Woehr | A61B 5/150992 604/164.08 |
| 2008/0108976 A1 | 5/2008 | Johnson et al. | |
| 2008/0208132 A1 | 8/2008 | Funamura et al. | |
| 2008/0300455 A1 | 12/2008 | Smith | |
| 2009/0221975 A1 | 9/2009 | Rodd | |
| 2010/0179480 A1* | 7/2010 | Sugiki | A61M 39/0693 604/167.04 |
| 2010/0185153 A1 | 7/2010 | Sugiki et al. | |
| 2010/0204648 A1* | 8/2010 | Stout | A61M 25/0606 604/122 |
| 2010/0280456 A1 | 11/2010 | Nijland et al. | |
| 2011/0046570 A1 | 2/2011 | Stout et al. | |
| 2011/0054406 A1 | 3/2011 | McKinnon | |
| 2011/0282286 A1 | 11/2011 | Argentine | |
| 2011/0301553 A1 | 12/2011 | Goral et al. | |
| 2011/0319825 A1* | 12/2011 | Goral | A61M 25/0102 604/164.01 |
| 2011/0319838 A1 | 12/2011 | Goral et al. | |
| 2012/0016266 A1* | 1/2012 | Burkholz | A61B 5/150213 600/581 |
| 2012/0089101 A1 | 4/2012 | Carlyon et al. | |
| 2012/0259293 A1 | 10/2012 | Bialecki et al. | |
| 2012/0330238 A1 | 12/2012 | Robert et al. | |
| 2013/0006223 A1 | 1/2013 | Michels et al. | |
| 2013/0165868 A1* | 6/2013 | Isaacson | A61M 39/26 604/256 |
| 2013/0204226 A1 | 8/2013 | Keyser | |
| 2013/0304026 A1 | 11/2013 | Luther et al. | |
| 2014/0052065 A1 | 2/2014 | Woehr et al. | |
| 2014/0107619 A1 | 4/2014 | Butts et al. | |
| 2014/0135702 A1* | 5/2014 | Woehr | A61M 39/221 604/164.08 |
| 2014/0207083 A1 | 7/2014 | Pessin | |
| 2014/0228775 A1* | 8/2014 | Burkholz | A61M 39/0693 604/244 |
| 2014/0276434 A1* | 9/2014 | Woehr | A61M 39/0693 604/164.08 |
| 2014/0276453 A1 | 9/2014 | Woehr | |
| 2014/0276462 A1* | 9/2014 | Vincent | A61M 39/0606 604/256 |
| 2014/0288500 A1 | 9/2014 | Leinsing et al. | |
| 2015/0038909 A1 | 2/2015 | Christensen et al. | |
| 2015/0038910 A1 | 2/2015 | Harding et al. | |
| 2015/0088095 A1 | 3/2015 | Luther et al. | |
| 2015/0151085 A1 | 6/2015 | Tan et al. | |
| 2015/0151088 A1 | 6/2015 | Lim et al. | |
| 2015/0190570 A1 | 7/2015 | Teoh | |
| 2015/0335858 A1 | 11/2015 | Woehr et al. | |
| 2015/0335864 A1 | 11/2015 | Knutsson | |
| 2016/0008580 A1 | 1/2016 | Woehr et al. | |
| 2016/0114136 A1 | 4/2016 | Woehr | |
| 2016/0114137 A1 | 4/2016 | Woehr et al. | |
| 2016/0175563 A1 | 6/2016 | Woehr et al. | |
| 2016/0296724 A1 | 10/2016 | Goral et al. | |
| 2016/0331936 A1 | 11/2016 | Lim et al. | |
| 2017/0035992 A1 | 2/2017 | Harding et al. | |
| 2017/0173304 A1 | 6/2017 | Teoh | |
| 2017/0326341 A1* | 11/2017 | Liska | A61M 25/0606 |
| 2018/0093077 A1 | 4/2018 | Harding et al. | |
| 2018/0214682 A1* | 8/2018 | Woehr | A61M 39/0693 |
| 2018/0361119 A1 | 12/2018 | Goral et al. | |
| 2018/0361120 A1 | 12/2018 | Goral et al. | |
| 2019/0038870 A1 | 2/2019 | Isaacson et al. | |
| 2019/0076625 A1 | 3/2019 | White et al. | |
| 2019/0160264 A1 | 5/2019 | Isaacson | |
| 2022/0001145 A1 | 1/2022 | Neoh | |

FOREIGN PATENT DOCUMENTS

| | | |
|---|---|---|
| CN | 203724591 U | 7/2014 |
| CN | 203763665 U | 8/2014 |
| CN | 104039384 A | 9/2014 |
| CN | 104043167 A | 9/2014 |
| CN | 104415446 A | 3/2015 |
| CN | 105407959 A | 3/2016 |
| EP | 0875262 A2 | 11/1998 |
| EP | 1911485 A1 | 4/2008 |
| EP | 2213328 A1 | 8/2010 |
| EP | 3 097 939 A1 | 11/2016 |
| EP | 3337549 B1 | 6/2019 |
| FR | 2829396 A1 | 3/2003 |
| JP | H05-028348 U | 4/1993 |
| JP | H06-304250 A | 11/1994 |
| JP | H7-136285 A | 5/1995 |
| JP | H11-004894 A | 1/1999 |
| JP | H11-299898 A | 11/1999 |
| JP | 2005-531377 A | 10/2005 |
| JP | 2010-508905 A1 | 3/2010 |
| JP | 2012-525877 A | 10/2012 |
| JP | 2013-533023 A | 8/2013 |
| JP | 2014-528807 A | 10/2014 |
| JP | 2016-509916 A | 4/2016 |
| RU | 2009120995 A | 12/2010 |
| RU | 2 477 639 C2 | 3/2013 |
| WO | WO 2008/052790 A2 | 5/2008 |
| WO | WO 2010/093791 A1 | 8/2010 |

(56) References Cited

FOREIGN PATENT DOCUMENTS

| | | |
|---|---|---|
| WO | WO 2010/127846 A1 | 11/2010 |
| WO | WO 2009/041522 A1 | 1/2011 |
| WO | WO 2009/041523 A1 | 1/2011 |
| WO | WO 2013/052668 A1 | 4/2013 |
| WO | WO 2014/140265 A1 | 9/2014 |
| WO | WO 2015/104336 A1 | 7/2015 |
| WO | WO 2015/161294 A1 | 10/2015 |
| WO | WO 2018/033626 A1 | 2/2018 |
| WO | WO 2018/077748 A1 | 5/2018 |

OTHER PUBLICATIONS

Extended European Search Report from European Patent Office on related EP application (EP 20172492.9) dated Nov. 5, 2020.
Office Action including Search Reporton corresponding foreign application (CN Application No. 201680048610.6) from the National Intellectual Property Administration, P.R. China dated Mar. 27, 2020.
Office Action including Search Reporton corresponding foreign application (CN Application No. 201680048615.9) from the National Intellectual Property Administration, P.R. China dated Mar. 30, 2020.
Examination Report on corresponding foreign application (AU Application No. 2016309744) from the IP Australia dated May 6, 2020.
Preliminary Office Action on corresponding foreign application (BR Application No. 11 2018 002976-9) from the Brazilian Intellectual Property Office dated May 6, 2020.
Extended European Search Report from the European Patent Office on related EP application (EP19177030.4) dated Jun. 24, 2019.
Office Action on related foreign application (MX Application No. MX/a/2018/001987) from the Mexican Patent Office dated Jul. 23, 2020.
Office Action on related foreign application (JP Application No. 2018-508170) from the Japanese Patent Office dated Jun. 23, 2020.
Office Action on related foreign application (JP Application No. 2018-508169) from the Japanese Patent Office dated Aug. 4, 2020.
Office Action on related foreign application (AU Application No. 2016309744) from the Australian Patent Office dated Aug. 31, 2020.
Office Action on related foreign application (CN Application No. 201310650219.1) from the Chinese Intellectual Property Office dated Feb. 13, 2018.
Office Action on related foreign application (CN Application No. 201310650219.1) from the Chinese Intellectual Property Office dated Oct. 24, 2018.
Office Action on related foreign application (JP Application No. 2015-562191) from the Japanese Patent Office dated Apr. 25, 2017.
Office Action on related foreign application (JP Application No. 2015-562191) from the Japanese Patent Office dated Oct. 17, 2017.
International Preliminary Reporton Patentability on corresponding PCT application (PCT/EP2014/055089) from International Searching Authority (EPO) dated Apr. 10, 2015.
International Search Report and Written Opinion on corresponding PCT application (PCT/EP2019/085732) from International Searching Authority (EPO) dated Apr. 28, 2020.
Supplementary Examination Reporton related foreign application (SG Application No. 11201506983W) from the Singaporean Intellectual Property Office dated Jan. 29, 2016.
Office Action on corresponding foreign application (JP Application No. 2018-508169) from the Japanese Patent Office dated Oct. 1, 2019.
Decision to Grant on corresponding foreign application (RU Application No. 2018109391/14) from the Russian Patent Office dated Oct. 14, 2019.
Office Action on related foreign application (CN Application No. 201780064583.6) from the National Intellectual Property Administration, P.R. China dated Jan. 27, 2021.
Office Action on related foreign application (CN Application No. 201680048610.6) from the National Intellectual Property Administration, P.R. China dated Feb. 20, 2021.
Office Action on related foreign application (JP Application No. 2018-508170) from the Japan Patent Office dated Mar. 2, 2021.
Office Action on related foreign application (MX Application No. MX/a/2018/001987) from the Mexican Institute of Industrial Property (IMPI) dated Dec. 8, 2020.
International Search Report and Written Opinion on corresponding PCT application (PCT/EP2017/070934) from International Searching Authority (EP) dated Oct. 25, 2017.
International Search Report and Written Opinion on related PCT application (PCT/EP2016/069619) from International Searching Authority (EP) dated Dec. 8, 2016.
International Preliminary Report on Patentability (Chapter I) on related PCT Application (PCT/EP2016/069619) from the International Searching Authority (EP) dated Mar. 1, 2018.
International Search Report and Written Opinion on related PCT application (PCT/EP2016/069643) from International Searching Authority (EP) dated Nov. 16, 2016.
International Preliminary Report on Patentability (Chapter I) on related PCT Application (PCT/EP2016/069643) from the International Searching Authority (EP) dated Mar. 1, 2018.
International Search Report & Written Opinion on related PCT application (PCT/EP2014/055089) from International Searching Authority (EPO) dated Jul. 17, 2014.
International Preliminary Report on Patentability (Chapter I) on related PCT Application (PCT/EP2014/055089) from the International Searching Authority (EP) dated Apr. 10, 2015.
Supplementary Examination Reporton related foreign application (SG Application No. 11201506983W) from the Intellectual Property Office of Singapore dated Jan. 29, 2016.
Non-Final Office Action on related US application (U.S. Appl. No. 14/012,568) dated Aug. 8, 2014.
Final Office Action on related US application (U.S. Appl. No. 14/012,568) dated Dec. 2, 2014.
Non-Final Office Action on related US application (U.S. Appl. No. 14/818,687) dated Feb. 10, 2016.
Decision of Rejection on related foreign application (CN Application No. 201680048615.9) from the National Intellectual Property Administration, P.R. China dated Sep. 3, 2021.
Notice of Grant on related foreign application (CN Application No. 201780064583.6) from the National Intellectual Property Administration, P.R. China dated Sep. 10, 2021.
First Examination Report on related foreign application (IN Application No. 201917005065) from Intellectual Property India dated Aug. 19, 2021.
Non-Final Office Action on related US application (U.S. Appl. No. 16/716,890) dated Jul. 21, 2021.
First Examination Report on related foreign application (IN Application No. 201817000337) from the Indian Patent Office dated May 18, 2021.
Office Action on related foreign application (JP Application No. 2019-508949) from the Japan Patent Office dated May 11, 2021.
Substantive Examination Adverse Report on related foreign application (MY Application No. PI 2018700453) from the Malaysian Patent Office dated May 12, 2021.
Preliminary Office Action on related foreign application (BR Application No. 12 2019 017170-0) from the Brazilian Patent Office dated Apr. 7, 2021.
Office Action on related foreign application (CN Application No. 201680048615.9) from the National Intellectual Property Administration, P.R. China dated Mar. 9, 2021.
Examination Report on related foreign application (AU Application No. 2017312323) from IP Australia dated Sep. 30, 2021.
Preliminary Office Action on corresponding foreign application (BR Application No. BR112019003083-2) from Brazilian Patent and Trademark Office dated Dec. 10, 2021.
Notice of Opposition on corresponding foreign application (EP Application/Patent No. EP19177030.4/3552652) from European Patent Office dated Jan. 20, 2022.
Non-Final Office Action on related US application (U.S. Appl. No. 16/716,890) dated Apr. 12, 2022.

(56) References Cited

OTHER PUBLICATIONS

Office Action on related foreign application (KR Application No. 10-2019-7007579) from the Korean Intellectual Property Office dated Jun. 21, 2022.
Substantive Examination Clear Report on related foreign application (MY Application No. PI 2018700453) from the Intellectual Property Corporation of Malaysia dated Oct. 25, 2022.
Final Office Action on related US application (U.S. Appl. No. 16/716,890) dated Oct. 24, 2022.
Office Action on related foreign application (CN Application No. 201911294423.8) from the National Intellectual Property Administration, P.R. China dated Dec. 22, 2022.
Office Action on related foreign application (IN Application No. 202117030932) from Intellectual Property India dated Feb. 17, 2023.
Office Action on related US application (U.S. Appl. No. 16/716,890) dated Feb. 28, 2023.

* cited by examiner

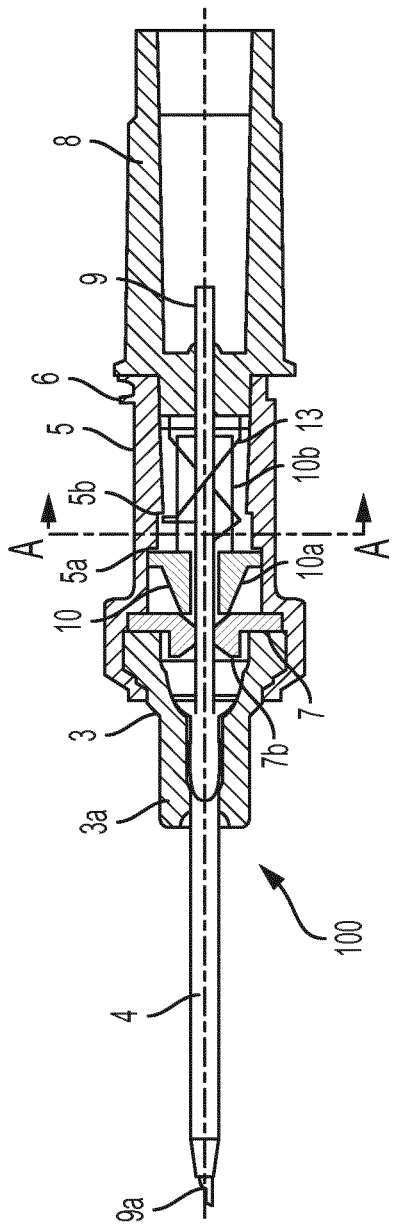

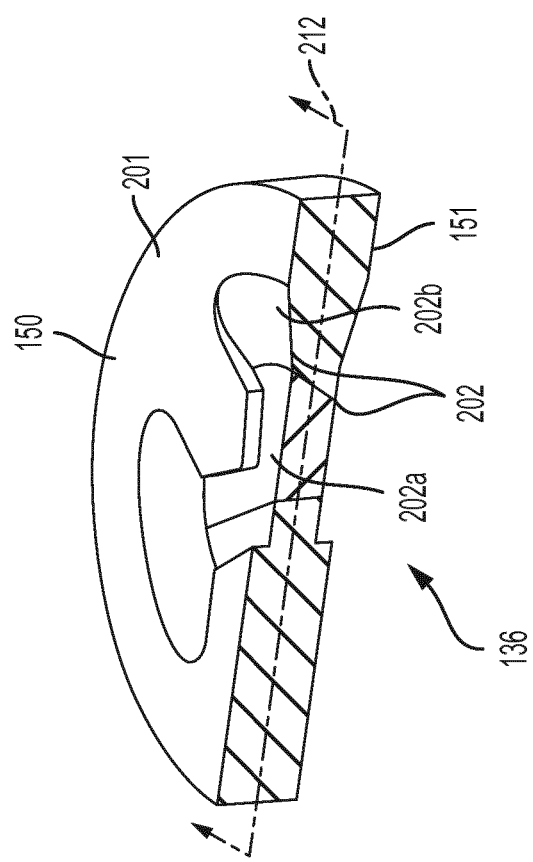
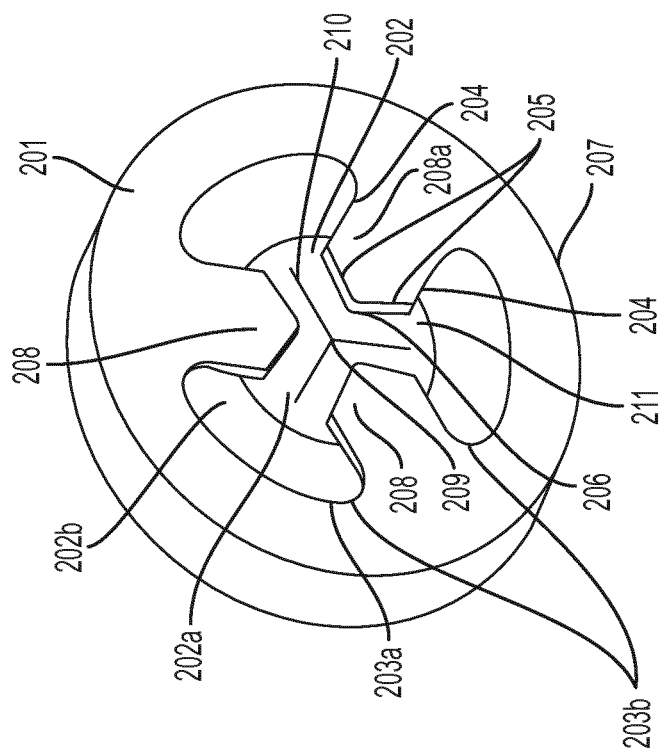
FIG. 2B
FIG. 2A

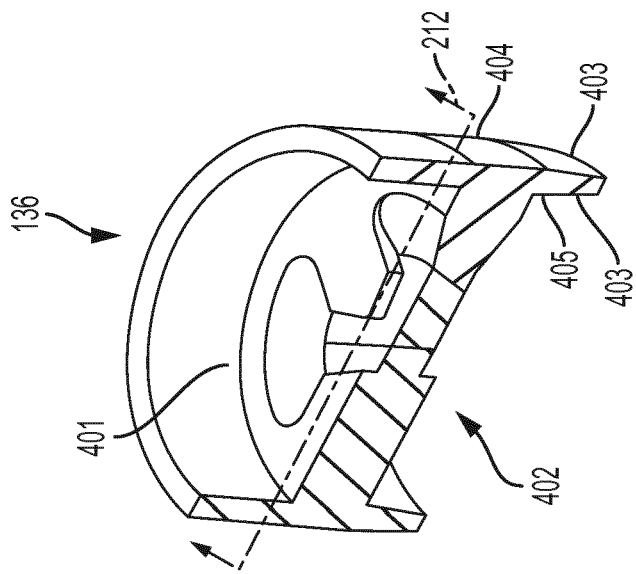
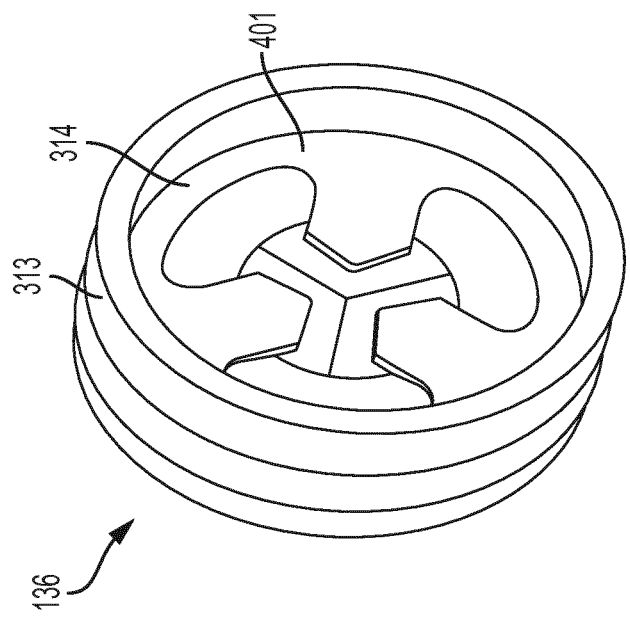
FIG. 4B
FIG. 4A

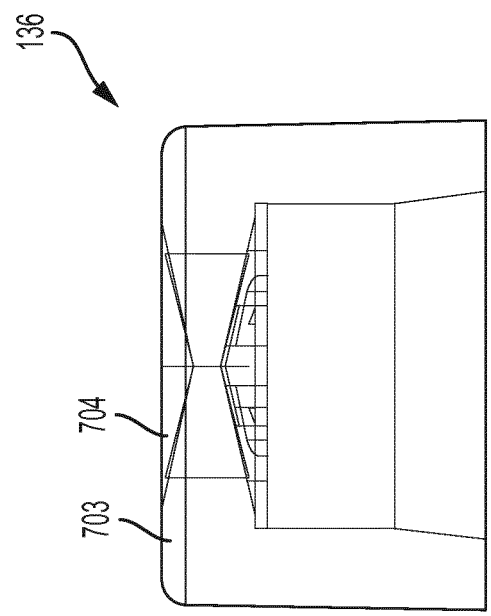
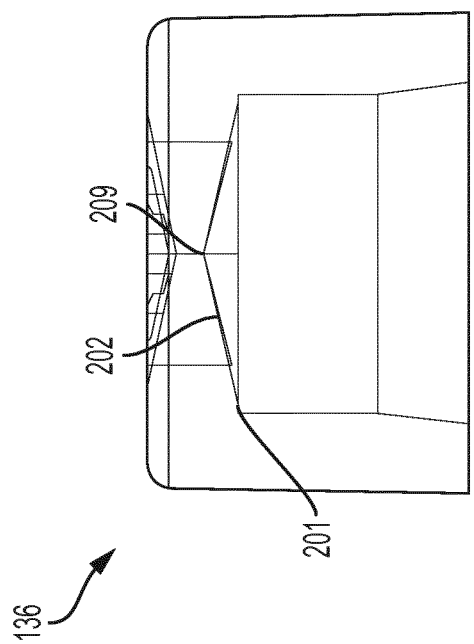
FIG. 8A
FIG. 8B

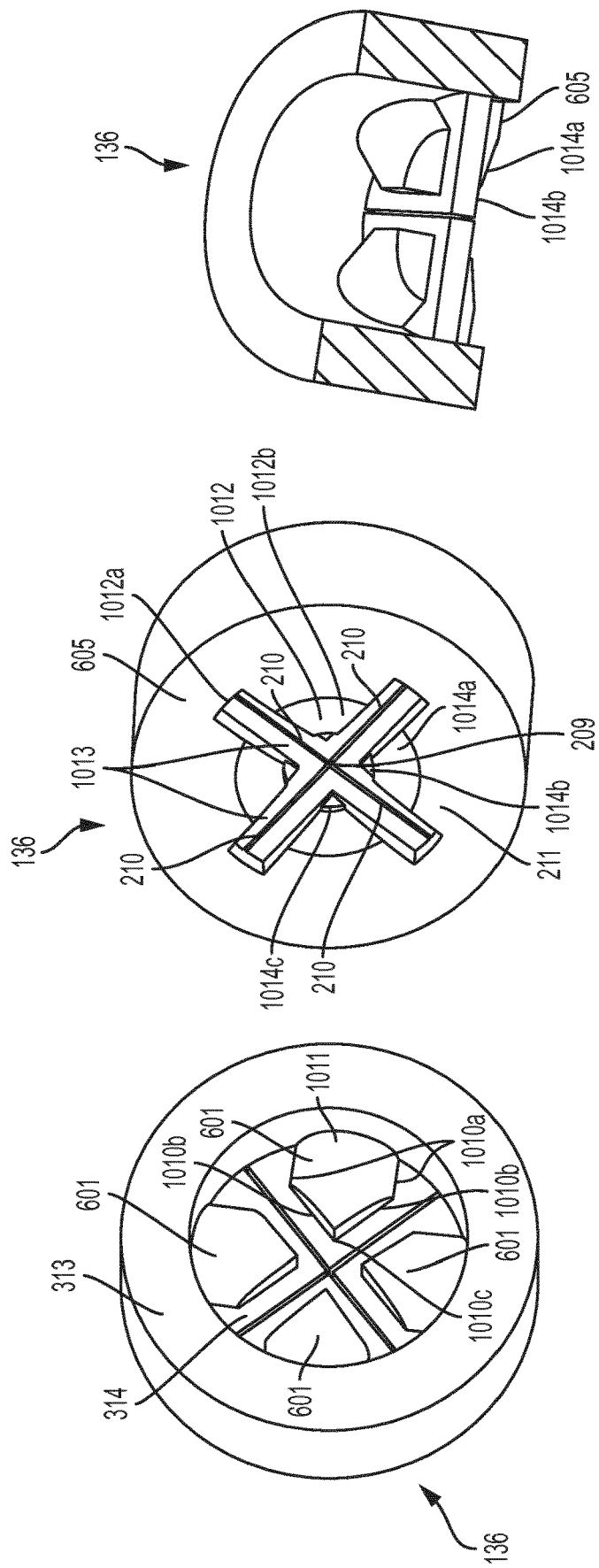

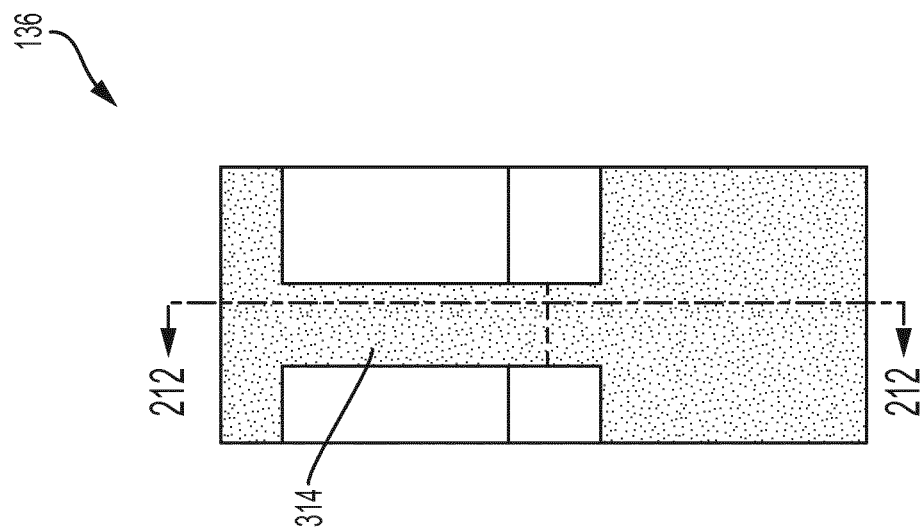

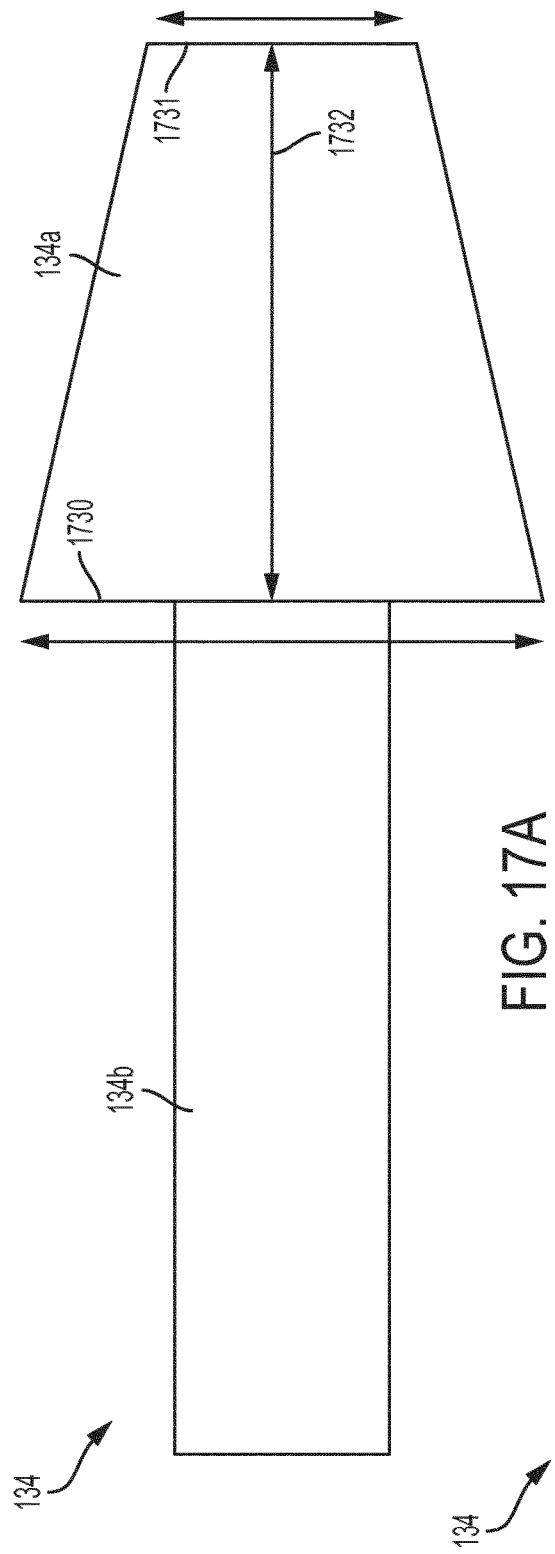
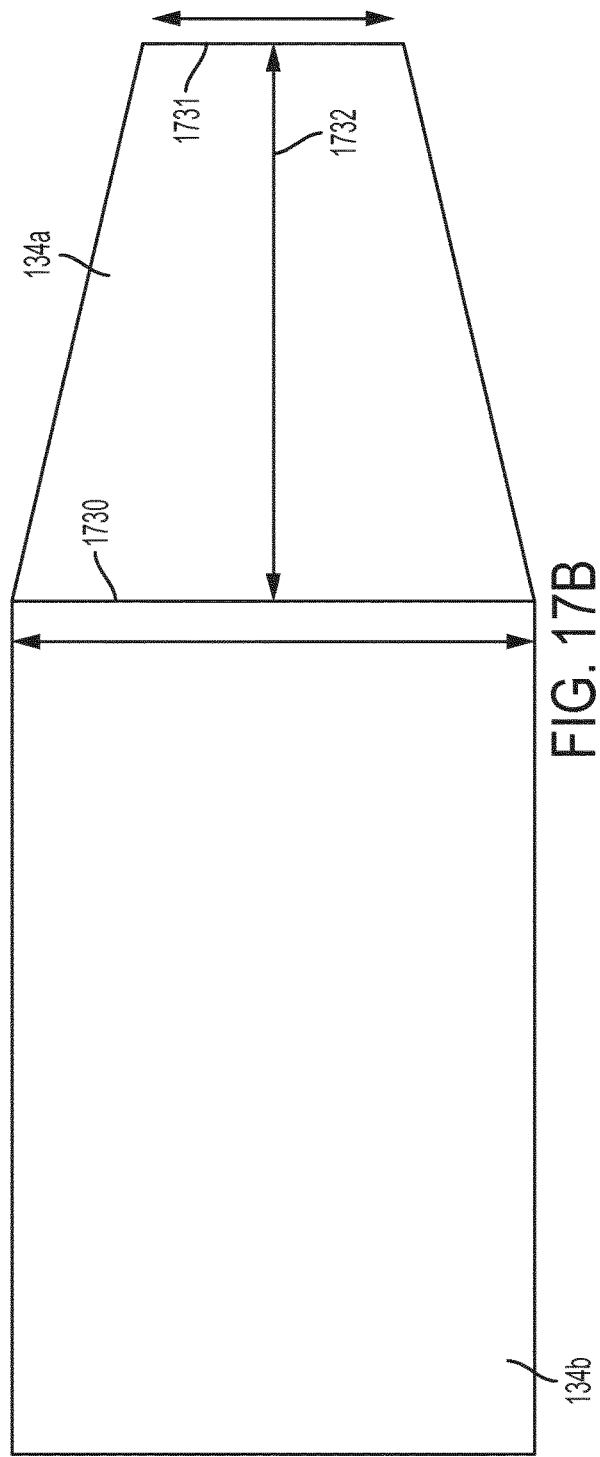

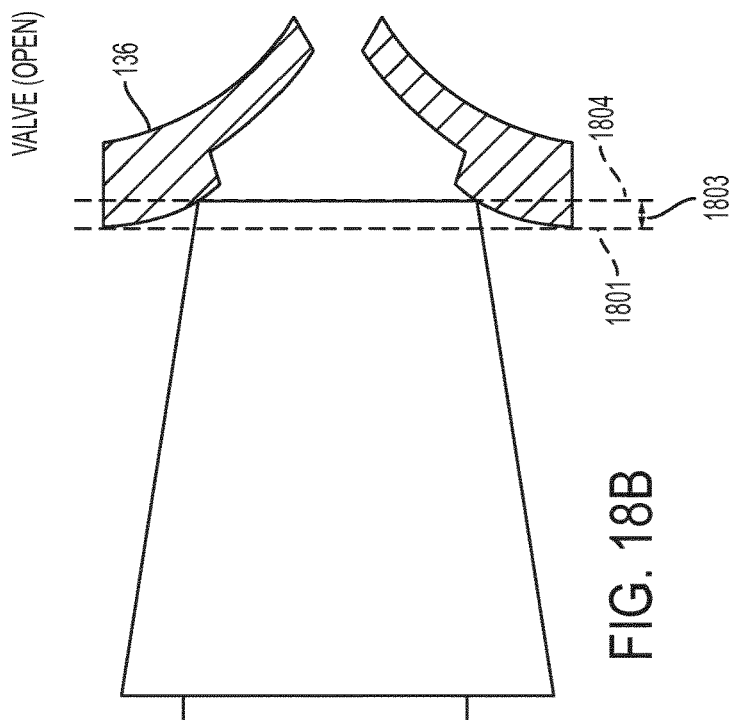
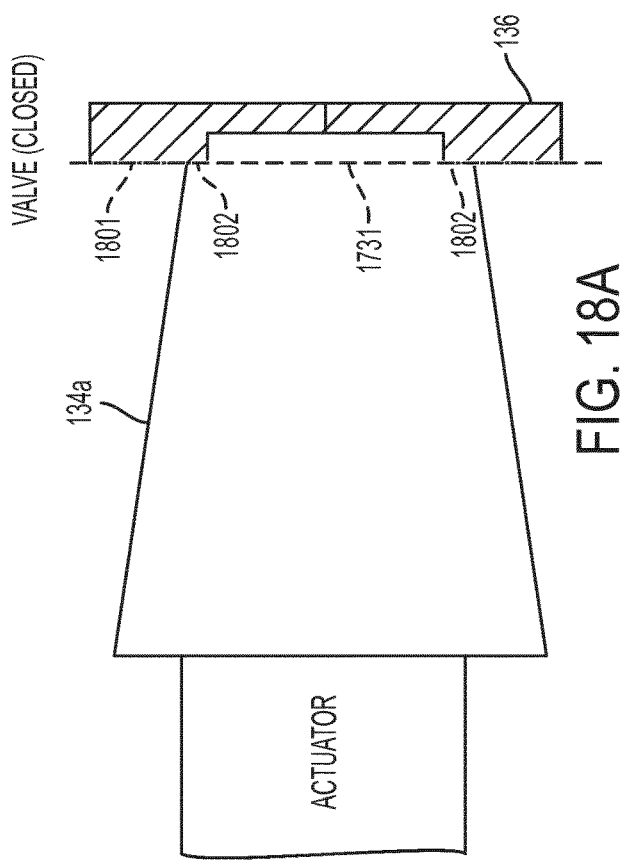
FIG. 18A
FIG. 18B

VALVED CATHETER ASSEMBLIES AND RELATED METHODS

FIELD OF ART

The disclosed invention generally relates to needle devices and intravenous (IV) infusion devices, including IV catheters or catheter assemblies. In particular, IV catheter assemblies having a valve and a valve actuator for opening the valve are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

Aspects of the present invention include a catheter assembly having a catheter hub with a catheter tube and a needle hub with a needle projecting through the catheter hub and the catheter tube in the ready to use position. The catheter hub can have a valve located therein for controlling flow thereacross. The valve can be actuated by fluid pressure or can be actuated by physical contact using a valve actuator. A needle guard can be located inside the catheter hub to cover the needle tip following successful venipuncture or can be located in a separate third housing located outside of the catheter hub.

An IV catheter assembly can have a valve and have a catheter hub, which can be a two-part hub body or a singularly formed hub body. Further information regarding catheter assemblies are discussed in U.S. Pat. No. 9,114,231, the contents of which are expressly incorporated herein by reference. In other examples, a ported catheter assembly or an integrated catheter assembly having an integrated tubing can be practiced with the valve and valve opener described herein.

A distal hub element or first hub part of the two-part catheter hub can have a holding section, such as a nose section, in which a catheter tube is held, such as with a metal bushing. The proximal end of the first hub element or part can have an enlarged diameter relative to the nose section of the distal end portion and forms a connecting section for connecting with a rear hub element or second hub part.

The two-part hub configuration can facilitate assembly of a valve and a valve opener, as further discussed below. However, catheter assemblies described herein are not limited to a two-part hub as a singularly formed hub or three or more hub parts may be used to form a catheter hub without deviating from the scope of the catheter assemblies described herein.

The distal end of the rear hub part overlaps the proximal end of the front or first hub part and which is provided at its proximal end with a female Luer fitting and exterior threads, forming a female threaded Luer. In some examples, the threads can be omitted and the proximal opening can function as a female Luer slip.

Between the two hub parts, a valve in the form of a check valve shaped as a cylinder with a valve disk or disc, or a valve disk without a skirt is inserted and is fixed in place by the two hub elements. In other embodiments, a single hub body is used and the valve is held in place by placing the valve next to or against a shoulder in the interior of the single hub element. A second shoulder may be incorporated to secure the valve in place with adhesive or bonding being optional.

In still yet other examples, a single catheter hub body is used with internal shoulders or undercuts incorporated for retaining the valve therein, without adhesive or bonding. In still another embodiment of the present disclosure, the valve is held in the catheter hub by an interference fit.

In a ready position, a nose section of a needle hub is inserted into the catheter hub. A hollow needle is fixed to the nose section and extends through the valve, the catheter hub, and the catheter tube so that the needle tip is exposed beyond the tapered end of the catheter tube. Between the needle hub and the valve and inside the catheter hub, a valve opening device, valve actuator, or valve opener with a nose end for opening the valve is slidably or displaceably arranged. In an example, the nose end of the valve opener has a truncated cone-shaped locating section or a tapered section. In other examples, the valve actuator has a nose section with a radiused tip, a square tip, or a tip with angular surfaces. In still other examples, the valve opener can be omitted and the valve can be sized and shaped to deflect under fluid pressure, such as under IV fluid head pressure, under syringe discharge pressure, etc.

On the proximal side of a valve actuator, a plunger section or pusher end can be provided. The plunger section can be sized and shaped to be pushed by a male Luer conical fitting of a medical implement, such as a syringe tip or an IV tubing adaptor, to open the valve. The pusher end adjoins the nose end of the valve actuator.

In an example, the nose section incorporates a groove to facilitate engagement with the valve so that even if the medical implement no longer pushes on the valve actuator, the nose section remains engaged with the valve.

Various embodiments of valve openers can be used with the valves of the present application. In one example, there is only a single element or leg forming the pusher end. In another example, two legs with a hollow space therebetween or a gap are provided. The two proximal ends of the two legs can provide a surface to be pushed by the medical implement.

The space between the two legs can be sized to receive a needle guard element or tip protector. For example, the needle guard element can be positioned in the space between the two legs.

In still other examples, the pusher end of the valve actuator can be a cylinder having one or more openings through the cylinder to provide space or access for engagement with a needle guard, which can engage the catheter hub through the one or more openings or engage an edge of each of the openings of the cylinder, if more than one opening.

In other examples, a third housing having a cavity is positioned between the catheter hub and the needle hub. The needle guard element may be positioned in the cavity of the third housing and the third housing can have mechanical features to engage the catheter hub and the needle hub. For example, the third housing can have an extension that contacts the interior or the exterior of the catheter hub to secure the third housing to the catheter hub and/or to prevent early activation of the needle guard.

In some examples, the needle guard is omitted and the catheter assemblies only incorporate a valve and a valve opener. In still other examples, the needle hub can be provided with a spring loaded needle carrier that is expelled into a hollow barrel following successful venipuncture.

On withdrawal of the hollow needle from the catheter hub following successful venipuncture, a change in profile provided near the needle tip and having the form of a radial projection on the hollow needle, such as by crimping, engages with the outer circumference defining the proximal opening on the rear wall or proximal wall of the needle guard so that the needle guard can be removed from the catheter hub with the needle.

As the needle tip moves proximal of the two distal walls of the two arms, the two arms move, such as spring or deflect radially to disengage from the interior of the catheter hub. As the arms of the needle guard move radially, the arms, or the distal walls of the arms, cover the needle tip to prevent unintended needle sticks. In other examples, the change in profile can include a sleeve, a notch, or a material buildup on the shaft of the needle.

Subsequent to removal of the needle following successful venipuncture, the two or more flaps of the valve, due to their elastic properties, close the one or more slits through the depth of the valve disk or disc so that no blood or substantially no blood can flow out through the catheter.

Valves provided herein can include three slits starting from the middle of the valve and extending radially over a short radial distance towards the outer perimeter to form elastic flaps that can be expanded by the hollow needle and closed when the needle is removed. In some examples, the flaps can remain open and engaged with a valve opener, which can be referred to as a one-time use valve.

A syringe tip of a syringe can abut the pusher end of a valve actuating element and pushes the valve actuator against the valve so that the nose section of the valve opener advances against the flaps of the valve to open the slits thereby opening the valve so that liquid can flow thereacross.

In embodiments with re-usable valves, the nose section of the valve opener is sized and shaped to separate from the flaps of the valve after removal of the male Luer tip, such as a syringe tip. The elasticity of the valve allow the flaps to uncoil and for the valve actuator to move proximally.

The nose end of an actuator can have an inclined shape. Thus, as the syringe is removed and the forward force on the actuator is removed, the elasticity of the material of the valve is sufficient for the two or more flaps to uncoil and push the actuator in the proximal direction to close the seal. The valve therefore automatically closes upon withdraw of the pushing force on the actuator and can be re-used by inserting a male Luer tip into the catheter hub to again advance the valve opener into the valve to open the flaps.

A shoulder can be provided in the catheter hub. The shoulder can act as a proximal stop for the actuator when the flange on the actuator abuts the shoulder, which defines the proximal most position of the flange of the actuator. In other examples, the second hub section may incorporate other structural features, such as a tapered internal cavity, to stop the proximal travel of the actuator.

The catheter hub can include a second shoulder just proximal of the first shoulder. The two radially outer areas of the spring arms of the needle guard, which may be referred to as elbows between the distal walls and the two elongated sections of the two arms, can abut the second shoulder inside the catheter hub in the ready position. In some embodiments, the second shoulder can be an annular projection, an annular recess, a raised section adjacent a recess section, or partial projections or recesses. In still other examples, the first shoulder is omitted and only one shoulder is incorporated for retaining the elbows of the needle guard.

When the needle hub with the hollow needle is removed from the catheter hub, the needle guard can be held generally stationary by the second shoulder until the change in profile, such as a crimp, near the needle tip comes to abut on the rear proximal wall of the needle guard and the needle tip moves proximally of the two distal walls on the needle guard. At this point, the two spring arms, which are no longer restrained in the radial direction by the needle, spring inwards to cover the needle tip and separate from the second shoulder, whereupon the needle guard with the hollow needle can be removed from the catheter hub. Further information regarding the needle guard is discussed in U.S. Pat. No. 7,736,339, the contents of which are expressly incorporated herein by reference.

Further information regarding various aspects of valved catheter assemblies are discussed in PCT patent applications PCT/EP2016/069619, published as WO2017/029361, and PCT/EP2016/069643, published as WO2017/029374, the contents of which are expressly incorporated herein by reference.

A catheter assembly of the present disclosure, which may more broadly be referred to as a needle assembly or a needle device, can include a catheter hub with a catheter tube having a distal opening, and a bushing with a distal valve opener and a proximal valve opener or actuator. Aspects of the catheter assembly with the bushing and distal valve opener are disclosed in PCT patent applications PCT/EP2016/069619 and PCT/EP2016/069643. The bushing can be configured to wedge the proximal end of the catheter tube against the interior wall surfaces of the catheter hub to retain the catheter tube to the catheter hub and the distal valve opener can cooperate with the proximal valve opener to open a valve.

Interiorly of the catheter hub, a septum or valve, a valve actuator, such a proximal valve actuator or opener, and a safety clip, such as a needle guard or tip protector, can be provided. A needle can be inserted through the proximal opening of the catheter hub, with the needle tip protruding out the distal opening of the catheter tube in a ready to use position of the catheter assembly. A cannula hub or needle hub can interconnect with the proximal end of the needle and contact the catheter hub in a ready to use position. The proximal opening of the catheter hub is sized and shaped to receive a male medical implement, such as a male Luer tip.

The tip protector can be located inside the catheter hub and can be configured to be removed with the needle following use and the valve and valve actuator remain with the catheter hub for controlling fluid flow therethrough. As described in in PCT patent application PCT/EP2016/069619 and shown herein, the tip protector has a proximal wall with a perimeter defining an opening and two arms extending distally of the proximal wall. One or both arms of the tip protector can have a distal wall for blocking the needle tip in a protective position and both arms can remain on different sides of the needle or the arms can cross the needle axis and intersect when viewed looking at the side of the needle. The actuator is configured to be pushed into the valve to open the valve for fluid flow.

A flash back plug can be provided at the proximal end of the needle hub, which allows air to vent but stops blood from spilling out the proximal end when entering the flashback chamber during primary flashback. Alternatively, a syringe can be attached to the proximal end of the needle hub. The valve and actuator described can also be placed within the needle hub as a second valve. The needle hub can comprise a shoulder or other surfaces to physically contact the catheter hub, such as the proximal end surface of the catheter hub, to axially register the two hubs to set the length of the needle tip projecting out of the distal opening of the catheter tube.

The valve opener can comprise a ring or nose section and at least one plunger element, such as a leg element or an elongated extension. The nose section or ring can contact with the valve in the needle assembly ready to use position but can be slightly spaced from the proximal surface of the valve.

In an exemplary embodiment, two plunger elements can extend from the ring or nose section in the proximal direction and each having a length measured in a lengthwise direction of the catheter assembly and a width, measured orthogonally to the length. The at least one plunger element can be sized and shaped for contact by a male Luer to transfer a distally directed force from the male Luer to the ring to then open the valve. For example, the valve is pushed distally by the proximal valve opener against the distal valve opener, which pushes the valve flaps in the proximal direction to open the slits of the valve for fluid flow.

A valve opener provided herein can comprise a nose section with an activation end and a plunger end extending in the proximal direction of the nose section. However, rather than incorporating two plunger elements with two free ends, the present embodiment incorporates a band or ring connecting the two plunger elements together. The band or ring can comprise two arc-shape, curved sections, or stabilizer elements attached to the two plunger elements to form the band or ring. The band can be called a stabilizing ring and can connect the two plunger elements together to form a stabilizing structure. The stabilizing ring can form a continuous perimeter section of the valve actuator that is spaced from another continuous perimeter section defined by the nose section of the valve actuator. In other examples, only a single arc-shape or curved section attaches to the two plunger elements.

The present valve actuator embodiment can be viewed as a valve opener with a single plunger element extending from a nose section and wherein the single plunger element comprises two or more reliefs or through passages formed through the wall of the plunger end. The needle guard can engage the edges or perimeters of the reliefs in the ready to use position and during retraction of the needle following successful venipuncture.

Alternatively, the tip protector or needle guard can project from the holding space defined by the valve opener through the reliefs to engage the interior surface of the catheter hub. Still alternatively, the tip protector can project through the reliefs but not contact the interior of the catheter hub or the perimeters. Still alternatively, the tip protector can project through the reliefs, contacts the interior of the catheter hub, and contacts one or both perimeters of the reliefs. The part of a tip protector that can project through one or both reliefs can be one or two elbows of a tip protector.

The needle guard of the present embodiment can be positioned, at least in part, in a holding space of a valve opener. When situated in the holding space of the valve opener, the needle guard or tip protector can project through one or both reliefs of the valve opener. The part or parts of the needle guard that project through can contact the interior of the catheter hub, be spaced from the interior of the catheter hub, can contact one or both perimeters of the reliefs, or be spaced from one or both perimeters of the reliefs, or combinations thereof. The part of the needle guard that projects can be one or two elbows of a needle guard.

A holding space can be a gap in the valve actuator that can accommodate the needle guard. Reliefs can be access openings formed in the body of the valve opener.

Thus, in the embodiment with two reliefs or through passages, the perimeters of the two reliefs or through passages can function as guard engagement sections by allowing the elbows of the tip protector or needle guard to engage thereto. Alternatively, the two elbows of the needle guard can project through the two reliefs from the holding space defined by the valve opener to engage the guard engagement sections or segments formed on the interior surface of the catheter hub. Thus, the perimeters of the reliefs or the interior surfaces of the catheter hub can form anchor points for the arms of the tip protector to engage thereto in the ready to use position and during retraction of the needle following successful venipuncture.

In an alternative example, a single plunger element of a valve opener can embody a generally cylindrical body section having an interior surface defining a bore having a path or channel, which can also be a gap for fluid flow, and a proximal perimeter or end edge. A guard engagement section can be formed on the interior surface of the present valve opener, without reliefs or through passages. In other words, the projection, bump, recess or guard engagement section can be formed on the interior wall surface of the valve opener to allow engagement between the needle guard and the interior surface of the valve opener.

When a valve opener is used with a needle device or catheter assembly, the guard engagement segment can be on the catheter hub, on the interior wall of the valve opener, or a perimeter of a relief formed through the wall of the valve opener. There can be one or more reliefs or guard engagement segments incorporated with the valve opener. There can also be one or more guard engagement segments formed with the catheter hub for use with the one or more reliefs of the valve opener. This allows the two resilient arms of the tip protector to engage the valve opener or to engage the catheter hub by projecting through the reliefs.

Interiorly of a catheter hub, a septum or valve, an actuator or valve opener and a safety clip, such as a needle guard or tip protector, can be provided. A needle, which can have a change in profile, can be inserted through the proximal opening of the catheter hub with the needle tip protruding from the distal opening of the catheter tube in a ready to use position.

A cannula hub or needle hub can attach to the proximal end of the needle and can contact the proximal end of the catheter hub when assembled thereto in the ready to use position. The proximal opening of the catheter hub can be sized with a female Luer taper, optionally with external threads, to engage with a male Luer tip in a Luer slip or a Luer lock.

The tip protector is configured to be removed with the needle following use and the valve and valve actuator remain with the catheter hub for controlling fluid flow therethrough. The actuator can be configured to be pushed distally by a male tip into the valve to open the valve for fluid flow.

A flash back plug or blood stopper assembly can be connected to the needle hub to stop blood flow out the flashback chamber of the needle hub. The flash back plug can be provided at the proximal end the needle hub to allow air to vent but stops blood from spilling out the proximal end of the body of the flash back plug, which has a chamber and a hydrophobic filter is assembled in the chamber. Alternatively, a syringe can be attached to the proximal end of the needle hub. A second valve and actuator can also be placed within the needle hub.

A protective cap with a sleeve and a saddle can be provided to cover the needle during packaging and before use, which is conventional. The saddle can surround at least part of the catheter hub and the needle hub 106 and be removably engaged to the needle hub. The cap should be removed from the needle assembly before use. The catheter hub can be provided with a pair of wings to facilitate securement of the catheter hub to a patient following use.

A bushing can be used to retain a catheter tube to a catheter hub. The bushing can comprise a body comprising a first body section, a second body section extending from the first body section, and two or more leg extensions extending from the second body section.

The first body section can have an elongated body that can have a cylindrical shape with an optional tapered distal tip or nose section. In some examples, a generally cylindrical ring extends from the second body section and the two or more leg extensions extend from the cylindrical ring.

One or more gaps can be provided between two adjacent leg extensions. In an example, the number of leg extensions incorporated with the bushing can be the same as the number of flaps incorporated with the valve. Thus, if the valve has three flaps, then there can be three leg extensions on the bushing. If the valve has a single slit, then there can be two leg extensions. In other examples, the number of leg extensions and the number of flaps can differ. The leg extensions on the bushing can define an outside diameter that is smaller than the minimum inside diameter of the valve opener.

The proximal tip of each leg extension can have a chamfer or a blunt tip. In one example, a chamfer is incorporated at the proximal tip of each leg extension and wherein the chamfer tapers inwardly from the exterior of the leg extension. This chamfer direction is configured to match the folding direction of the flaps on the valve. The bushing can be made from a metal material and the leg extensions can be unitarily formed with the body. Alternatively, the leg extensions can be welded to the body.

When positioned in the catheter hub, the bushing and the valve can be oriented so that the leg extensions on the bushing are aligned with the flaps on the valve. In other words, the two components can be aligned so that when the valve is advanced distally by a proximal valve opener from the proximal side of the valve, the flaps on the valve are pushed into physical contact with the leg extensions on the bushing. Thus, if there are three flaps on the valve, the three flaps will be pushed into physical contact with three leg extensions on the bushing on the distal side of the valve.

The distally facing wall surface of the valve can touch the leg extensions and/or a resilient element or be spaced from the leg extensions on the bushing and/or the resilient element in the valve closed position and be pushed against the leg extensions during use. In other examples, the valve can touch the proximal tips of the leg extensions and/or the resilient element in the closed position of the valve or be spaced therefrom. If spaced from the leg extensions and/or the resilient element, the valve can be displaced axially into contact therewith.

A catheter assembly provided herein, which may more broadly be referred to as a needle assembly or a needle device, can comprise a catheter hub with a catheter tube having a distal opening, and a bushing with a distal valve opener. The bushing can be configured to wedge the proximal end of the catheter tube against the interior wall surfaces of the catheter hub to retain the catheter tube to the catheter hub.

An aspect of the present disclosure is understood to include a valve opener for opening a valve. Optionally, the valve can be configured to open under fluid pressure without a valve opener. The valve opener can be configured to push the valve against another structure, such as the leg extensions on the bushing. The present valve opener may be viewed as having a multi-piece valve opening structure. For example, the part with the ring and the plunger elements may be viewed as a proximal valve opener and the bushing with the leg extensions may be viewed as a distal valve opener. The bushing and the distal valve opener can be unitarily formed. Optionally, the outer edge of the valve can be fixed and the flaps on the valve deflectable using only a proximal valve opener.

The two valve openers can cooperate to open the valve. The proximal valve opener can be sized and shaped to push against the outer edges of the valve in the distal direction to move the valve against the distal valve opener. The distal valve opener is sized and shaped to push the flaps on the valve in a radially outward direction and part of the flaps in a proximal direction to open a fluid path or flow path through the valve.

In an example, the leg extensions on the distal valve opener are axially fixed and by pushing the flaps of the valve in a distal direction against the leg extensions, the flaps are deflected radially outward by the leg extensions on the distal side of the valve. In other words, when the valve is actuated to open a flow path through the valve, the valve is being physically pushed by an actuator on a proximal side of the valve and an actuator on the distal side of the valve. In a particular embodiment, the valve can be actuated to open a flow path through the valve by being physically pushed by a ring on a proximal side of the valve and leg extensions on the distal side of the valve.

An actuator provided herein can comprise a generally cylindrical nose or nose section, such as a conical frustum shape nose, and an activation end at a distal end thereof. Actuating arms can extend lengthwise from the nose section. In the ready position and if used with the catheter, the nose section may be in contact with the valve disc or can be slightly spaced from the proximal surface of the valve disc.

A relief or through passage provides access for a tip protector to engage with the interior of the catheter hub. In one embodiment, two through passages or reliefs on opposite sides of the body of the actuator are provided to give access to the interior of the catheter hub to two corresponding arms of a tip protector. Other embodiments can have a different number of through passages, such as one, three or more, can be incorporated. For example, there may be three through passages spaced between three actuating elements.

In illustrated embodiment, stabilizers connect the two actuating elements and form a ring structure on the proximal end of the actuator, also called a stabilizing ring. The stabilizers can provide additional rigidity and/or engagement surfaces for the actuator to interact with a needle guard and/or with the interior of the catheter hub. In some embodiments, the stabilizing ring comprises one, two, or more individual sections that form a substantially cylindrical section of the actuator body. The stabilizers can be continuous and connect to the two actuating elements or can be open or non-continuous, each with a gap or a slit.

The stabilizers can have edges that align with each other or may be offset. In still other examples, one or more leg extensions can extend proximally of the stabilizers. For examples, two leg extensions can align with the two actuating arms and extend in the proximal direction from the stabilizers. The length of the leg extensions that extend from the stabilizers can be selected as appropriate for pushing by a male Luer tip to push the valve opener in the distal direction to open the valve.

A majority of the tip protector can be fitted inside the holding space of the actuator, with a portion of the tip protector extending in the proximal direction past the proximal end of the actuator. For example, the proximal wall and part of the two arms of the tip protector extend radially through the relief of the actuator. One or more ribs or projections can be formed on the exterior surface of the actuating arms and can engage with a shoulder of the catheter hub to retain the actuator inside the catheter hub in the ready to use position and used position.

Where leg extensions are incorporated, the proximal wall of the needle guard can be even with the proximal end most of the two leg extensions or the proximal end most of the two leg extensions can extend further proximally of the proximal wall.

The present disclosure further relates to valves for use in IV catheters that can prevent blood leakage in multiple access use situations, such as repeated use situations. Exemplary catheter assemblies and components that the valves can be used with are shown in FIGS. 1A, 1B, and 20-25C. An exemplary valve is shown in FIG. 20 and is configured for multiple use with other alternative valves disclosed herein further below. The valve can be opened by a valve opener or actuator on insertion of a Luer connector which can push the valve actuator distally to open the valve.

The valve can open with just a proximal valve opener or the valve can be pushed against a distal valve opener to open the valve, as previously described. When the Luer connector is withdrawn, the valve is configured to return to its closed configuration with adequate sealing to substantially limit or prevent blood leaking out through the valve. In some examples, the valve is configured to return due to the elastomeric properties of the valve. As discussed in PCT patent applications PCT/EP2016/069619 and PCT/EP2016/069643, a spring or resilient element can be incorporated to facilitate returning the valve to its closed position where fluid is restricted or stopped from flowing thereacross.

In some examples, a relatively thinner area or cross-sectional profile of the valve around a slit is provided to reduce the drag force between the needle and the valve when the needle is withdrawn and moving against the surfaces of the slit. A single slit can define two flap sections on either side of the slit. Three slits formed through the valve can define three flaps, and so forth. The three slits can converge at a single point, which can define the middle or center of the valve.

The thicker area of the valve compared to the relatively thinner area can provide rigidity so that the flaps on the valve defined by the slit are able to return to a closed configuration when the Luer connector is removed, thereby enabling multiple access use.

In some examples, the thicker area is provided by incorporating one or more ribs. One advantage to having ribs instead of just increased thickness around the perimeter of the valve is to further reinforce the valve. This can improve the recovery and sealing of the valve for multiple access use.

Embodiments of the present disclosure may aid in reducing drag and deformation of the valve when removing the needle following successful venipuncture.

Generally, the valve is considered as having a proximal side and a distal side, with the proximal side being the side closer to or the side facing the proximal end of the catheter hub, which has the proximal opening that opens to the interior of the catheter hub. However, the orientation of the valve may be reversed as one of ordinary skill might see fit. In some examples, more than one slit can be incorporated with the valve to define more than two flaps.

In some examples, the valves described herein can be used with a catheter assembly having a proximal valve opener for opening the valve located in a catheter hub without a distal valve opener. Exemplary valve assemblies with a proximal valve opener only are disclosed in U.S. Pat. No. 9,114,231 and PCT patent application PCT/EP2016/069619.

A valve provided herein can have a first portion having a first thickness and a second portion having a second thickness less than the first thickness, measured orthogonal to the medial plane.

The second portion can have a first region of a substantially constant thickness and a second region having a varying thickness along a cross-section. The thickest part of the second region of the second portion can be larger than the thickest part of the first region. The first region can be at or near the valve center and the second region of the second portion further away from the valve center.

The second region can be located radially outward from the first region near an outer perimeter of the valve. The first region has a surface substantially parallel to a surface of the first portion. The surfaces of the first portion and of the first region can be on two different planes. The second region can have a surface bridging the surface of the first region and the first portion. The surface of the second region can taper between two different planes.

Embodiments can be envisioned where the surfaces of the first region and the first portion are not parallel to one another. Additionally, although the exemplary valve shows substantially flat surfaces for the valve, non-flat surfaces could also be used.

From the first portion, three ribs can extend radially inward towards the center of the valve. While the ribs are flush with the surface of the first portion, the ribs can be defined as a raised or ribbed structure between sections of the second portion. The ribs can have a same thickness as that of the first portion. The ribs can be thicker than that of the first portion.

Each of the ribs can comprise of first sides that are substantially parallel to one another. The ribs each extend inwardly with a substantially constant width between the first sides. The first sides can have a tapering thickness as they extend radially inward, due to the angle of the second region. The ribs each have second sides, which converge towards a point at an inward most end of the rib. Optionally the second sides of the ribs can be rounded or have blunt ends.

In an embodiment, the tips of each second sides or the ribs define an actuating region. As further discussed below, the actuating region is smaller than the tip of a valve actuator head so that the valve actuator head pushes against the ribs rather than the first region of the second portion during activation of the valve.

The ribs extend radially inward adjacent to the first region and the second region. The second portion thus has a petal like arrangement formed from the first sides and second sides. The second region further has an outer arcuate side and two radiused corners. Accordingly, the outline of the arcuate side, two radiused cornered, first sides, and second sides delineate the first portion and the second portion.

Embodiments can be envisioned where the rib has alternative geometric shapes, such as a rectangle. The inward most end at sides of the rib does not have to converge to a point. Alternatively, the first sides of the ribs do not need to be parallel to one another. The first sides may be skewed from one another to converge without second sides.

In the first region, three slits are provided through the valve from the proximal side to the distal side. The slits can extend radially and connect to a point in the center. The slits define flaps. In the particular example, the three slits can be provided through the valve to define three flaps. The flaps are configured to be moveable relative to the outer perimeter of the valve to allow for fluid flow. The three slits can each extend lengthwise to the edge of the second region. The three slits can each be within the first region. Alternatively, the three slits can each extend lengthwise into the second region. The three slits are spaced from the three ribs. That is, the slits do not cut into the ribs. In other examples, the slits can cut into the ribs and part of the first region.

The valve can have an outer perimeter that is axially fixed within the interior of the catheter hub. The valve can be opened with just a proximal valve opener. For example, the proximal valve opener can move into the valve by a male Luer tip to deflect one or more flaps on the valve. Any part of a valve can be axially fixed by the interior surface structure of a catheter hub so that the flaps can be pushed relative to the outer portions of the valve. In still other examples, the valve can be actuated to open by a valve assembly having both a proximal valve opener and a distal valve opener. Optionally, the valve can have a cylindrical skirt section extending along the outer perimeter of the valve, as further discussed below.

Along a medial plane, the features of valve can be symmetrical and reflected on both the first surface and the second surface, which can also be referred to as a proximally facing surface and a distally facing surface when the valve is mounted inside a catheter hub. As such, the proximal side and the distal side of the valve are symmetrical. Where the dimensions of the features of the first portion and second portion are the same on both sides of the valve, the features may still be rotated around the axial center of the valve relative to the other side of the valve, such that the features on the proximal side are offset from the distal side when viewed from a top down orientation along the axial direction of the valve.

Alternatively, the opposed sides of the valve can have different dimensions for each of the first portion and second portion. For example, the various thicknesses of the ribs and second region of the second portion can be different when comparing the same elements of the proximal side and the distal side. In other embodiments, only one side of the valve can have the geometrical features and the opposed side being generally flat throughout.

The exemplary illustration shows the first portion and the first region having surfaces substantially parallel to the medial plane. Embodiments can be envisioned where the surfaces of the first region and the first portion are not parallel to one another or the medial plane. The second region has a surface bridging the surface of the first region and the first portion. In the exemplary illustration, the second region has a substantially flat surface arranged in a ring shape. Other surface geometries can be used, such as angular step downs or with convex or concave shaped curved surfaces as necessary to bridge the surfaces of the first region and the first portion.

The valve may be integrally formed of a single material. Alternatively, the valve may be formed of different materials in various portions of the valve for reasons such as improved rigidity or flexibility. The valve can be made from a medical grade elastomer or a thermoplastic elastomer (TPE).

One advantage of having arrow shaped ribs extending towards the slit is to have earlier contact between the valve opener and the valve upon insertion of a Luer connector before contact with a surface having the slits. Therefore, the relatively earlier contact allows earlier opening of the valve by reducing the travel distance needed by the valve opener to open the valve. Said differently, the girth or thickness provided by the ribs allow the valve to be contacted earlier by a valve opener compared to a similar valve without the disclosed ribs extending further in the proximal direction than the surfaces having the slits.

Still further, the relatively thinner area of the valve near the valve center reduces drag on a needle while still allowing for the valve to be actuated earlier and with increased resiliency, due to the presence of the ribs.

There is a possibility of a contact between the tips of the ribs with the needle due to some deflection of the flaps when the needle projects through the slits in a ready to use position. In the event of contact, having an arrow-shaped tip or a reduced tip region for each rib instead of a straight (rectangular) edge tip can help to reduce the contact area between the rib tips and the needle, thereby reducing friction and drag force when the needle is withdrawn.

An advantage of the curved recesses having sloped surface between the thicker valve area and thinner valve area is to ease the molding. There is also a tendency for blood to clot in areas with sharp steps or angles; therefore the curved shape and sloped surface can reduce the risk of blood clot formation.

An alternative valve of the present disclosure can be asymmetrical across a medial plane. The valve can have an outer perimeter having a cylindrical portion or skirt with a first end and a second end. The cylindrical portion or skirt extending from the valve disk at the first end adds to the overall length of the valve. The sidewall of the cylindrical portion can be defined by the inner surface and the outer surface can have a constant thickness.

Inside of the cylindrical portion can be a central portion 314, which can be referred to as a valve disk or disc. The central portion can include a first portion having a first thickness and a second portion having a second thickness less than the first thickness. Both the first portion and the second portion can have thicknesses less than the cylindrical portion. Additionally, the first portion and the second portion can be offset from the medial plane of the valve.

The second portion can have a first region of a substantially constant thickness and a second region having a varying thickness. The second region is located radially outward from the first region near an outer perimeter. The first region can be a surface substantially parallel to a surface of the first portion. The second region can have a surface bridging the surface of the first region and the first portion.

Embodiments can be envisioned where the surfaces of the first region and the first portion are not parallel to one another. Additionally, although the exemplary valve shows substantially flat surfaces for the valve, non-flat surfaces could also be used.

From the first portion, three ribs extend radially inward towards the center of the valve. The ribs can have a same thickness as that of the first portion. Each of the ribs can comprise of first sides that are substantially parallel to one another. The ribs each extend inwardly with a substantially constant width between the first sides.

The ribs can each have second sides, which converge towards a point at an inward most end of the rib. The ribs extend radially inward adjacent to the first region and the second region.

In the first region, three slits can be provided through the valve from the proximal side to the distal side. The slits can extend radially and connect to a point in the center. The slits define flaps that can deflect to open the valve. In the particular example, the three slits provided through the valve define three flaps. The flaps can be moveable relative to the outer perimeter of the valve to allow for fluid flow. The three slits can each extend lengthwise to the edge of the first region. The three slits can each be within the first region. Alternatively, the three slits can each extend lengthwise into the second region.

The first portion of a valve disc can be integral with an end portion of the cylindrical portion. In an embodiment, the end portion can be the distal side of the valve as oriented inside the catheter hub. As shown, the central portion is offset in an axial direction from the medial plane of the valve and is at an end portion of the valve. Alternatively, the central portion can be inset from the end of the cylindrical portion. Still alternatively, the cylindrical portion can be orientated in the proximal direction when located inside the catheter hub.

A further valve of the present disclosure can have a central portion located in-between an outer cylindrical portion. The central portion can be referred to as a valve disk or disc. In this way, the central portion can be positioned as a septum, or partition separating two interior recesses of a cylinder. The central portion can be located between the two ends of the cylindrical portion to define two interior spaces or recesses. The two interior spaces or recesses can be similar in size or can be unequal in size. In an example, the smaller interior space can be positioned distally of the relatively larger space.

The cylindrical portion can add to the overall length of the valve. Inside of the cylindrical portion, the central portion can include a first portion having a first thickness and a second portion having a second thickness less than the first thickness. Both the first portion and the second portion have thicknesses less than the cylindrical portion. Additionally, the first portion and the second portion can be offset from the medial plane of the valve.

The second portion can have a first region of a substantially constant thickness and a second region having a varying thickness. The second region can be located radially outward from the first region near an outer perimeter. The first region can have a surface substantially parallel to a surface of the first portion. The second region can have a surface bridging the surface of the first region and the first portion.

Embodiments can be envisioned where the surfaces of the first region and the first portion are not parallel to one another. Additionally, although the exemplary valve shows substantially flat surfaces for the valve, non-flat surfaces could also be used.

From the first portion, three ribs extend radially inward towards the center of the valve. The ribs can have a same thickness as that of the first portion. Each of the ribs comprises of first sides that are substantially parallel to one another. The ribs can each extend inwardly with a substantially constant width between the first sides. The ribs each have second sides, which converge towards a point at an inward most end of the rib. The ribs can extend radially inward adjacent to the first region and the second region.

In the first region, three slits can be provided through the valve from the proximal side to the distal side. The slits can extend radially and connect to a point in the center. The slits can define flaps. In the particular example, the three slits provided through the valve define three flaps. The flaps can be configured to be moveable relative to the outer perimeter of the valve to allow for fluid flow. The three slits can each extend lengthwise to the edge of the first region. The three slits can each be within the first region. Alternatively, the three slits can each extend lengthwise into the second region.

Furthermore, the outer cylindrical portion may be a tapered surface on at least one of an exterior surface and an interior surface. The surface may taper from approximately where the central portion is located along the cylindrical portion to an end of cylindrical portion. In embodiments, both ends of the cylindrical portion may be tapered from approximately where the central portion is located along the cylindrical portion to an end of cylindrical portion. This may be for ease of manufacturing and for ease of assembly into an assembly without concern for orientation of the valve. In some embodiments, the entire cylindrical portion may be tapered from one end to the other on at least one of the exterior surface and the interior surface.

A further embodiment of a valve can have differing diameters for the interior recesses. The outer cylindrical portion can have three circumferential regions. A diameter of an inner surface of a first circumferential region can be larger than a diameter of an inner surface of the third circumferential region.

A diameter of an outer surface of the first circumferential region can be larger than a diameter of an outer surface of the third circumferential region. A ridge surface of the second circumferential region can have a diameter larger than either of the first circumferential region and the third circumferential region.

The inner surface and the outer surface of the first circumferential region can be substantially parallel and define a sidewall. The ridge surface, as viewed cross-sectionally along the axial direction of the valve, is parallel to the outer surface of the first circumferential region. The ridge surface of the second circumferential region is projected outwardly from the first circumferential region and the third circumferential region with two ridge side surfaces. The second circumferential region can correspond to a thickness of the central portion.

The ridge side surfaces can be parallel to each other and extend in a radial direction of the valve. Alternatively at least one of the ridge side surfaces can extend radially in an angled direction to form a conical surface.

The outer surface of the third circumferential region may be tapered inwardly towards the center of the valve towards a distal end of the cylindrical portion. The inner surface of the third circumferential region may be tapered outwardly away from the center of the valve towards a distal end of the cylindrical portion. In this way, the sidewall of the third circumferential region defined by the outer surface and the inner surface is tapered on both surfaces and narrows towards the distal end of the cylindrical portion.

A further example of valve can have protruding ribs. The valve can have a cylindrical portion and a central portion, which can be referred to as a valve disk, at a first end. Four interior ribs can protrude from an inner surface of the central portion.

The four interior ribs can be spaced equidistantly from each other in a concentric layout. Each of the interior ribs can be generally wedge shaped, or pie shaped, extending from the interior surface of the cylindrical portion towards the center. The wedge shape of the interior ribs is defined by two inwardly tapering sidewalls and an end wall. The end wall can be radiused concavely.

Alternatively, the sidewalls may be parallel to each other such that the interior ribs can have rectangular shapes rather than wedges. In an exemplary embodiment, the end walls of each of the interior ribs may be radiused concavely such that the arcuate sections define a concentric ring around the center of the central portion. The end walls of the interior ribs may have alternative geometry, such as flat, concave, convex, or obliquely tapered to meet the inner surface.

On an outer surface of the central portion, four exterior ribs protrude from the outer surface. The ribs can be spaced from one another. That is, the ribs do not connect or touch one another. Each of the exterior ribs can have an arrow shape, or a stadium shape with one end converging to a point. The shape of the exterior ribs can be defined by two parallel sides connected by a semi-circle on outer ends and a triangular, arrow on inner ends. The exterior ribs can be inset from the outer perimeter of the valve.

The locations of the four exterior ribs can match and overlay with the locations of the interior ribs when viewed along the axis of the valve. The four slits can be disposed between the ribs and extend through the central portion. The four slits define four flaps configured to be moveable relative to the cylindrical portion of the valve to allow for fluid flow.

At the second end of the valve, there can be a lip. The lip may be uniformly arranged circumferentially. The lip can be formed of opposed and parallel lip sides extending radially inwardly from the cylindrical portion. The lip inner side can be aligned in an axial direction, perpendicular to the parallel lip sides.

The inner surface of the central portion extends at an oblique angle from the cylindrical portion towards the center. The outer surface can extend at a perpendicular angle from the cylindrical portion toward the center. In this way, the central portion tapers down in thickness from the cylindrical portion toward the center.

The four interior ribs may have a substantially uniform thickness on the central portion. As such, a top surface of the interior ribs may be parallel to the inner surface of the central portion. With the varying thickness of the central portion, the distance between the interior ribs to the exterior ribs becomes smaller towards the center of the central portion.

Alternatively, the interior ribs and the exterior ribs each may have a varying thickness that decreases when closer to the center of the valve. Still, the interior ribs and the exterior ribs each may have a varying thickness that increases towards the center of the central portion.

Another exemplary valve can have an interior recess formed by a central portion, which can be referred to as a valve disk, that is located at a first end and offset from the medial plane. The valve can have a cylindrical portion and the central portion.

The outer surface of the central portion can blend into the cylindrical portion with a first fillet region, which can be a strip or a band, and a second fillet region. The first fillet region and the second fillet region can have different fillet radiuses. The first fillet region may have a smaller radius than the second fillet region. The first fillet region and the second fillet region can each have a constant radius, or a varying radius. Alternatively, the first fillet region and the second fillet region can be a singular region having a constant or constantly varying radius fillet.

The outer surface of the central portion has a first portion and a second portion. The first portion can be a flat surface that is the outermost part of the first end of the valve. The second portion can be inset in the first region and includes a sloped portion extending towards the center into the central portion. The second portion can form a cutout in the central portion.

From the first portion, three exterior ribs extend radially inward towards the center of the valve. The exterior ribs have a same thickness as that of the first portion. Each of the exterior ribs can comprise of first sides that are substantially parallel to one another. The exterior ribs can each extend inwardly with a substantially constant width between the first sides. The ribs can each have second sides, which can converge towards a point at an inward most end of the exterior rib.

The exterior ribs can extend radially inward adjacent to the second portion. The second portion thus has a petal like arrangement formed from the first sides and second sides. The second region can further include an outer arcuate side and two radiused corners. Accordingly, the outline of the arcuate side, two radiused cornered, first sides, and second sides delineate the first portion and the second portion 704.

Embodiments can be envisioned where the exterior ribs have alternative geometric shapes, such as a rectangle. The inward most end of the exterior ribs does not have to converge to a point. Alternatively, the first sides of the ribs do not need to be parallel to one another. The first sides may be skewed from one another to converge without second sides.

The inner surface of the central portion has a first portion and a second portion. The first portion can have a flat surface perpendicular to the axial direction of the valve. The second portion can have a first region and a second region. The second region can have a flat surface perpendicular to the axial direction of the valve. Alternatively, the second region can be angled to change the thickness of the valve. The first region can be inset in the second region and includes a sloped portion extending towards the center into the central portion. The first region of the inner surface can overlay with the second portion of the outer surface.

From the first portion, three ribs can extend radially inward towards the center of the valve. The ribs can have a same thickness as that of the first portion. Each of the ribs can comprise of first sides that are substantially parallel to one another. The ribs can each extend inwardly with a substantially constant width between the first sides. The ribs can each have second sides, which converge towards a point at an inward most end of the rib.

The ribs can extend radially inward adjacent to the first region and the second region. The first region thus has a petal like arrangement formed from the first sides and second sides. The first region can further have an outer arcuate side and two radiused corners. Accordingly, the outline of the arcuate side, two radiused cornered, first sides, and second sides can delineate the first portion and the second portion.

Embodiments can be envisioned where the rib has alternative geometric shapes, such as a rectangle. The inward most end of the rib does not have to converge to a point. Alternatively, the first sides of the ribs do not need to be parallel to one another. The first sides may be skewed from one another to converge without second sides.

The first region and the second region can form a cutout in the central portion. The second region can extend from tangentially meeting a first inner circumference and forms a step down from the first portion. The first region can then extend into the central portion from the level of the second region. Alternatively, the second region may be inset from the first inner circumference instead of tangentially contacting the first inner circumference.

In the first region, three slits can be provided through the valve from one side to the other side of the central portion or valve disk. The slits extend radially and connect to a point in the center. The slits define flaps. In the particular example, the three slits provided through the valve define three flaps. The flaps are configured to be moveable relative to the outer perimeter of the valve to allow for fluid flow. The three slits can each extend lengthwise to the edge of the first region. The three slits can each be within the first region. Alternatively, the three slits can each extend lengthwise into the second region.

The inner surface of the cylindrical portion can have a taper. At an inner most part of the inner surface, the first inner circumference can have a first circumference defining a bottom end of the inner surface. Midway along the inner surface, there is a second inner circumference. The second inner circumference can have a circumference larger than a circumference of the first inner circumference, and the inner surface is tapered to bridge the first and second inner circumferences.

At another end of the inner surface is a third inner circumference, the third inner circumference having a circumference larger than the circumference of the second inner circumference. Accordingly, the inner circumference of the cylindrical portion increases from the central portion towards the second end.

In other examples, additional defining circumferences can be used for the inner surface to alter the geometry. Also, varying geometries can be used to bridge the defining circumferences of the inner surface.

Another valve provided herein does not have ribbing. Instead, the inner surface has a first portion and a second portion, wherein the first portion is a concentric ring arranged around the second portion. The second portion is then conical in layout as it tapers towards the center of the central portion.

The outer surface can have a first portion and a second portion, wherein the first portion is a concentric ring arranged around the second portion. The second portion is then conical in layout as it tapers towards the center of the central portion. In view of the present disclosure, such modification to have only ribs on one side of the valve would be readily applicable to any of the valves disclosed herein.

wherein yet another embodiment, a valve is provided wherein the slits are arranged along the thicker sections having the ribs instead of the thinner sections of the valve. The slits can be arranged to extend from the first region of the second portion and extend into the ribs instead of only extending along the thinner first region.

The slits can be arranged to extend from the second portion and extend into the exterior ribs instead of only extending along the thinner second portion. In other examples, the slits of the valves described and shown could have such an arrangement where the slits extend along thicker sections of the valve where the ribs are formed.

Another embodiment of a valve comprises protruding interior ribs and recessed exterior ribs. The valve can have a cylindrical portion and a central portion at a first end.

Four interior ribs can protrude from an inner surface of the central portion, which may be called a valve disk. The four interior ribs can be spaced equidistantly from each other in a concentric layout. Each of the interior ribs can be generally arrow shaped extending from the interior surface of the cylindrical portion towards the center. The arrow shape of the interior ribs can be defined by two parallel side edges and two converging sidewalls.

Each of the interior ribs can have a cross sectional shape defined by a minor arc extending from the inner surface across the side edges. The converging sidewalls can each be defined by a converging line, a length along the inner surface, and an arcuate length from the minor arc. Alternatively, the sidewalls may be skewed to each other such that the interior ribs have wedge shapes. The ribs may have alternative geometry, such as flat, concave, or obliquely tapered.

On an outer surface of the central portion, there is formed a void having a cross shaped portion and a conical void portion. The cross shaped portion can comprise two grooves arranged in a cross shaped pattern extending into the valve from the outer surface. The grooves can have sidewalls that are perpendicular to the outer surface. The sidewalls are parallel to one another.

The conical void portion is arranged concentrically around a center of the valve. The conical void portion can include two concentrically arranged portions, a first conical void portion and a second conical void portion. The first conical void portion can be the innermost area. It has a depth into the outer surface that is less than a depth of the grooves.

The second conical void portion can have a taper and a surface partially bridging the outer surface and the first conical void portion. There can be an additional vertical sidewall to bridge the second conical void portion and the first conical void portion. The second conical void portion can be arranged around the first conical void portion. A diameter of the second conical void portion can be less than a length of the grooves.

Alternatively, additional voids can be created, such as a star shaped pattern instead of a cross, by adding one additional channel. Also, additional concentric areas can be arranged for conical void portion.

Slits can be provided across the length of the grooves and extend through the valve from the proximal side to the distal side. The slits can extend radially and connect to a point in the center. The slits can define flaps. In the particular example, the four slits provided through the valve define four flaps.

The flaps are configured to be moveable relative to the cylindrical portion of the valve to allow for fluid flow.

The grooves define the deepest void from the outer surface. The conical void portion removes additional periphery material from the central portion around the grooves.

An additional valve embodiment can comprise chamfering and filleting applied to various geometries. The first end of the valve can have a first portion and a second portion, the first portion can be arranged around the outside of the second portion. The first portion is a first surface. The second portion can form a void, or recess, extending into the first surface.

The second portion can have a first region set at a substantially constant depth into the central portion, and a second region having a varying depth. The second region can be located radially outward from the first region near an outer perimeter. The first region can have a surface substantially parallel to a surface of the first portion. The second region can have a surface bridging the surface of the first region and the first portion.

From the first portion, three ribs extend radially inward towards the center of the valve. The ribs can have a same depth as that of the first surface. Each of the ribs can comprise first edges that are substantially parallel to one another. The ribs can each extend inwardly with a substantially constant width between the first edges. The ribs each have second edges, which can converge toward a point at an inward most end of the rib.

The ribs can extend radially inward adjacent to the first region and the second region. The second portion thus has a petal like arrangement formed from the first edges and second edges. The second region further has an outer arcuate edge and two radiused corners. Accordingly, the outline of the arcuate edge, two radiused cornered, first edges, and second edges delineate the first portion and the second portion. The surfaces bridging the arcuate edge, two radiused cornered, and the first edges to the first region are chamfered, such that they are inclined relative to the first surface.

The cylindrical portion of the valve can have a first cylindrical region, which can transition to a fillet region and then to a conical portion at the second end. The second end can have a sidewall end surface, which has a radially inward extending lip.

The lip can have inwardly tapering sidewalls. On an interior of the lip can be a cavity. On the second surface of the central portion of the valve, interior ribs can be provided in the cavity. The interior ribs can be dimensioned differently from the ribs.

The interior ribs can be generally overlaid in the same position as the ribs inside the valve, such that slits can extend between adjacent ribs in thin areas of the central portion. Top edges of the interior ribs may be filleted or radiused. While a chamfer or a fillet is shown in specific areas of the valve, a fillet or radiusing could also be applied in place of the chamfer, and vice versa.

Yet another embodiment of a valve can be an externally ribbed valve. The structure of the ribs and central portion are similar to other valves described herein with a few exceptions as further discussed below. The cylindrical portion has a first circumferential region and a second circumferential region.

An outer surface can have external ribbing. The external ribbing can vent air or gas but restrict or limit blood flow from flowing thereacross. Alternatively, the external ribbing can form multiple sealing sections with the interior surface of the catheter hub to prevent both gas and fluid flow from flowing thereacross. Also, the second end can have a sidewall end surface with a lip defining a void to the opening of an interior of the valve. The lip can have two inwardly tapering sidewalls.

The first circumferential region can be on a first side of the central portion. The outer surface of the first circumferential region may be tapered inwardly towards the center of the valve towards a distal end of the cylindrical portion. The inner surface of the first circumferential region may be tapered outwardly away from the center of the valve towards a distal end of the cylindrical portion. In this way, the sidewall of the first circumferential region defined by the outer surface and the inner surface is tapered on both surfaces and narrows towards the distal end of the cylindrical portion. The first circumferential portion has a smaller diameter than the outer diameter of the second circumferential region.

The second circumferential region can extend from the central portion in a direction opposite to the first circumferential region. The second circumferential region has a thicker sidewall than the sidewall of the first circumferential region, having an outer surface with a diameter later than the outer surface and an inner surface with a diameter smaller than the inner surface. The outer surface can have ribbing in a sawtooth pattern when viewed from a cross-section of a valve. The sawtooth pattern can be asymmetrical or symmetrical.

Although the valve shown has radial ribs, the circumferential ribs may be axial and extend from one end to the other end of the valve.

In another example, the ribs of the valve are not overlaid, but are rather offset from one another. The ribs on the first surface may be oriented offset from the ribs of the second surface. As such, a view of the cross section of the valve will show that the first surface and the second surface are different. For example, the ribs on one surface may be rotated 180 degrees from the other surface. Alternatively, different numbers of ribs may be used on the opposed sides. The thickness of the ribs on the opposed sides of the valve may be different. In this case, the central portion can be offset from the medial plane.

In another example, the valve can have three generally tear-drop shaped recesses having sloping surfaces, which also resemble a three-leaf clover. The three tear-drop shaped recesses can be coupled to each other at an inner area near the center. Each tear drop can have an enlarged end and a relatively smaller end. The three smaller ends of the three tear-drop shaped recesses can couple to one another at the relatively smaller ends. In other examples, there can be more than three tear-drop shaped recesses.

The tear-drop shaped recesses can gradually thin towards the center of the valve. The outer part of the valve can have a greater thickness than the gradually thinning valve.

The tear drop shaped recesses can each comprise an outer side region having a flatter curve than the arcuate side of FIG. 2A and tapering sides compared to the sides of the recess of FIG. 2A.

In an example, the sloped recesses of the present embodiment each comprises surface with a single slope instead of two or more distinct slope sections. In other examples, towards the center, the three tear-drop shaped recesses can have a generally flat area or a region with essentially zero slope.

Slits are provided through the valve in the tear-drop shaped recesses, thus forming flaps. There can be one or more slits, such as three slits, forming two or more flaps. In some examples, a slit can be provided through each tear drop shaped recess. Each slit can extend from the relatively smaller end and partially along a length of each tear drop shaped recess. In some examples, each slit can extend through the thickness of the valve at a first region but not at a second region. Ribs can be defined by the sides of the tear-drop shaped recesses. The sloping surface of the tear-drop shaped recesses may be a constant slope from the first surface to the center or can be a complex slope or a variable slope.

In a further valve embodiment, a raised portion is provided with a raised perimeter and three raised ribs above the tear-drop shaped recesses. The raised ribs can have a uniform thickness, and accordingly can be angled towards the center due to the thinning tear-drop shaped recesses. The tip of each rib can be pointed, rounded, or blunt. In some examples, the ribs can have the same thickness as the thickness of the valve along the outer periphery of the valve.

In a further valve embodiment, a secondary rib is formed on a rib. The valve can have secondary ribs on top of the ribs.

The secondary ribs can be inset over the ribs, protruding above the first surface. The secondary ribs generally have an arrow shape, defined by two side walls, two converging walls, and a rear wall. The two side walls can be parallel to each other and parallel to the first sides of the respective rib that the secondary rib is located on. The rear wall can be approximately located by the circumference of a circle taken around all of the outer arcuate sides of the second region of the second portion.

An opposite side of the valve can be without the secondary ribs. However, the secondary ribs could be applied to both sides in addition to being on either side of the valve.

The secondary ribs can have filleted edges along the top and bottom. However, various edge finishes may be used as would be appropriate.

In some valve embodiments, the dimensioning of the ribs on the first surface and the second surface are different, resulting in an asymmetrical valve.

A first dimensioning of the ribs can be on the first surface of the valve.

Generally, the second surface can have exterior ribs, opposed to the ribs on the first surface. The innermost location of the ribs can be indicated with the dotted circle as shown. As drawn, the circle of the second surface can be larger in diameter than the circle of the first surface.

A valve actuator configured to actuate a valve can include an actuator head and an actuator leg. The actuator head can have a distal end having a distal end diameter, a proximal end having a proximal end diameter, and a head length. In embodiments, the proximal end diameter is also a maximum diameter, or greatest diameter of the actuator. The distal end diameter is smaller than the proximal end diameter. The head can have a single or simple slope. In other examples, the slope can be a complex slope. Additionally, flanges, grooves, and other surface features can be included to operate with a one-time use valve and/or to engage a shoulder.

A first position of the valve where the valve can be in a closed position with the valve actuator contacting the valve without deforming the valve. A first line representing the line of contact between the actuator head and distal ends of the ribs. In other examples, the actuator head can be spaced from the valve in the first position.

A second position of the valve can be where the valve is in an opened position with the valve actuator contacting the valve and deforming the valve by pushing on the ribs and deflecting the flaps. A second line can represent the line of contact between the actuator head and distal ends of the ribs in the opened position. The distance between the first line and the second line can be the rib travel distance.

A valve can have an area of reduced thickness. This area of reduced thickness can be understood as a portion of the area of the second portion of a valve where the thickness is less than the ribbed portion of the valve. The area of reduced thickness may be a circular area bounded by distal ends of the ribs. In embodiments, the diameter of the area of reduced thickness can be equal to or less than the maximum diameter of the actuator head. In embodiments, the diameter of the area of reduced thickness is equal to or less than the actuator distal end diameter. In embodiments, the diameter of the area of reduced thickness is equal to or greater than the diameter of the needle shaft.

In another embodiment, the valve can have a substantially flat second portion for use with a catheter assembly described elsewhere herein. A plurality of ribs can project from the substantially flat second portion. The ribs can be defined generally by two parallel sides extending radially inward and an arcuate end side near the center of the valve. The sides can have substantially uniform thicknesses. The end side opposite the arcuate end side of each rib can be common or coincident with the outer perimeter of the valve.

The slits can extend through the valve in the second portion, between the ribs. In this way, three corresponding flaps are formed by the three slits, the flaps being configured to be moveable relative to the outer perimeter of the valve to allow for fluid flow. The valve can have similar surface features about the medial plane of the valve. Alternatively, the slits can extend into the ribs from the second portion.

Another embodiment shows a valve can have a cross shaped pattern formed by the recesses of the second portion and useable in a catheter assembly described elsewhere herein. The second portion can be substantially flat. From a first portion, four ribs can extend radially inward towards the center of the valve. The ribs can have a same thickness as that of the first portion. Each of the ribs can comprise of first sides that are substantially parallel to one another. The ribs can each extend inwardly with a substantially constant width between the first sides. The ribs can each have second sides, which can converge towards a point at an inward most end of the rib.

The ribs extend radially inward adjacent to the second portion. The second portion can therefore have a cross like arrangement formed from the first sides and second sides. The second portion can have an outer arcuate side and two corners. Accordingly, the outline of the arcuate side, two cornered, first sides, and second sides can delineate the first portion and the second portion. The outline can be of a substantially uniform thickness or width from the first portion to the second portion.

The second portion can resemble four funnel shaped recess sections joined to one another along or near the center of the valve. Each funnel shaped recess can have an outer arcuate end wall and two sidewalls that taper with each side wall having a generally straight edge. The ribs extending above or projecting beyond the surface of the second portion can be generally constant.

A plurality of slits, such as four slits, can extend through the valve in the second portion, between the ribs. In this way, four corresponding flaps are formed, the flaps being configured to be moveable relative to the outer perimeter of the valve to allow for fluid flow. Alternatively, the slits can extend into the ribs from the second portion.

Embodiments of the present disclosure with the rib joined to the outer or peripheral border of the valve can help to prevent the actuator head from getting stuck in the open position when the actuator is used to open the valve. Additionally, joining the rib to the outer or peripheral border of the valve can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

In addition to catheter apparatuses and needle devices and their components described herein, methods of making and methods of using the catheter apparatuses and needle devices as well as components thereof are understood to be within the scope of the present invention.

Aspects of the present invention comprise a catheter assembly comprising a catheter hub, a needle hub, and a valve having a thickness located inside the catheter hub, the valve comprising: a first surface having a first portion; an opposed second surface, the first surface and the second surface defining a thickness of the valve; a second portion recessed into the first surface; and a slit extending through the thickness of the valve at the second portion; wherein a rib projects along the first surface through an outer boundary of the second portion.

The first surface of the valve can be a planar surface.

The second portion can comprise a first region having a recessed planar surface.

The valve can be disc-shaped. The first surface can be circular. The second portion can be disposed over a central area of the first surface. The rib can be arranged to project in a radial direction.

The second portion can further comprise a second region having a sloped surface bridging the first surface and the first region.

The valve can further comprise a second rib and a third rib projecting along the first surface; and the first rib, the second rib, and the third rib can be arranged in a spaced concentric orientation, each of the ribs oriented to project in a radial direction towards a center of the valve.

A diameter of a first area of the first region that is located concentrically within a distal end of the ribs can be equal to or less than a maximum diameter of an actuator head configured to actuate the valve.

A diameter of a first area of the first region that is located concentrically within a distal end of the ribs can be equal to or less than a diameter of a distal end of an actuator head configured to actuate the valve.

A diameter of a first area of the first region that is located concentrically within a distal end of the ribs can be equal to or greater than a diameter of a needle shaft of a catheter assembly.

The catheter assembly can further comprising a valve actuator slidingly disposed in the catheter hub to actuate the valve, the valve actuator comprising a distal end section having a tapered end for pushing the valve to open the slit of the valve and a plunger end having a plunger element extending proximally of the distal end section; the plunger element being sufficiently rigid to transfer a distally directed force to the distal end section to push the valve to open the slit; and wherein a length of the distal end section of a valve actuator is equal to or greater than a distance that an inward distal end of the first rib is deflected in an axial direction of the valve when a valve actuator actuates the valve.

A further aspect of the present disclosure can include a catheter assembly comprising a catheter hub, a needle hub, and a valve having a thickness located inside the catheter hub for controlling fluid flow, the valve comprising: a first surface having a first portion; an opposed second surface having a first portion, the first surface and the second surface defining a thickness of the valve; a second portion recessed into the first surface at a central location of the first surface; a second portion recessed into the second surface at a central location of the second surface; and a slit extending through the thickness of the valve; wherein a rib extends along the first surface from an outer periphery inward towards the central location of the first surface.

The valve can further comprise a second rib and a third rib projecting along the first surface; and the first rib, the second rib, and the third rib can be arranged in a spaced concentric orientation, each of the ribs oriented to project in a radial direction towards a center of the valve.

The second portion can comprise a recessed planar surface.

The valve can be disc-shaped and the first surface can be circular.

Yet another aspect of the present disclosure includes a catheter assembly comprising: a catheter hub comprising an interior cavity, an opening at a proximal end, and a catheter tube attached thereto and extending from a distal end; a needle having a needle shaft defining a needle axis projecting distally of an end of a needle hub said needle projecting through the catheter tube and comprising a needle tip; a valve having a thickness sized and shaped to obstruct fluid flow positioned inside the interior cavity of the catheter hub, the valve comprising a first surface having a first portion, an opposed second surface having a first portion, a second portion recessed into the first surface at a central location of the first surface, a second portion recessed into the second surface at central location of the second surface, and a slit extending through the thickness of the valve, wherein a rib extends along the first surface from an outer periphery inward towards the central location of the first surface; a valve actuator slidingly disposed in the catheter hub to actuate the valve, the valve actuator comprising a distal end section having a tapered end for pushing the valve to open the slit of the valve and a plunger end having a plunger element extending proximally of the distal end section; the plunger element being sufficiently rigid to transfer a distally directed force to the distal end section to push the valve to open the slit.

The valve can further comprise a second rib and a third rib projecting along the first surface; and the first rib, the second rib, and the third rib can be arranged in a spaced concentric orientation, each of the ribs oriented to project in a radial direction towards a center of the valve.

A length of the distal end section of the valve actuator can be equal to or greater than a distance that an inward distal end of the first rib is deflected in an axial direction of the valve when the valve actuator actuates the valve.

An aspect of the present disclosure includes a method of assembling a catheter assembly having a catheter hub, a needle hub, and a valve having a thickness located inside the catheter hub for controlling fluid flow, the method comprising positioning a valve inside an interior cavity of the catheter hub, the valve comprising a first surface having a first portion; an opposed second surface, the first surface and the second surface defining a thickness of the valve; a second portion recessed into the first surface at a central location of the first surface; and a slit extending through the thickness of the valve at the second portion; wherein a rib extends along the first surface from an outer periphery inward towards the central location of the first surface; and coupling the needle hub with the valve and the catheter hub.

The method can further include wherein the valve further comprises a second rib and a third rib projecting along the first surface; and the first rib, the second rib, and the third rib being arranged in a spaced concentric orientation, each of the ribs oriented to project in a radial direction towards a center of the valve.

The method can also include wherein the first surface is a planar surface.

The method can further provide wherein the second portion comprises of a first region having a recessed planar surface.

The method can include wherein the valve is disc-shaped; and the first surface is circular.

The method can include wherein a diameter of a first area of the first region that is located concentrically within a distal end of the ribs is equal to or less than a maximum diameter of an actuator head configured to actuate the valve.

The method can include wherein a diameter of a first area of the first region that is located concentrically within a distal end of the ribs is equal to or less than a diameter of a distal end of an actuator head configured to actuate the valve.

The method can include wherein a diameter of a first area of the first region that is located concentrically within a distal end of the ribs is equal to or greater than a diameter of a needle shaft of the catheter assembly.

BRIEF DESCRIPTION OF THE DRAWINGS

These and other features and advantages of the present devices, systems, and methods will become appreciated as the same becomes better understood with reference to the specification, claims and appended drawings wherein:

FIGS. 1A and 1B show a cross sectional side view of one embodiment of a valved catheter assembly in the ready position and in an open position;

FIGS. 2A and 2B show a valve having first and second portions, where the second portion has a thickness less than the first portion.

FIGS. 4A and 4B show a valve with a central portion located in-between an outer cylindrical portion.

FIGS. 8A and 8B show a valve where one of the sides of the valve does not have ribbing.

FIGS. 10A, 10B, and 10C show a valve having protruding interior ribs and recessed exterior ribs.

FIGS. 13A, 13B, and 13C show a valve where the ribs of the valve are not overlaid, but are rather offset from one another.

FIGS. 17A and 17B show a valve actuator configured to actuate the valve.

FIGS. 18A and 18B show contact between the valve actuator and the valve.

DETAILED DESCRIPTION

Figure 3B:
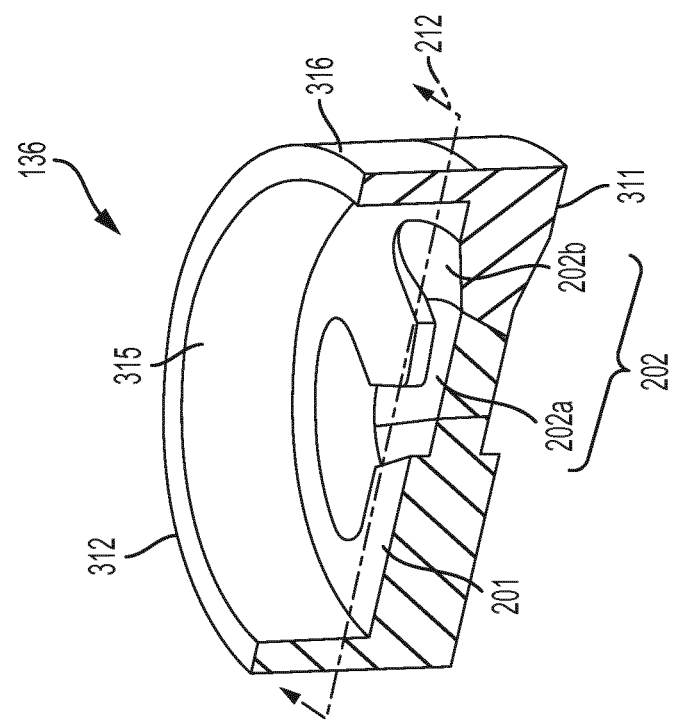
FIGS. 3A and 3B show a valve that is asymmetrical across a medial plane.

The detailed description set forth below in connection with the appended drawings is intended as a description of the presently preferred embodiments of access valves and valved catheter assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

FIG. 1A shows an embodiment of an IV catheter assembly 100 with a valve having a catheter hub 2, which in the embodiment shown has a two-part hub body. Further information regarding the catheter assembly 100 having the valve is discussed in U.S. Pat. No. 9,114,231, the contents of which are expressly incorporated herein by reference. In other examples, a ported catheter assembly or an integrated catheter assembly having an integrated tubing can be practiced with the valve and valve opener described herein.

A distal hub element or first hub part 3 of the catheter hub has a holding section 3a, such as a nose section, in which a catheter tube 4 is held, such as with a metal bushing. The proximal end of the first hub element or part 3 has an enlarged diameter relative to the nose section of the distal end portion and forms a connecting section for connecting with a rear hub element or second hub part 5. The two-part hub configuration can facilitate assembly of a valve and a valve opener, as further discussed below. However, catheter assemblies described herein are not limited to a two-part hub as a singularly formed hub or three or more hub parts may be used to form a catheter hub without deviating from the scope of the catheter assemblies described herein.

The distal end of the rear hub part 5 overlaps the proximal end of the front or first hub part 3 and which is provided at its proximal end with a female Luer fitting and exterior threads 6, forming a female threaded Luer. In some examples, the threads can be omitted and the proximal opening can function as a female Luer slip. Between the two hub parts 3 and 5, a valve 7 in the form of a check valve shaped as a cylinder with a valve disk, valve disc, or a valve disk without a skirt is inserted and is fixed in place by the two hub elements 3 and 5. In other embodiments, a single hub body is used, such as hub 3 only, and the valve 7 is held in place by placing the valve next to or against a shoulder in the interior of the hub element 3. A second shoulder may be incorporated to secure the valve in place with adhesive or bonding being optional. In still yet other examples, a single catheter hub body is used with internal shoulders or undercuts incorporated for retaining the valve 7 therein, without adhesive or bonding. In still another embodiment of the present disclosure, the valve is held in the catheter hub by an interference fit.

In the ready position of FIG. 1A, a nose section of a needle hub 8 is inserted into the catheter hub 2. A hollow needle 9 is fixed to the nose section and extends through the valve 7, the catheter hub 2, and the catheter tube 4 so that the needle tip 9a is exposed beyond the tapered end of the catheter tube 4. Between the needle hub 8 and the valve 7 and inside the catheter hub 2, a valve opening device, valve actuator, or valve opener 10 with a nose end 10a for opening the valve 7 is slidably or displaceably arranged, as shown in FIG. 1B, which is shown pushed in a distal direction by a syringe 14. In an example, the nose end 10a of the valve opener has a truncated cone-shaped locating section or a tapered section. In other examples, the valve actuator 10 has a nose section with a radiused tip, a square tip, or a tip with angular surfaces.

On the proximal side of the valve actuator 10, a plunger section or pusher end 10b is provided. The plunger section is sized and shaped to be pushed by the male Luer conical fitting of a medical implement, such as a syringe tip or an IV tubing adaptor, to open the valve. The pusher end 10b adjoins the nose end 10a. In an example, the nose section 10a incorporates a groove to facilitate engagement with the valve so that even if the medical implement no longer pushes on the valve actuator 10, the nose section remains engaged with the valve.

As explained above, a typical exchange of elements could be the use of the valve opener 10 in the embodiment of FIGS. 1A and 1B. In one example, there is only a single element or leg forming the pusher end. In another example, two legs with a hollow space therebetween or a gap are provided. The two proximal ends of the two legs can provide a surface to be pushed by the medical implement. The space between the two legs can be sized to receive a needle guard element 13. For example, the needle guard element 13 can be positioned in the space between the two legs. In still other examples, the pusher end is a cylinder having one or more openings through the cylinder to provide space for engagement with a needle guard, which can engage the catheter hub through the one or more openings or engage an edge of each of the openings of the cylinder, if more than one opening.

Exemplary valve opener having two openings for accommodating a needle guard is further discussed below with reference to FIGS. 25A-25C.

In other examples, a third housing having a cavity is positioned between the catheter hub 2 and the needle hub. The needle guard element 13 may be positioned in the cavity of the third housing and the third housing having mechanical features to engage the catheter hub and the needle hub. For example, the third housing can have an extension that contacts the interior or the exterior of the catheter hub to secure the third housing to the catheter hub and/or to prevent early activation of the needle guard. In some examples, the needle guard is omitted and the catheter assemblies only incorporate a valve and a valve opener.

On withdrawal of the hollow needle 9 from the catheter hub 2 following successful venipuncture, a change in profile provided near the needle tip 9a and having the form of a radial projection on the hollow needle, such as by crimping, engages with the outer circumference defining the proximal opening on the rear wall or proximal wall 13c of the needle guard 13 so that the needle guard 13 can be removed from the catheter hub with the needle 9. As the needle tip moves proximal of the two distal walls of the two arms, the two arms move, such as spring or deflect radially to disengage from the interior of the catheter hub. As the arms 13a and 13b of the needle guard move radially, the arms, or the distal walls of the arms, cover the needle tip to prevent unintended needle sticks. In other examples, the change in profile can include a sleeve, a notch, or a material buildup on the shaft of the needle.

Subsequent to removal of the needle following successful venipuncture, the two or more flaps of the valve 7, due to their elastic properties, close the one or more slits through the depth of the valve disk or disc so that no blood or substantially no blood can flow out through the catheter 4. As further discussed below with reference to FIGS. 6 and 7, valves provided herein can include three slits 54 starting from the middle of the valve and extending radially over a short radial distance towards the outer perimeter to form elastic flaps that can be expanded by the hollow needle and closed when the needle is removed. In some examples, the flaps can remain open and engaged with a valve opener, which can be referred to as a one-time use valve.

FIG. 1B shows the insertion of a syringe 14 into the proximal opening of the catheter hub 2 to either inject a fluid, such as medicament, through the catheter hub or draw a sample of a bodily fluid like blood. As shown, the syringe tip 14a of the syringe 14 abuts the pusher end 10b of the valve actuating element 10 and pushes it against the valve 7 so that the nose section 10a of the valve opener advances against the flaps of the valve to open the slits 7a thereby opening the valve so that liquid can flow there-across.

As shown, the nose end 10a of the actuator 10 is inclined. Thus, as the syringe is removed and the forward force on the actuator is removed, the elasticity of the material of the valve 7 is sufficient for the two or more flaps to uncoil and push the actuator in the proximal direction to close the seal 7. The valve 7 therefore automatically closes upon withdraw of the pushing force on the actuator and can be re-used by inserting a male Luer tip into the catheter hub to again advance the valve opener into the valve.

A shoulder 5a is shown in the catheter hub 5 in FIGS. 1A and 1B. The shoulder 5a acts as a proximal stop for the actuator 10 when the flange on the actuator abuts the shoulder, which defines the proximal most position of the flange of the actuator. In other examples, the second hub section may incorporate other structural features, such as a tapered internal cavity, to stop the proximal travel of the actuator.

Also shown in the inner circumference of the bore of the hub element 5 is a second shoulder 5b just proximal of the first shoulder 5a. The two radially outer areas of the spring arms of the needle guard, which may be referred to as elbows between the distal walls and the two elongated sections of the two arms, are configured to abut the second shoulder 5b in the ready position in FIG. 1A. When the needle hub 8 with the hollow needle 9 is removed from the catheter hub 2, the needle guard 13 is held generally stationary by the shoulder 5b until the change in profile, such as a crimp, near the needle tip comes to abut on the rear proximal wall of the needle guard and the needle tip moves proximally of the two distal walls on the needle guard 13. At this point, the two spring arms, which are no longer restrained in the radial direction by the needle, spring inwards to cover the needle tip and separate from the second shoulder 5b, whereupon the needle guard 13 with the hollow needle 9 can be removed from the catheter hub. Further information regarding the needle guard 13 is discussed in U.S. Pat. No. 7,736,339, the contents of which are expressly incorporated herein by reference.

FIGS. 20-25C illustrate additional detail regarding components of the valved catheter assembly. Further information regarding the various aspects are discussed in PCT patent applications PCT/EP2016/069619 and PCT/EP2016/069643, the contents of which are expressly incorporated herein by reference.

Figure 20:
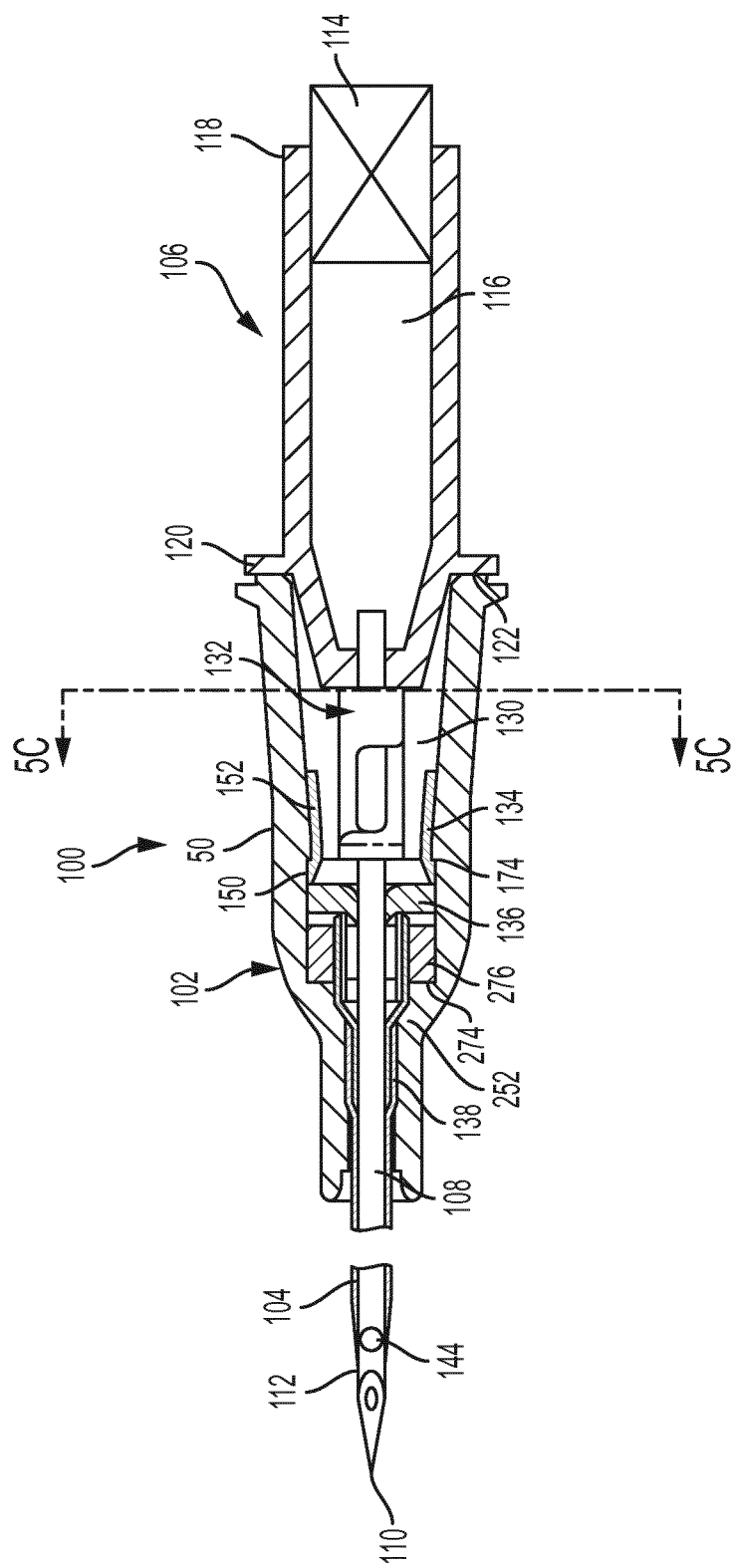
FIG. 20 shows a cross sectional side view of one embodiment of a valved catheter assembly in the ready position.

FIG. 20 is a cross-sectional side view of a needle assembly or catheter assembly 100 in accordance to aspects of the present disclosure. The catheter assembly 100, which may more broadly be referred to as a needle assembly or a needle device, is shown comprising a catheter hub 102 with a catheter tube 104 having a distal opening 112, and a bushing 138 with a distal valve opener 252 and a proximal valve opener or actuator. Aspects of the catheter assembly 100 with the bushing and distal valve opener are disclosed in PCT patent applications PCT/EP2016/069619 and PCT/EP2016/069643. The bushing 138 can be configured to wedge the proximal end of the catheter tube 104 against the interior wall surfaces of the catheter hub 102 to retain the catheter tube 104 to the catheter hub 102 and the distal valve opener 252 can cooperate with the proximal valve opener to open a valve.

Interiorly of the catheter hub 102, a septum or valve 136, a valve actuator 134, such a proximal valve actuator or opener, and a safety clip 132, such as a needle guard or tip protector, are provided. A needle 108 can be inserted through the proximal opening of the catheter hub, with the needle tip protruding out the distal opening 112 of the catheter tube 104. A cannula hub or needle hub 106 can interconnect with the proximal end of the needle 108 and contact the catheter hub 102 in a ready to use position. The proximal opening of the catheter hub 102 is sized and shaped to receive a male medical implement, such as a male Luer tip.

The tip protector 132 located inside the catheter hub and is configured to be removed with the needle 108 following use and the valve 136 and valve actuator 134 remain with the catheter hub 102 for controlling fluid flow therethrough, as previously discussed. As described in in PCT patent application PCT/EP2016/069619 and shown in FIG. 20, the tip protector 132 has a proximal wall with a perimeter defining an opening and two arms extending distally of the proximal wall. One or both arms of the tip protector can have a distal wall for blocking the needle tip in a protective position and both arms can remain on different sides of the needle or the arms can cross the needle axis and intersect when viewed looking at the side of the needle. The actuator 134 is configured to be pushed into the valve 136 to open the valve for fluid flow.

A flash back plug 114 can be provided at the proximal end 118 of the needle hub 106, which allows air to vent but stops blood from spilling out the proximal end 118 when entering the flashback chamber 116 during primary flashback. Alternatively, a syringe can be attached to the proximal end of the needle hub. The valve and actuator described can also be placed within the needle hub as a second valve. The needle hub 106 can comprise a shoulder or other surfaces to physically contact the catheter hub 102, such as the proximal end surface of the catheter hub, to axially register the two hubs 102, 106 to set the length of the needle tip 110 projecting out of the distal opening 112 of the catheter tube 104.

Figure 21A:
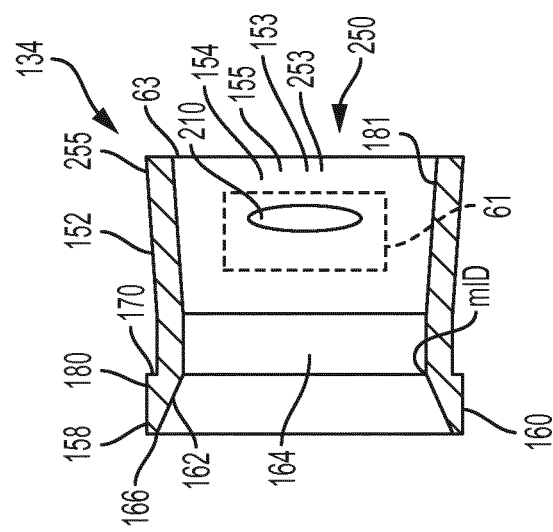
FIGS. 21A and 21B show a cross-sectional view of a valve actuator embodiment and a perspective view of another valve actuator embodiment in accordance with aspects of the present disclosure.
Figure 21B:
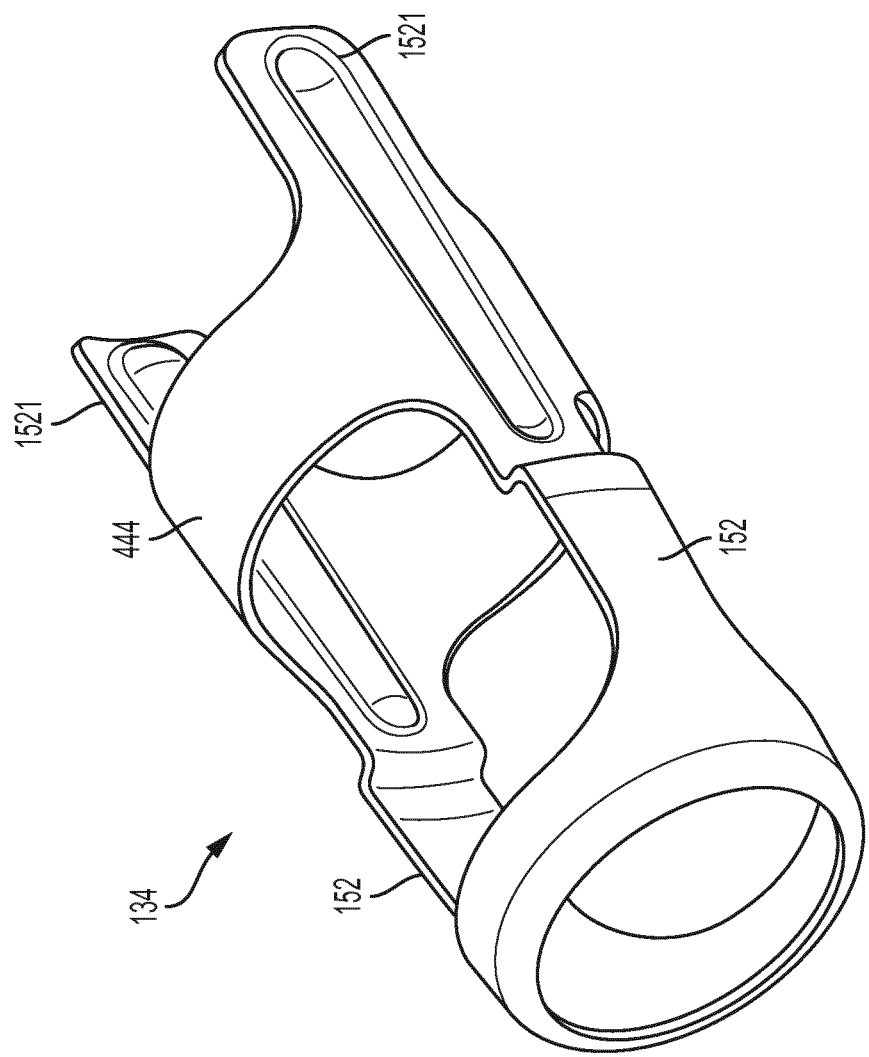

With reference to FIG. 21A and further reference to FIG. 20, the valve opener 134 can comprise a ring or nose section 180 and at least one plunger element 152, such as a leg element or an elongated extension. The nose section or ring 180 is shown in contact with the valve 136 in the needle assembly ready to use position of FIG. 20 but can be slightly spaced from the proximal surface of the valve. In an exemplary embodiment, two plunger elements 152 can extend from the ring or nose section 180 in the proximal direction and each having a length measured in a lengthwise direction of the catheter assembly and a width, measured orthogonally to the length. The at least one plunger element 152 is sized and shaped for contact by a male Luer to transfer a distally directed force from the male Luer to the ring 180 to then open the valve 136. For example, the valve is pushed distally by the proximal valve opener against the distal valve opener, which pushes the valve flaps in the proximal direction to open the slits of the valve for fluid flow.

FIG. 21A shows a cross-sectional side view of the valve opener 134 of FIG. 20. The present valve opener 134 comprises a nose section 180 with an activation end 166 and a plunger end extending in the proximal direction of the nose section 180. However, rather than incorporating two plunger elements 152 with two free ends, the present embodiment incorporates a band or ring connecting the two plunger elements 152 together. The band or ring can comprise two arc-shape, curved sections, or stabilizer elements 253 attached to the two plunger elements 152 to form the band or ring 255. The band 255 can be called a stabilizing ring 255 and can connect the two plunger elements 152 together to form a stabilizing structure. The stabilizing ring 255 forms a continuous perimeter section of the valve actuator that is spaced from another continuous perimeter section defined by the nose section 180 of the valve actuator. In other examples, only a single arc-shape or curved section attaches to the two plunger elements.

The present valve actuator embodiment 134 can also be viewed as a valve opener 134 with a single plunger element 152 extending from a nose section 180 and wherein the single plunger element 152 comprises two or more reliefs or through passages 61 formed through the wall of the plunger end. The needle guard 132 can engage the edges or perimeters 65 of the reliefs 61 in the ready to use position and during retraction of the needle following successful venipuncture. Alternatively, the tip protector or needle guard 132 can project from the holding space defined by the valve opener 134 through the reliefs 61 to engage the interior surface of the catheter hub 102. Still alternatively, the tip protector 132 can project through the reliefs 61 but not contact the interior of the catheter hub or the perimeters 65. Still alternatively, the tip protector 132 can project through the reliefs 61, contacts the interior of the catheter hub, and contacts one or both perimeters of the reliefs. The part of a tip protector that can project through one or both reliefs can be one or two elbows of a tip protector.

The needle guard 132 (FIG. 22) of the present embodiment can be positioned, at least in part, in a holding space 155 of the valve opener 134. When situated in the holding space 155, the needle guard or tip protector can project through one or both reliefs 61 of the valve opener. The part or parts of the needle guard that project through can contact the interior of the catheter hub, be spaced from the interior of the catheter hub, can contact one or both perimeters 65 of the reliefs, or be spaced from one or both perimeters of the reliefs, or combinations thereof. The part of the needle guard that projects can be one or two elbows of a needle guard.

Thus, in the embodiment with two reliefs or through passages 61, the perimeters of the two reliefs or through passages can function as guard engagement sections 210 by allowing the elbows of the tip protector to engage thereto. Alternatively, the two elbows of the needle guard can project through the two reliefs from the holding space defined by the valve opener to engage the guard engagement sections or segments formed on the interior surface of the catheter hub. Thus, the perimeters of the reliefs or the interior surfaces of the catheter hub can form anchor points for the arms of the tip protector to engage thereto in the ready to use position and during refraction of the needle following successful venipuncture.

In an example, the single plunger element 152 of the valve opener 134 of FIG. 21A can embody a generally cylindrical body section 181 having an interior surface 153 defining a bore having a path or channel 154, which can also be a gap for fluid flow, and a proximal perimeter or end edge 63. A guard engagement section 210 can be formed on the interior surface 153 of the present valve opener 134, without reliefs or through passages. In other words, the projection, bump, recess or guard engagement section 210 can be formed on the interior wall surface 153 of the valve opener to allow engagement between the needle guard and the interior surface of the valve opener.

When a valve opener is used with a needle device or catheter assembly 100, such as the assembly of FIG. 1A or FIG. 20, the guard engagement segment 210 can be on the catheter hub, on the interior wall of the valve opener, or a perimeter of a relief formed through the wall of the valve opener. There can be one or more reliefs or guard engagement segments incorporated with the valve opener. There can also be one or more guard engagement segments formed with the catheter hub for use with the one or more reliefs of the valve opener. This allows the two resilient arms of the tip protector 132 to engage the valve opener 134 or to engage the catheter hub by projecting through the reliefs.

Figure 22:
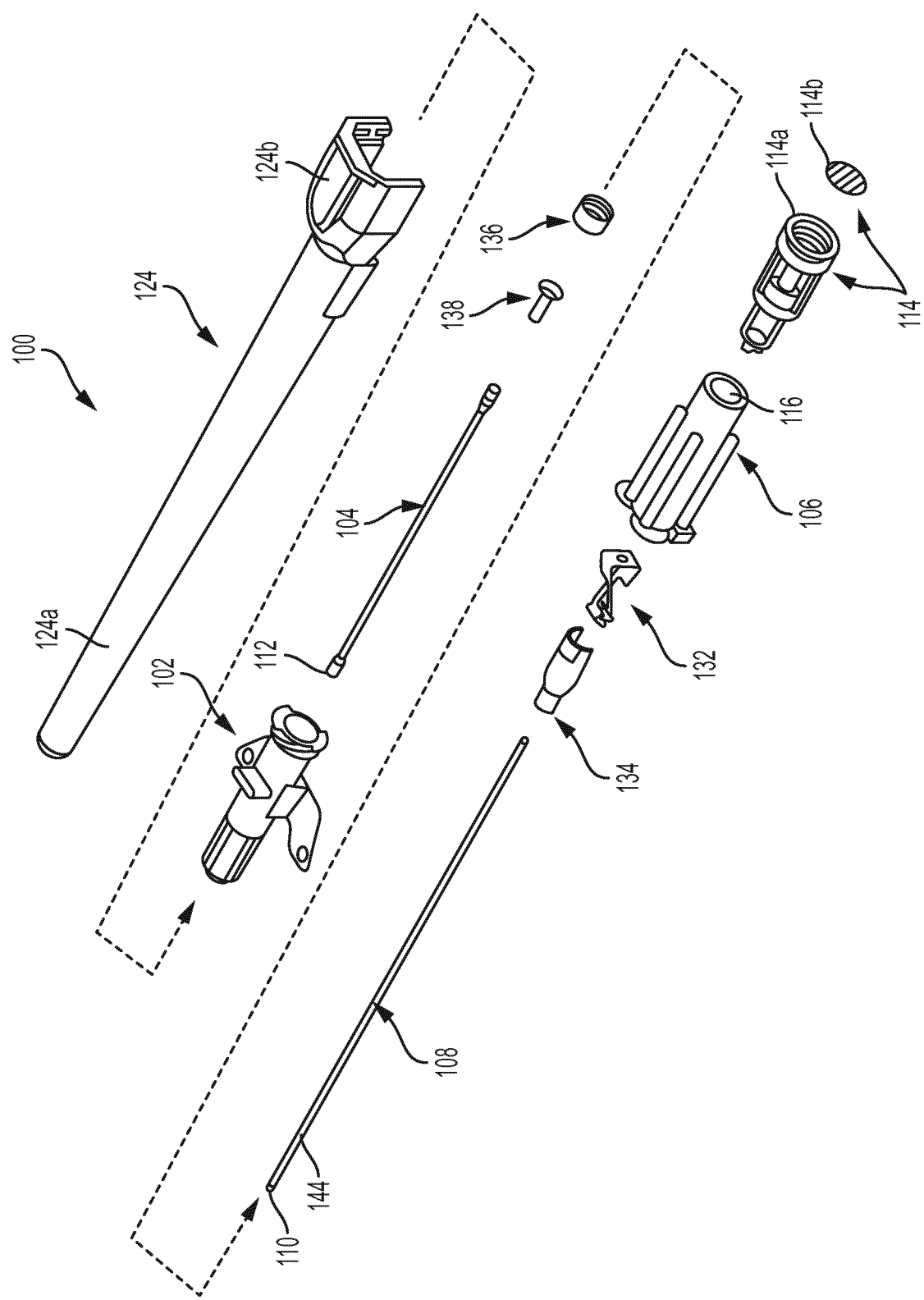
FIG. 22 shows an exploded perspective view of a needle assembly in accordance with aspects of the present disclosure.

FIG. 22 is an exploded perspective top view of a catheter assembly 100 provided in accordance with aspects of the present disclosure. As shown, the catheter assembly 100, which may more broadly be referred to as a needle assembly or a needle device, is shown comprising, a catheter hub 102 with a catheter tube 104 and a bushing 138. The bushing 138 can be configured to wedge the proximal end of the catheter tube 104 against the interior wall surfaces of the catheter hub 102 to retain the catheter tube 104 to the catheter hub 102.

Interiorly of the catheter hub 102, a septum or valve 136, an actuator or valve opener 134 and a safety clip 132, such as a needle guard or tip protector, are provided. A needle 108, which has a change in profile 144, can be inserted through the proximal opening of the catheter hub 102 with the needle tip protruding from the distal opening 112 of the catheter tube in a ready to use position. A cannula hub or needle hub 106 can attach to the proximal end of the needle 108 and can contact the proximal end of the catheter hub 102 when assembled thereto in the ready to use position. The proximal opening of the catheter hub 102 can be sized with a female Luer taper, optionally with external threads, to engage with a male Luer tip in a Luer slip or a Luer lock.

The tip protector 132 is configured to be removed with the needle 108 following use and the valve 136 and valve actuator 134 remain with the catheter hub 102 for controlling fluid flow therethrough. The actuator 134 is configured to be pushed distally by a male tip into the valve 136 to open the valve for fluid flow, as discussed below.

A flash back plug or blood stopper assembly 114 can be connected to the needle hub 106 to stop blood flow out the flashback chamber 116 of the needle hub 106. The flash back plug 114 can be provided at the proximal end the needle hub 106 to allow air to vent but stops blood from spilling out the proximal end of the body of the flash back plug 114, which has a chamber 114a and a hydrophobic filter 114b is assembled in the chamber. Alternatively, a syringe can be attached to the proximal end of the needle hub 106. A second valve 136 and actuator 134 can also be placed within the needle hub 106.

A protective cap 124 with a sleeve 124a and a saddle 124b can be provided to cover the needle 108 during packaging and before use, which is conventional. The saddle 124b can surround at least part of the catheter hub 102 and the needle hub 106 and be removably engaged to the needle hub. The cap 124 should be removed from the needle assembly before use. The catheter hub 102 can be provided with a pair of wings to facilitate securement of the catheter hub to a patient following use.

Figure 23:
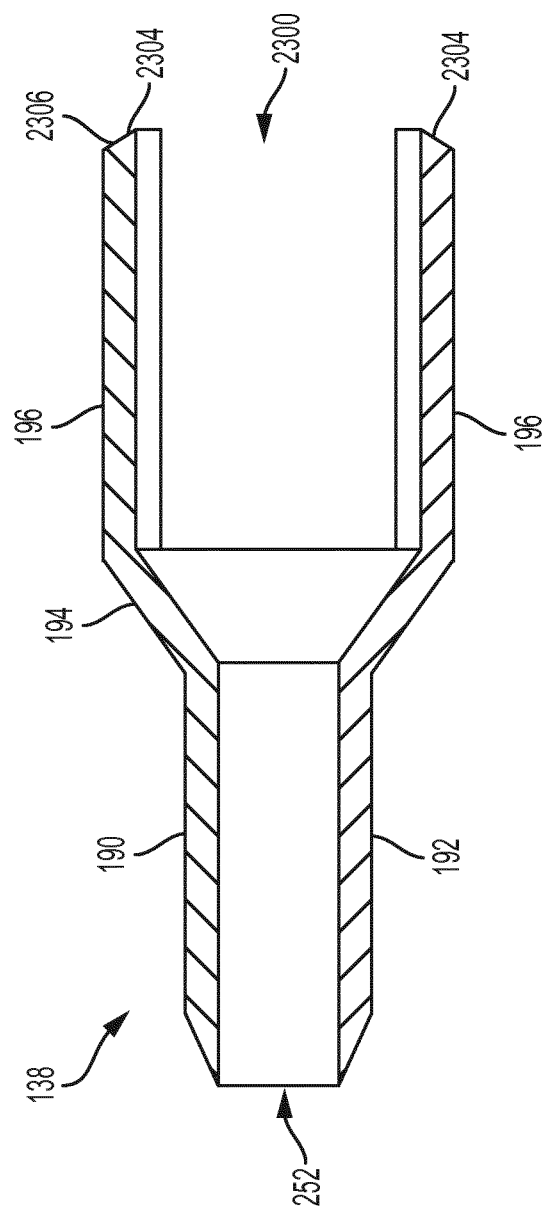
FIG. 23 shows a perspective view of a distal valve actuator embodiment in accordance with aspects of the present disclosure.
Figure 24:
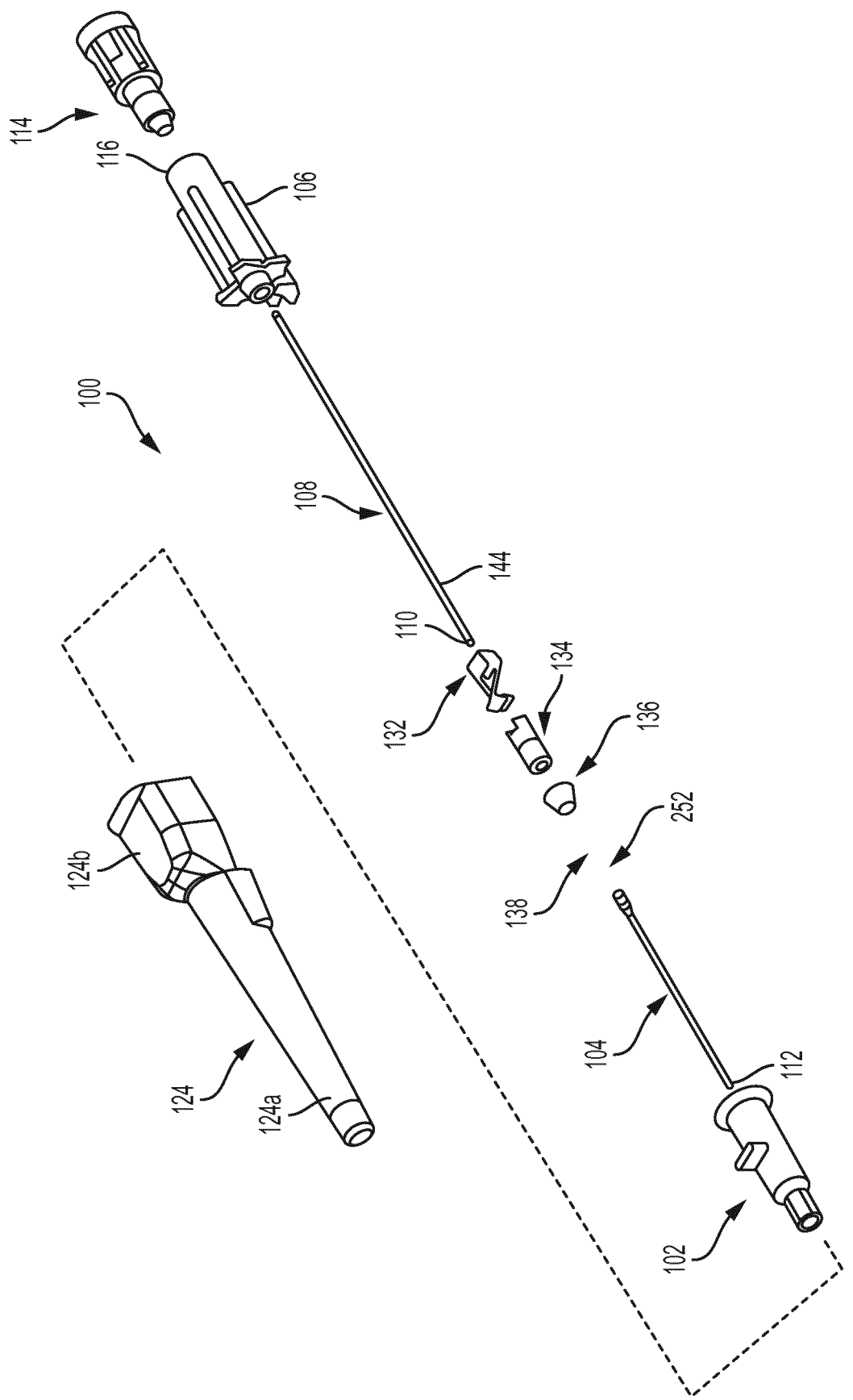
FIG. 24 shows an exploded perspective view of a needle assembly in accordance with aspects of the present disclosure.

FIG. 23 shows a cross-sectional side view of a bushing 138, which can be used to retain a catheter tube to a catheter hub. With further reference to FIGS. 21A and 24, the bushing 138 comprises a body 190 comprising a first body section 192, a second body section 194 extending from the first body section 192, and two or more leg extensions 196 extending from the second body section 194. The first body section 192 can have an elongated body that can have a cylindrical shape with an optional tapered distal tip or nose section. In some examples, a generally cylindrical ring extends from the second body section 194 and the two or more leg extensions 196 extend from the cylindrical ring. One or more gaps 2300 are provided between two adjacent leg extensions 196. In an example, the number of leg extensions 196 incorporated with the bushing 138 is the same as the number of flaps incorporated with the valve 136. Thus, if the valve has three flaps, then there can be three leg extensions 196 on the bushing 138. If the valve 136 has a single slit, then there can be two leg extensions 196. The leg extensions 196 on the bushing 138 can define an outside diameter that is smaller than the minimum inside diameter mID of the valve opener 134.

The proximal tip 2304 of each leg extension 196 can have a chamfer or a blunt tip. In one example, a chamfer 2306 is incorporated at the proximal tip 2304 of each leg extension 196 and wherein the chamfer 2306 tapers inwardly from the exterior of the leg extension 196. This chamfer direction is configured to match the folding direction of the flaps on the valve 136. The bushing 138 can be made from a metal material and the leg extensions 196 can be unitarily formed with the body 190. Alternatively, the leg extensions 196 can be welded to the body 190.

When positioned in the catheter hub 102, the bushing 138 and the valve 136 are oriented so that the leg extensions 196 on the bushing are aligned with the flaps on the valve. In other words, the two components are aligned so that when the valve 136 is advanced distally by the valve opener 134 from the proximal side, as discussed below, the flaps on the valve are pushed into physical contact with the leg extensions 196 on the bushing 138. Thus, if there are three flaps on the valve, the three flaps will be pushed into physical contact with three leg extensions on the bushing. The distally facing wall surface of the valve 136 can touch the leg extensions 196 and/or a resilient element 276 or be spaced from the leg extensions 196 on the bushing 138 and/or the resilient element 276 in the valve closed position and be pushed against the leg extensions during use. In other examples, the valve can touch the proximal tips of the leg extensions and/or the resilient element 276 in the closed position of the valve or be spaced therefrom. If spaced from the leg extensions 196 and/or the resilient element 276, the valve 136 can be displaced axially into contact therewith.

FIG. 24 is an exploded perspective view of a needle assembly or catheter assembly 100 in accordance to aspects of the present disclosure. The catheter assembly 100, which may more broadly be referred to as a needle assembly or a needle device, is shown comprising a catheter hub 102 with a catheter tube 104 having a distal opening 112, and a bushing 138 with a distal valve opener 252. The bushing 138 can be configured to wedge the proximal end of the catheter tube 104 against the interior wall surfaces of the catheter hub 102 to retain the catheter tube 104 to the catheter hub 102.

An aspect of the present disclosure is understood to include a valve opener 134 for opening a valve 136. The valve opener 134 is configured to push the valve against another structure, such as the leg extensions 196 on the bushing 138. The present valve opener 134 may be viewed as having a multi-piece valve opening structure. For example, the part with the ring 180 and the plunger elements 152 may be viewed as a proximal valve opener 250 and the bushing 138 with the leg extensions 196 may be viewed as a distal valve opener 252. The bushing 138 and the distal valve opener 252 can be unitarily formed.

The two valve openers 250, 252 cooperate to open the valve 136. As described, the proximal valve opener 250 is sized and shaped to push against the outer edges of the valve 136 in the distal direction to move the valve against the distal valve opener 252. The distal valve opener 252 is sized and shaped to push the flaps on the valve in a radially outward direction and part of the flaps in a proximal direction to open a fluid path or flow path 226 through the valve 136. In an example, the leg extensions 196 on the distal valve opener 252 are axially fixed and by pushing the flaps of the valve in a distal direction against the leg extensions, the flaps are deflected radially outward by the leg extensions on the distal side of the valve 136. In other words, when the valve is actuated to open a flow path through the valve, the valve is being physically pushed by an actuator on a proximal side of the valve and an actuator on the distal side of the valve. In a particular embodiment, the valve can be actuated to open a flow path through the valve by being physically pushed by a ring on a proximal side of the valve and leg extensions on the distal side of the valve.

Figure 25C:
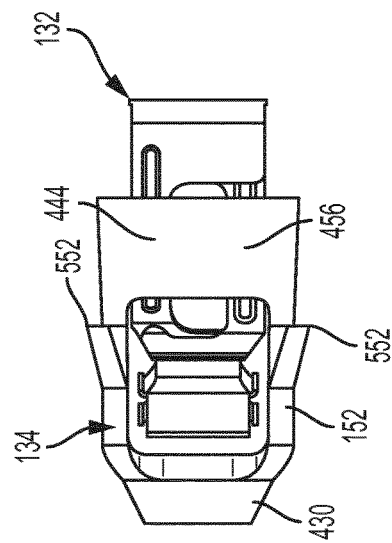
FIGS. 25A, 25B, and 25C show a valve actuator embodiment in accordance with aspects of the present disclosure.
Figure 25B:
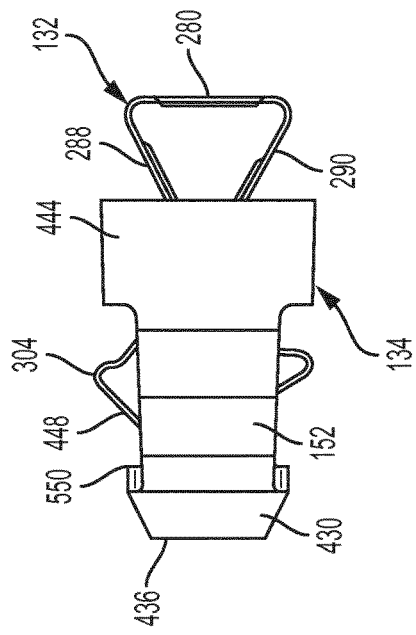
Figure 25A:
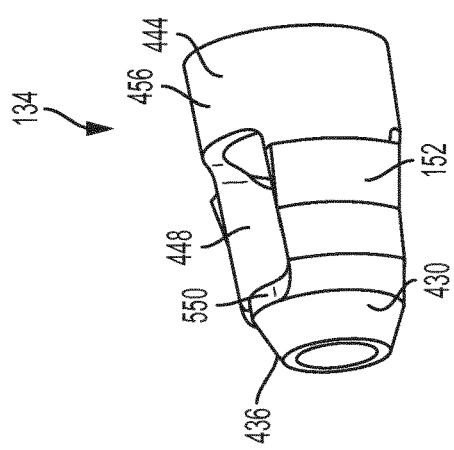

FIG. 25A is a perspective view of a valve actuator 134 embodiment provided in accordance to aspects of the present disclosure. The actuator 134 comprises a generally cylindrical nose or nose section 430, such as a conical frustum shape nose, and an activation end 436 at a distal end thereof. Actuating arms 152 extend lengthwise from the nose section 430. In the ready position and if used with the catheter, the nose section 430 may be in contact with the valve disc or can be slightly spaced from the proximal surface of the valve disc 410.

A relief or through passage 448 provides access for a tip protector 132 to engage with the interior of the catheter hub 102, as previously described. In one embodiment, two through passages or reliefs 448 on opposite sides of the body of the actuator 134 are provided to give access to the interior of the catheter hub 102 to two corresponding arms of a tip protector 132. Other embodiments can have a different number of through passages, such as one, three or more, can be incorporated. For example, there may be three through passages spaced between three actuating elements.

In the illustrated embodiment, the stabilizers 444 connect the two actuating elements 152 and form a ring structure on the proximal end of the actuator 134, also called a stabilizing ring 456. The stabilizers 444 can provide additional rigidity and/or engagement surfaces for the actuator to interact with a needle guard and/or with the interior of the catheter hub 102. In some embodiments, the stabilizing ring 456 comprises one, two, or more individual sections that form a substantially cylindrical section of the actuator body. The stabilizers can have edges that align with each other or may be offset. In still other examples, one or more leg extensions can extend proximally of the stabilizers 444. For examples, two leg extensions can align with the two actuating arms 152 and extend in the proximal direction from the stabilizers 444, as shown with reference to FIG. 21B. The length of the leg extensions that extend from the stabilizers can be selected as appropriate for pushing by a male Luer tip to push the valve opener in the distal direction to open the valve.

FIGS. 25B and 25C illustrate a side and top view of the actuator embodiment 134 of FIG. 25A. A majority of the tip protector 132 is shown fitted inside the holding space of the actuator 134, with a portion of the tip protector extending in the proximal direction past the proximal end of the actuator. For example, the proximal wall 280 and part of the two arms 288, 290 of the tip protector 132 extend radially through the relief 448 of the actuator 134. One or more ribs or projections 552 can be formed on the exterior surface of the actuating arms 152 and can engage with a shoulder of the catheter hub to retain the actuator 134 inside the catheter hub 102 in the ready to use position and used position. Where leg extensions are incorporated, the proximal wall of the needle guard can be even with the proximal end most of the two leg extensions or the proximal end most of the two leg extensions can extend further proximally of the proximal wall.

The present disclosure further relates to valves for use in IV catheters that can prevent blood leakage in multiple access use situations, such as repeated use situations. Exemplary catheter assemblies and components that the valves can be used with are shown in FIGS. 1A, 1B, and 20-25C. An exemplary valve 136 is shown in FIG. 20 and is configured for multiple use with other alternative valves disclosed herein further below. The valve 136 can be opened by a valve opener or actuator on insertion of a Luer connector which can push the valve actuator distally to open the valve. The valve can open with just a proximal valve opener or the valve can be pushed against a distal valve opener to open the valve, as previously described. When the Luer connector is withdrawn, the valve is configured to return to its closed configuration with adequate sealing to substantially limit or prevent blood leaking out through the valve. In some examples, the valve is configured to return due to the elastomeric properties of the valve. As discussed in PCT patent applications PCT/EP2016/069619 and PCT/EP2016/069643, a spring or resilient element can be incorporated to facilitate returning the valve to its closed position where fluid is restricted or stopped from flowing thereacross.

In some examples, a relatively thinner area or cross-sectional profile of the valve around a slit is provided to reduce the drag force between the needle and the valve when the needle is withdrawn and moving against the surfaces of the slit. A single slit can define two flap sections on either side of the slit. Three slits formed through the valve can define three flaps, and so forth. The three slits can converge at a single point, which can define the middle or center of the valve. The thicker area of the valve compared to the relatively thinner area can provide rigidity so that the flaps on the valve defined by the slit are able to return to a closed configuration when the Luer connector is removed, thereby enabling multiple access use. In some examples, the thicker area is provided by incorporating one or more ribs. One advantage to having ribs instead of just increased thickness around the perimeter of the valve is to further reinforce the valve. This can improve the recovery and sealing of the valve for multiple access use.

Embodiments of the present disclosure may aid in reducing drag and deformation of the valve when removing the needle following successful venipuncture.

Generally, the valve 136 is considered as having a proximal side and a distal side, with the proximal side being the side closer to or the side facing the proximal end of the catheter hub, which has the proximal opening that opens to the interior of the catheter hub. However, the orientation of the valve may be reversed as one of ordinary skill might see fit. In some examples, more than one slit can be incorporated with the valve to define more than two flaps.

In some examples, the valves described herein can be used with a catheter assembly having a proximal valve opener for opening the valve located in a catheter hub without a distal valve opener. Exemplary valve assemblies with a proximal valve opener only are disclosed in U.S. Pat. No. 9,114,231 and PCT patent application PCT/EP2016/069619.

FIG. 2A illustrates an exemplary valve 136 in accordance with aspects of the present disclosure, which may be usable with the catheter assemblies and hubs with a female Luer described elsewhere herein. The present valve 136 can have a first portion 201 having a first thickness and a second portion 202 having a second thickness less than the first thickness, measured orthogonal to the medial plane 212. The second portion 202 can have a first region 202a of a substantially constant thickness and a second region 202b having a varying thickness along a cross-section. The thickest part of the second region 202b of the second portion 202 can be larger than the thickest part of the first region 202a. In an example, the first region 202a can be at or near the valve center 209 and the second region 202b of the second portion further away from the valve center 209.

The second region 202b can be located radially outward from the first region 202a near an outer perimeter 207 of the valve. The first region 202a has a surface substantially parallel to a surface of the first portion 201. The surfaces of the first portion 201 and of the first region 202a can be on two different planes. The second region 202b can have a surface bridging the surface of the first region 202a and the first portion 201. The surface of the second region 202b can taper between two different planes.

Embodiments can be envisioned where the surfaces of the first region 202a and the first portion 201 are not parallel to one another. Additionally, although the exemplary valve 136 shows substantially flat surfaces for the valve 136, non-flat surfaces could also be used.

From the first portion 201, three ribs 208 can extend radially inward towards the center 209 of the valve 136. While the ribs 208 are flush with the surface of the first portion 201, the ribs 208 can be defined as a raised or ribbed structure between sections of the second portion 202. The ribs 208 can have a same thickness as that of the first portion 201. In other examples, the ribs 208 can be thicker than that of the first portion 201. Each of the ribs 208 can comprise of first sides 204 that are substantially parallel to one another. The ribs 208 each extend inwardly with a substantially constant width between the first sides 204. The first sides 204 can have a tapering thickness as they extend radially inward, due to the angle of the second region 202b. The ribs 208 each have second sides 205, which converge towards a point 206 at an inward most end of the rib 208. Optionally the second sides 205 of the ribs can be rounded or have blunt ends.

In an example, the tips of each second sides 205 or the ribs 208 define an actuating region. As further discussed below, the actuating region is smaller than the tip of a valve actuator head so that the valve actuator head pushes against the ribs rather than the first region 202a of the second portion 202 during activation of the valve.

The ribs 208 extend radially inward adjacent to the first region 202a and the second region 202b. The second portion 202 thus has a petal like arrangement formed from the first sides 204 and second sides 205. The second region 202b further has an outer arcuate side 203a and two radiused corners 203b. Accordingly, the outline of the arcuate side 203a, two radiused cornered 203b, first sides 204, and second sides 205 delineate the first portion 201 and the second portion 202.

Embodiments can be envisioned where the rib has alternative geometric shapes, such as a rectangle. The inward most end at sides 205 of the rib 208 does not have to converge to a point. Alternatively, the first sides 204 of the ribs 208 do not need to be parallel to one another. The first sides 204 may be skewed from one another to converge without second sides 205.

In the first region 202a, three slits 210 are provided through the valve 136 from the proximal side to the distal side. The slits 210 can extend radially and connect at a point in the center 209. The slits 210 define flaps 211. In the particular example, the three slits 210 can be provided through the valve 136 to define three flaps 211. The flaps 211 are configured to be moveable relative to the outer perimeter 207 of the valve 136 to allow for fluid flow. The three slits 210 can each extend lengthwise to the edge of the second region 202b. The three slits 210 can each be within the first region 202a. Alternatively, the three slits 210 can each extend lengthwise into the second region 202b. The three slits 210 are spaced from the three ribs 208. That is, the slits do not cut into the ribs. In other examples, the slits can cut into the ribs and part of the first region 202a.

The valve 136 can have an outer perimeter that is axially fixed within the interior of the catheter hub. The valve can be opened with just a proximal valve opener. For example, the proximal valve opener can move into the valve by a male Luer tip to deflect one or more flaps on the valve. Any part of a valve can be axially fixed by the interior surface structure of a catheter hub so that the flaps can be pushed relative to the outer portions of the valve. In still other examples, the valve can be actuated to open by a valve assembly having both a proximal valve opener and a distal valve opener. Optionally, the valve can have a cylindrical skirt section extending along the outer perimeter 207 of the valve, as further discussed below with reference to FIGS. 3A and 3B.

FIG. 2B illustrates a cross-sectional view of the valve 136. Along a medial plane 212, the features of valve 136 are symmetrical and reflected on both the first surface 150 and the second surface 151, which can also be referred to as a proximally facing surface and a distally facing surface when the valve is mounted inside a catheter hub. As such, the proximal side and the distal side of the valve 136 are symmetrical. Where the dimensions of the features of the first portion and second portion are the same on both sides of the valve 136, the features may still be rotated around the axial center of the valve 136 relative to the other side of the valve 136, such that the features on the proximal side are offset from the distal side when viewed from a top down orientation along the axial direction of the valve 136. Alternatively, the opposed sides of the valve 136 can have different dimensions for each of the first portion and second portion. For example, the various thicknesses of the ribs 208 and second region 202b of the second portion 202 can be different when comparing the same elements of the proximal side and the distal side. In other embodiments, only one side of the valve 136 can have the geometrical features and the opposed side being generally flat throughout.

The exemplary illustration shows the first portion 201 and the first region 202a having surfaces substantially parallel to the medial plane 212. Embodiments can be envisioned where the surfaces of the first region 202a and the first portion 201 are not parallel to one another or the medial plane 212. The second region 202b has a surface bridging the surface of the first region 202a and the first portion 201. In the exemplary illustration, the second region 202b has a substantially flat surface arranged in a ring shape. Other surface geometries can be used, such as angular step downs or with convex or concave shaped curved surfaces as necessary to bridge the surfaces of the first region 202a and the first portion 201.

The valve 136 may be integrally formed of a single material. Alternatively, the valve 136 may be formed of different materials in various portions of the valve 136 for reasons such as improved rigidity or flexibility. The valve can be made from a medical grade elastomer or a thermoplastic elastomer (TPE).

One advantage of having arrow shaped ribs extending towards the slit is to have earlier contact between the valve opener and the valve upon insertion of a Luer connector before contact with a surface having the slits. Therefore, the relatively earlier contact allows earlier opening of the valve by reducing the travel distance needed by the valve opener to open the valve. Said differently, the girth or thickness provided by the ribs allow the valve to be contacted earlier by a valve opener compared to a similar valve without the disclosed ribs extending further in the proximal direction than the surfaces having the slits. Still further, the relatively thinner area of the valve near the valve center reduces drag on a needle while still allowing for the valve to be actuated earlier and with increased resiliency, due to the presence of the ribs.

There is a possibility of a contact between the tips of the ribs with the needle due to some deflection of the flaps when the needle projects through the slits in a ready to use position. In the event of contact, having an arrow-shaped tip or a reduced tip region for each rib instead of a straight (rectangular) edge tip can help to reduce the contact area between the rib tips and the needle, thereby reducing friction and drag force when the needle is withdrawn.

An advantage of the curved recesses having sloped surface between the thicker valve area and thinner valve area is to ease the molding. There is also a tendency for blood to clot in areas with sharp steps or angles; therefore the curved shape and sloped surface can reduce the risk of blood clot formation.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 3A:
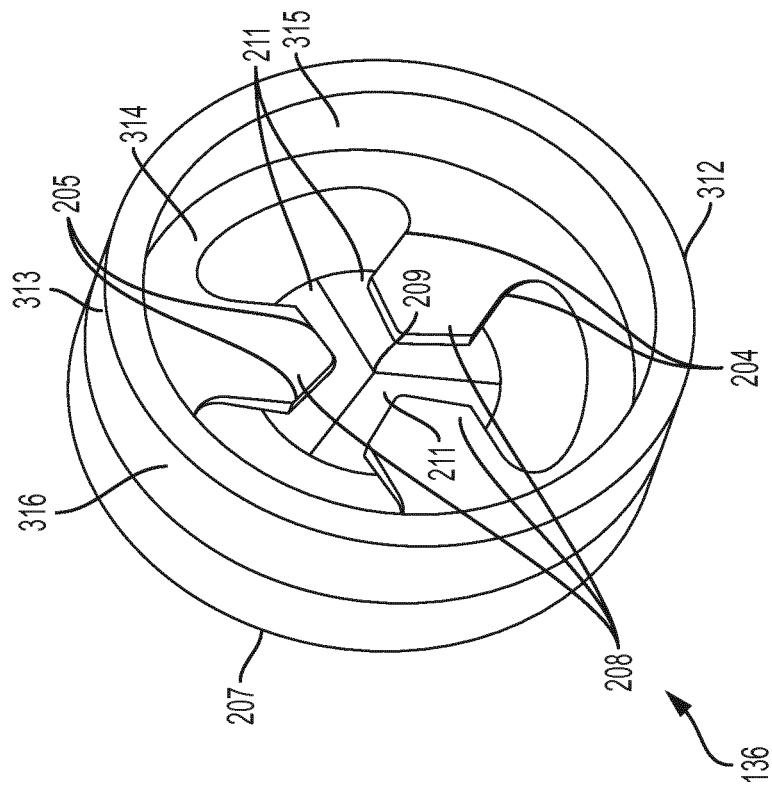

FIGS. 3A and 3B illustrate an exemplary valve 136 of the present disclosure wherein the valve 136 is asymmetrical across a medial plane 212. The valve 136 can have an outer perimeter 207 having a cylindrical portion or skirt 313 with a first end 311 and a second end 312. The cylindrical portion or skirt 313 extending from the valve disk at the first end adds to the overall length of the valve 136. The sidewall of the cylindrical portion 313 defined by the inner surface 315 and the outer surface 316 can have a constant thickness. Inside of the cylindrical portion 313 is a central portion 314, which can be referred to as a valve disk (see FIGS. 2A and 2B for exemplary features). The central portion 314 can include a first portion 201 having a first thickness and a second portion 202 having a second thickness less than the first thickness. Both the first portion 201 and the second portion 202 can have thicknesses less than the cylindrical portion 313. Additionally, the first portion 201 and the second portion 202 can be offset from the medial plane 212 of the valve 136.

The second portion 202 can have a first region 202a of a substantially constant thickness and a second region 202b having a varying thickness. The second region 202b is located radially outward from the first region 202a near an outer perimeter 207. The first region 202a can be a surface substantially parallel to a surface of the first portion 201. The second region 202b can have a surface bridging the surface of the first region 202a and the first portion 201. Embodiments can be envisioned where the surfaces of the first region 202a and the first portion 201 are not parallel to one another. Additionally, although the exemplary valve 136 shows substantially flat surfaces for the valve 136, non-flat surfaces could also be used.

From the first portion 201, three ribs 208 extend radially inward towards the center 209 of the valve 136. The ribs 208 can have a same thickness as that of the first portion 201.

Each of the ribs 208 can comprise of first sides 204 that are substantially parallel to one another. The ribs 208 each extend inwardly with a substantially constant width between the first sides 204. The ribs 208 can each have second sides 205, which converge towards a point 206 at an inward most end of the rib 208. The ribs 208 extend radially inward adjacent to the first region 202a and the second region 202b.

In the first region 202a, three slits 210 are provided through the valve 136 from the proximal side to the distal side. The slits 210 can extend radially and connect to a point in the center 209. The slits 210 define flaps 211 that can deflect to open the valve. In the particular example, the three slits 210 provided through the valve 136 define three flaps 211. The flaps 211 are configured to be moveable relative to the outer perimeter 207 of the valve 136 to allow for fluid flow. The three slits 210 can each extend lengthwise to the edge of the first region 202a. The three slits 210 can each be within the first region 202a. Alternatively, the three slits 210 can each extend lengthwise into the second region 202b.

FIG. 3B illustrates a cross-sectional view of the valve 136. FIG. 3B shows that opposed sides of the central portion 314, which can be referred to as a valve or valve disc, can be geometrically similar to one another. In the illustrated embodiment, the first portion 201 can be integral with an end portion 311 of the cylindrical portion 313. In an embodiment, the end portion 311 is the distal side of the valve as oriented inside the catheter hub. As shown, the central portion 314 is offset in an axial direction from the medial plane 212 of the valve 136 and is at an end portion of the valve 136. Alternatively, the central portion 314 can be inset from the end of the cylindrical portion 313. Still alternatively, the cylindrical portion can be orientated in the proximal direction when located inside the catheter hub.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

FIGS. 4A and 4B illustrate an exemplary valve 136 of the present disclosure wherein the valve 136 has a central portion 314 located in-between an outer cylindrical portion 313. The central portion 314 can be referred to as a valve disk. In this way, the central portion 314 can be positioned as a septum, or partition separating two interior recesses 401, 402 of a cylinder. The central portion 314 can be located between the two ends of the cylindrical portion 313 to define two interior spaces or recesses. The two interior spaces or recesses can be similar in size or can be unequal in size. In an example, the smaller interior space can be positioned distally of the relatively larger space.

FIG. 4A shows the cylindrical portion 313 can add to the overall length of the valve 136. Inside of the cylindrical portion 313, the central portion 314 (see FIGS. 2A and 2B for exemplary features) can include a first portion 201 having a first thickness and a second portion 202 having a second thickness less than the first thickness. Both the first portion 201 and the second portion 202 have thicknesses less than the cylindrical portion 313. Additionally, the first portion 201 and the second portion 202 can be offset from the medial plane 212 of the valve 136.

The second portion 202 has a first region 202a of a substantially constant thickness and a second region 202b having a varying thickness. The second region 202b can be located radially outward from the first region 202a near an outer perimeter 207. The first region 202a can have a surface substantially parallel to a surface of the first portion 201. The second region 202b can have a surface bridging the surface of the first region 202a and the first portion 201. Embodiments can be envisioned where the surfaces of the first region 202a and the first portion 201 are not parallel to one another. Additionally, although the exemplary valve 136 shows substantially flat surfaces for the valve 136, non-flat surfaces could also be used.

From the first portion 201, three ribs 208 extend radially inward towards the center 209 of the valve 136. The ribs 208 can have a same thickness as that of the first portion 201. Each of the ribs 208 comprises of first sides 204 that are substantially parallel to one another. The ribs 208 can each extend inwardly with a substantially constant width between the first sides 204. The ribs 208 each have second sides 205, which converge towards a point 206 at an inward most end of the rib 208. The ribs 208 can extend radially inward adjacent to the first region 202a and the second region 202b.

In the first region 202a, three slits 210 are provided through the valve 136 from the proximal side to the distal side. The slits 210 can extend radially and connect to a point in the center 209. The slits 210 can define flaps 211. In the particular example, the three slits 210 provided through the valve 136 define three flaps 211. The flaps 211 can be configured to be moveable relative to the outer perimeter 207 of the valve 136 to allow for fluid flow. The three slits 210 can each extend lengthwise to the edge of the first region 202a. The three slits 210 can each be within the first region 202a. Alternatively, the three slits 210 can each extend lengthwise into the second region 202b.

Furthermore, as shown in FIG. 4B, the outer cylindrical portion 313 may be a tapered surface 403 on at least one of an exterior surface 404 and an interior surface 405. The surface may taper from approximately where the central portion 314 is located along the cylindrical portion 313 to an end of cylindrical portion 313. In embodiments, both ends of the cylindrical portion 313 may be tapered from approximately where the central portion 314 is located along the cylindrical portion 313 to an end of cylindrical portion 313. This may be for ease of manufacturing and for ease of assembly into an assembly without concern for orientation of the valve 136. In some embodiments, the entire cylindrical portion may be tapered from one end to the other on at least one of the exterior surface 404 and the interior surface 405.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 5B:
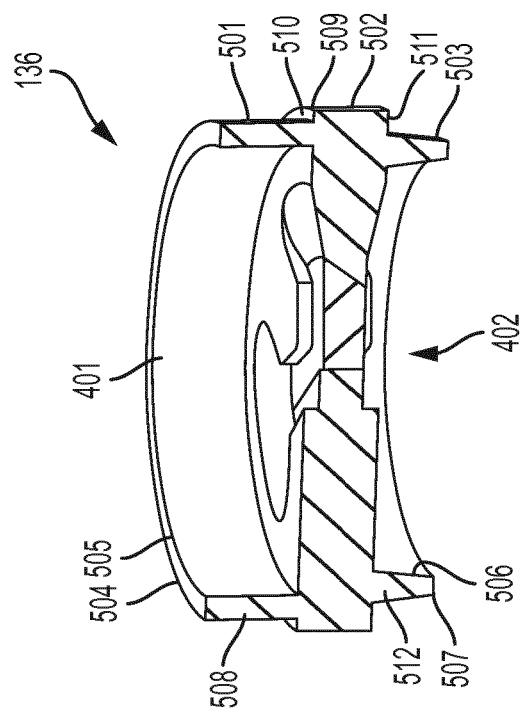
FIGS. 5A and 5B show a valve having differing diameters for the interior recesses.
Figure 5A:
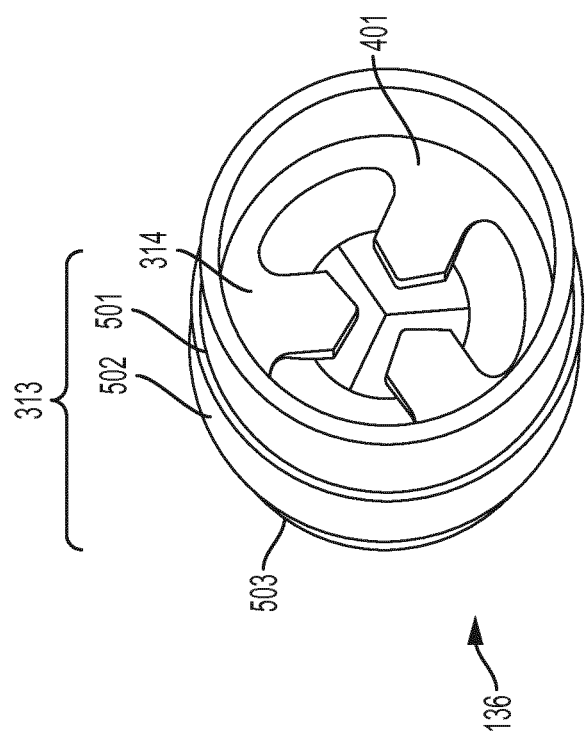

FIGS. 5A and 5B illustrate an exemplary embodiment of a valve 136 (see FIGS. 2A and 2B for exemplary features) having differing diameters for the interior recesses 401, 402. The outer cylindrical portion 313 can have three circumferential regions 501, 502, 503. A diameter of an inner surface 505 of a first circumferential region 501 can be larger than a diameter of an inner surface 506 of the third circumferential region 503. A diameter of an outer surface 504 of the first circumferential region 501 can be larger than a diameter of an outer surface 507 of the third circumferential region 503. A ridge surface 509 of the second circumferential region 502 can have a diameter larger than either of the first circumferential region 501 and the third circumferential region 503.

The inner surface 505 and the outer surface 504 of the first circumferential region 501 can be substantially parallel and define a sidewall 508. The ridge surface 509, as viewed cross-sectionally along the axial direction of the valve 136, is parallel to the outer surface 504 of the first circumferential region 501. The ridge surface 509 of the second circumferential region 502 is projected outwardly from the first circumferential region 501 and the third circumferential region 503 with two ridge side surfaces 510, 511. The second circumferential region 502 can correspond to a thickness of the central portion 314. The ridge side surfaces 510, 511 can be parallel to each other and extend in a radial direction of the valve 136. Alternatively at least one of the ridge side surfaces 510, 511 can extend radially in an angled direction to form a conical surface.

The outer surface 507 of the third circumferential region 503 may be tapered inwardly towards the center 209 of the valve 136 towards a distal end of the cylindrical portion 313. The inner surface 506 of the third circumferential region 503 may be tapered outwardly away from the center 209 of the valve 136 towards a distal end of the cylindrical portion 313. In this way, the sidewall 512 of the third circumferential region 503 defined by the outer surface 507 and the inner surface 506 is tapered on both surfaces and narrows towards the distal end of the cylindrical portion 313.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 6C:
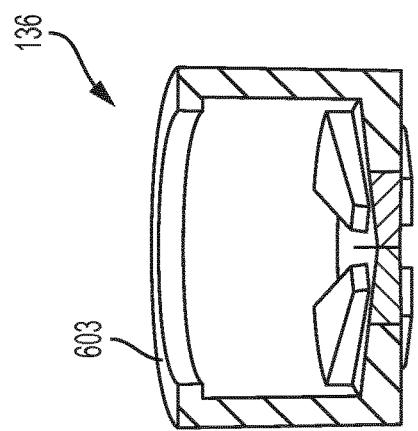
FIGS. 6A, 6B, and 6C show a valve having protruding ribs.
Figure 6B:
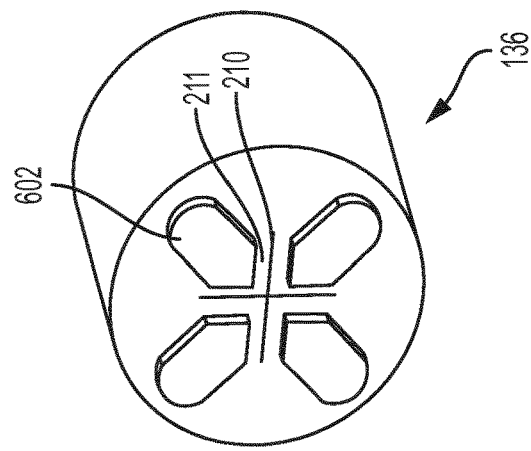
Figure 6A:
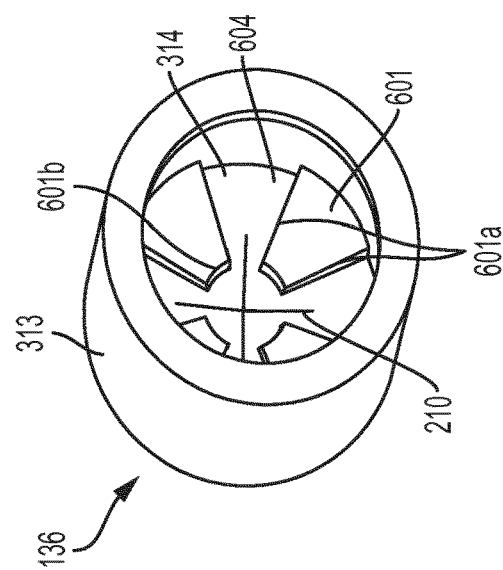

FIGS. 6A, 6B, and 6C illustrate an exemplary embodiment of a valve 136 (see FIGS. 2A and 2B for exemplary features) having protruding ribs. The valve 136 can have a cylindrical portion 313 and a central portion 314, which can be referred to as a valve disk, at a first end 311. FIG. 6A illustrates the valve 136 as seen from a second end 312, which may be the proximal end of the valve. Four interior ribs 601 can protrude from an inner surface 604 of the central portion 314. The four interior ribs 601 can be spaced equidistantly from each other in a concentric layout. Each of the interior ribs 601 can be generally wedge shaped, or pie shaped, extending from the interior surface 606 of the cylindrical portion towards the center 209. The wedge shape of the interior ribs 601 is defined by two inwardly tapering sidewalls 601a and an end wall 601b. The end wall 601b can be radiused concavely. Alternatively, the sidewalls 601a may be parallel to each other such that the interior ribs 601 can have rectangular shapes rather than wedges. In an exemplary embodiment, the end walls 601b of each of the interior ribs 601 may be radiused concavely such that the arcuate sections define a concentric ring around the center 209 of the central portion 314. The end walls 601b of the interior ribs 601 may have alternative geometry, such as flat, concave, convex, or obliquely tapered to meet the inner surface 604.

FIG. 6B illustrates the valve 136 as seen from a first end 311, which may be the distal end of the valve. On an outer surface 605 of the central portion 314, four exterior ribs 602 protrude from the outer surface 605. The ribs 602 are spaced from one another. That is, in the present embodiment, the ribs do not connect or touch one another. Each of the exterior ribs 602 can have an arrow shape, or a stadium shape with one end converging to a point. The shape of the exterior ribs 602 is defined by two parallel sides connected by a semi-circle on outer ends and a triangular, arrow on inner ends. The exterior ribs 602 can be inset from the outer perimeter of the valve 136.

The locations of the four exterior ribs 602 match and overlay with the locations of the interior ribs 601 when viewed along the axis of the valve 136. The four slits 210 can be disposed between the ribs 601, 602 and extend through the central portion 314. The four slits 210 define four flaps 211 configured to be moveable relative to the cylindrical portion 313 of the valve 136 to allow for fluid flow.

FIG. 6C illustrates a cross-sectional view of the valve 136. At the second end 312 of the valve 136, there is a lip 603. The lip 603 may be uniformly arranged circumferentially. The lip 603 can be formed of opposed and parallel lip sides 603a, 603b extending radially inwardly from the cylindrical portion 313. The lip inner side 603c is aligned in an axial direction, perpendicular to the parallel lip sides 603a, 603b.

The inner surface 604 of the central portion 314 extends at an oblique angle from the cylindrical portion 313 towards the center 209. The outer surface 605 extends at a perpendicular angle from the cylindrical portion 313 toward the center 209. In this way, the central portion 314 tapers down in thickness from the cylindrical portion 313 toward the center 209.

The four interior ribs 601 may have a substantially uniform thickness on the central portion 314. As such, a top surface of the interior ribs 601 may be parallel to the inner surface 604 of the central portion 314. With the varying thickness of the central portion 314, the distance between the interior ribs 601 to the exterior ribs 602 becomes smaller towards the center 209 of the central portion 314. Alternatively, the interior ribs 601 and the exterior ribs 602 each may have a varying thickness that decreases when closer to the center 209 of the valve 136. Still, the interior ribs 601 and the exterior ribs 602 each may have a varying thickness that increases towards the center 209 of the central portion 314.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 7C:
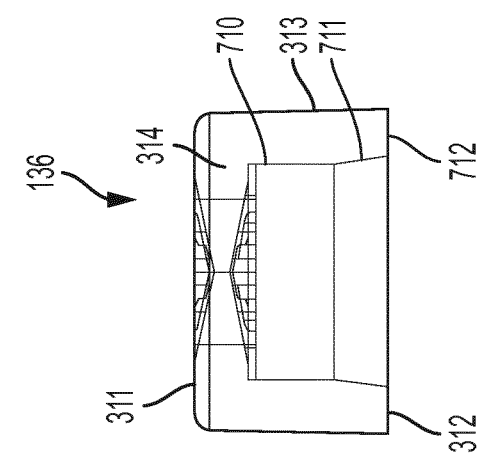
FIGS. 7A, 7B, and 7C show a valve having an interior recess formed by a central portion that is located at a first end and offset from the medial plane.
Figure 7B:
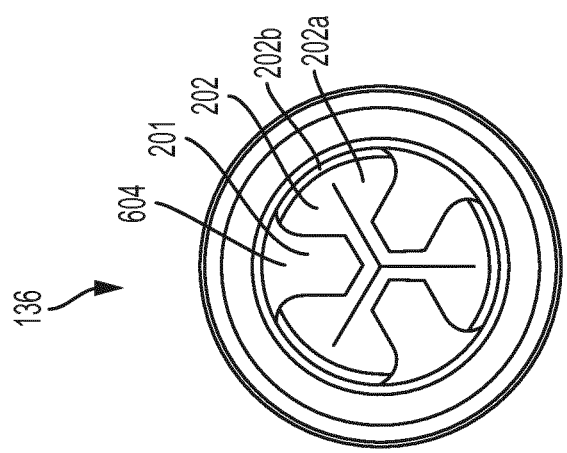
Figure 7A:
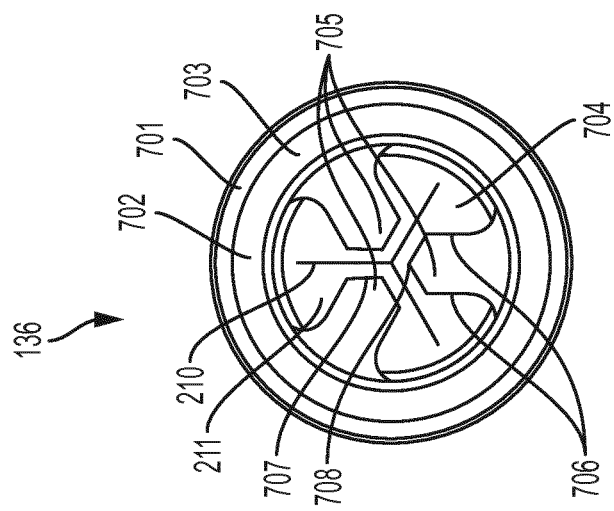

FIGS. 7A, 7B, and 7C illustrate an exemplary embodiment of a valve 136 (see FIGS. 2A and 2B for exemplary features) having an interior recess formed by a central portion 314, which can be referred to as a valve disk, that is located at a first end 311 and offset from the medial plane 212. The valve 136 can have a cylindrical portion 313 and the central portion 314.

FIG. 7A illustrates a valve 136 as viewed from a first end 311. The outer surface 605 of the central portion 314 blends into the cylindrical portion 313 with a first fillet, strip, or band region 701 and a second fillet, strip, or band region 702. The first fillet region 701 and the second fillet region 702 can have different fillet radiuses. The first fillet region 701 may have a smaller radius than the second fillet region 702. The first fillet region 701 and the second fillet region 702 can each have a constant radius, or a varying radius. Alternatively, the first fillet region 701 and the second fillet region 702 can be a singular region having a constant or constantly varying radius fillet.

The outer surface 605 of the central portion 314 has a first portion 703 and a second portion 704. The first portion 703 can be a flat surface that is the outermost part of the first end 311 of the valve 136. The second portion 704 can be inset in the first region 701 and includes a sloped portion extending towards the center 209 into the central portion 314. As shown in FIG. 7C, the second portion 704 forms a cutout in the central portion 314.

From the first portion 703, three exterior ribs 705 extend radially inward towards the center 209 of the valve 136. The exterior ribs 705 have a same thickness as that of the first portion 703. Each of the exterior ribs 705 can comprise of first sides 706 that are substantially parallel to one another. The exterior ribs 705 can each extend inwardly with a substantially constant width between the first sides 706. The ribs 705 can each have second sides 707, which converge towards a point 708 at an inward most end of the exterior rib 705.

The exterior ribs 705 extend radially inward adjacent to the second portion 704. The second portion 704 thus has a petal like arrangement formed from the first sides 706 and second sides 707. The second region 704 further has an outer arcuate side 709a and two radiused corners 709b. Accordingly, the outline of the arcuate side 709a, two radiused cornered 709b, first sides 706, and second sides 707 delineate the first portion 703 and the second portion 704.

Embodiments can be envisioned where the exterior ribs have alternative geometric shapes, such as a rectangle. The inward most end of the exterior ribs 705 does not have to converge to a point. Alternatively, the first sides 706 of the ribs 705 do not need to be parallel to one another. The first sides 706 may be skewed from one another to converge without second sides 707.

FIG. 7B illustrates a valve 136 as viewed from a second end 312. The inner surface 604 of the central portion 314 has a first portion 201 and a second portion 202. As shown in combination with FIG. 7C, the first portion 201 has a flat surface perpendicular to the axial direction of the valve 136. The second portion 202 has a first region 202a and a second region 202b. The second region 202b has a flat surface perpendicular to the axial direction of the valve 136. Alternatively, the second region 202b can be angled to change the thickness of the valve 136. The first region 202a is inset in the second region 202b and includes a sloped portion extending towards the center 209 into the central portion 314. As illustrated across FIGS. 7A, 7B, and 7C, the first region 202a of the inner surface can overlay with the second portion 704 of the outer surface 605.

From the first portion 201, three ribs 208 extend radially inward towards the center 209 of the valve 136. The ribs 208 can have a same thickness as that of the first portion 201. Each of the ribs 208 can comprise of first sides 204 that are substantially parallel to one another. The ribs 208 can each extend inwardly with a substantially constant width between the first sides 204. The ribs 208 can each have second sides 205, which converge towards a point 206 at an inward most end of the rib 208.

The ribs 208 can extend radially inward adjacent to the first region 202a and the second region 202b. The first region 202a thus has a petal like arrangement formed from the first sides 204 and second sides 205. The first region 202a can further have an outer arcuate side 203a and two radiused corners 203b. Accordingly, the outline of the arcuate side 203a, two radiused cornered 203b, first sides 204, and second sides 205 can delineate the first portion 201 and the second portion 202.

Embodiments can be envisioned where the rib has alternative geometric shapes, such as a rectangle. The inwardmost end of the rib 208 does not have to converge to a point. Alternatively, the first sides 204 of the ribs 208 do not need to be parallel to one another. The first sides 204 may be skewed from one another to converge without second sides 205.

As shown in FIG. 7C, the first region 202a and the second region 202b form a cutout in the central portion 314. The second region 202b can extend from tangentially meeting a first inner circumference 710 and forms a step down from the first portion 201. The first region 202a can then extend into the central portion 314 from the level of the second region 202b. Alternatively, the second region 202b may be inset from the first inner circumference 710 instead of tangentially contacting the first inner circumference.

In the first region 202a, three slits 210 are provided through the valve 136 from one side to the other side of the central portion or valve disk 314. The slits 210 extend radially and connect to a point in the center 209. The slits 210 define flaps 211. In the particular example, the three slits 210 provided through the valve 136 define three flaps 211. The flaps 211 are configured to be moveable relative to the outer perimeter 207 of the valve 136 to allow for fluid flow. The three slits 210 can each extend lengthwise to the edge of the first region 202a. The three slits 210 can each be within the first region 202a. Alternatively, the three slits 210 can each extend lengthwise into the second region 202b.

FIG. 7C, in conjunction with FIG. 7B, shows that the inner surface 315 of the cylindrical portion 313 has a taper. At an inner most part of the inner surface 315, the first inner circumference 710 can have a first circumference defining a bottom end of the inner surface 315. Midway along the inner surface 315, there is a second inner circumference 711. The second inner circumference can have a circumference larger than a circumference of the first inner circumference, and the inner surface 315 is tapered to bridge the first and second inner circumferences. At another end of the inner surface 315 is a third inner circumference 712, the third inner circumference having a circumference larger than the circumference of the second inner circumference. Accordingly, the inner circumference of the cylindrical portion 313 increases from the central portion 314 towards the second end 312.

In other examples, additional defining circumferences can be used for the inner surface 315 to alter the geometry. Also, varying geometries can be used to bridge the defining circumferences of the inner surface 315.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

FIGS. 8A and 8B illustrate embodiments where one of the sides of the valve 136 (see FIGS. 2A and 2B for exemplary features) does not have ribbing. In FIG. 8A, there is provided a valve 136 as generally illustrated in FIGS. 7A, 7B, and 7C. However, the valve 136 of FIG. 8A does not have the interior ribs 208. Instead, the inner surface 604 has a first portion 201 and a second portion 202, wherein the first portion 201 is a concentric ring arranged around the second portion 202. The second portion 202 is then conical in layout as it tapers towards the center 209 of the central portion 314.

FIG. 8B is a cross-sectional side view of the valve 136 of FIG. 8A shown without exterior ribs 705 and can be considered a reverse of the valve illustrated in FIGS. 7A, 7B, and 7C. In the present embodiment, the outer surface 605 can have a first portion 703 and a second portion 704, wherein the first portion 703 is a concentric ring arranged around the second portion 704. The second portion 704 is then conical in layout as it tapers towards the center 209 of the central portion 314. In view of the present disclosure, such modification to have only ribs on one side of the valve 136 would be readily applicable to any of the valves 136 disclosed herein.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 9B:
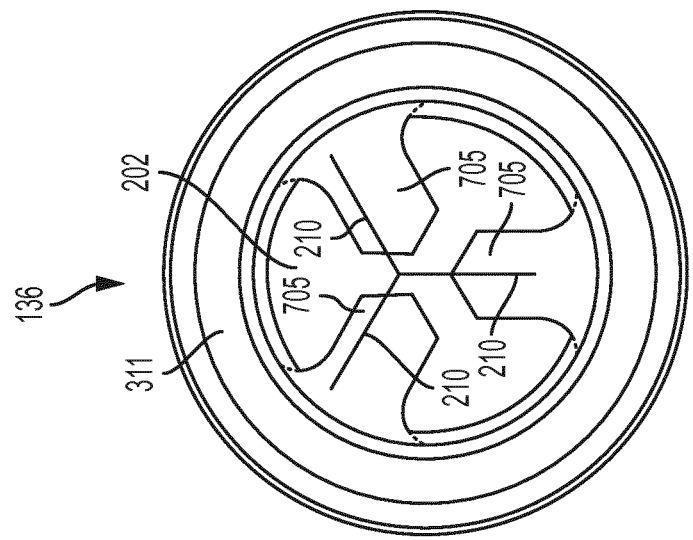
FIGS. 9A and 9B show a valve where the slits are arranged along the thicker sections having the ribs instead of the thinner sections of the valve.
Figure 9A:
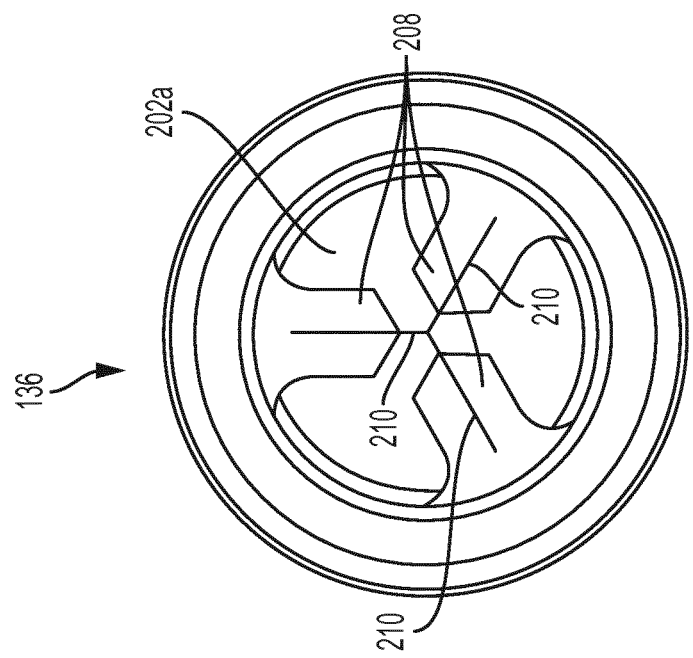

FIGS. 9A and 9B illustrate embodiments where the slits 210 are arranged along the thicker sections having the ribs 208, 705 instead of the thinner sections of the valve 136 (see FIGS. 2A and 2B for exemplary features). FIG. 9A shows a second end 312 of the valve 136, wherein the slits 210 are arranged to extend from the first region 202a of the second portion 202 and extend into the ribs 208 instead of only extending along the thinner first region 202a. FIG. 9B shows a first end 311 of the valve 136, wherein the slits 210 are arranged to extend from the second portion 202 and extend into the exterior ribs 705 instead of only extending along the thinner second portion 202. In other examples, the slits 210 of the valves 136 described and shown could have such an arrangement where the slits 210 extend along thicker sections of the valve 136 where the ribs 208, 705 are formed.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

FIGS. 10A, 10B, and 10C illustrate an embodiment of a valve 136 (see FIGS. 2A and 2B for exemplary features) having protruding interior ribs 601 and recessed exterior ribs 705. The valve 136 has a cylindrical portion 313 and a central portion 314 at a first end 311.

FIG. 10A illustrates the valve 136 as seen from a second end 312, which may be the proximal end of the valve. Four interior ribs 601 protrude from an inner surface 604 of the central portion 314, which may be called a valve disk. The four interior ribs 601 can be spaced equidistantly from each other in a concentric layout. Each of the interior ribs 601 can be generally arrow shaped extending from the interior surface 606 of the cylindrical portion towards the center 209. The arrow shape of the interior ribs 601 is defined by two parallel side edges 1010a and two converging sidewalls 1010b. Each of the interior ribs 601 has a cross sectional shape defined by a minor arc 1011 extending from the inner surface 604 across the side edges 1010a. The converging sidewalls 1010b can each be defined by a converging line 1010c, a length along the inner surface 604, and an arcuate length from the minor arc. Alternatively, the sidewalls 601a may be skewed to each other such that the interior ribs 601 have wedge shapes. The ribs may have alternative geometry, such as flat, concave, or obliquely tapered.

FIG. 10B illustrates the valve 136 as seen from a first end 311, which may be the distal end of the valve. On an outer surface 605 of the central portion 314, there is formed a void 1012 having a cross shaped portion 1012a and a conical void portion 1012b. The cross shaped portion 1012a comprises two grooves 1013 arranged in a cross shaped pattern extending into the valve 136 from the outer surface 605. The grooves 1013 can have sidewalls 1013a that are perpendicular to the outer surface 605. The sidewalls are parallel to one another.

The conical void portion is arranged concentrically around a center 209 of the valve 136. The conical void portion 1012b includes two concentrically arranged portions, a first conical void portion 1014a and a second conical void portion 1014b. The first conical void portion 1014a can be the innermost area. It has a depth into the outer surface 605 that is less than a depth of the grooves 1013. The second conical void portion 1014b has a taper and has a surface partially bridging the outer surface 605 and the first conical void portion 1014a. There is an additional vertical sidewall 1014c to bridge the second conical void portion and the first conical void portion 1014a. The second conical void portion 1014b is arranged around the first conical void portion 1014a. A diameter of the second conical void portion 1014b is less than a length of the grooves 1013.

Alternatively, additional voids can be created, such as a star shaped pattern instead of a cross, by adding one additional channel. Also, additional concentric areas can be arranged for conical void portion.

Slits 210 are provided across the length of the grooves 1013, and extend through the valve 136 from the proximal side to the distal side. The slits 210 extend radially and connect to a point in the center 209. The slits 210 define flaps 211. In the particular example, the four slits 210 provided through the valve 136 define four flaps 211. The flaps 211 are configured to be moveable relative to the cylindrical portion 313 of the valve 136 to allow for fluid flow.

FIG. 10C illustrates a cross-sectional view of the valve 136. FIG. 10C illustrates the depth of the second conical void portion 1014b as it tapers. The grooves 1013 define the deepest void from the outer surface 605. The conical void portion removes additional periphery material from the central portion around the grooves 1013.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 11C:
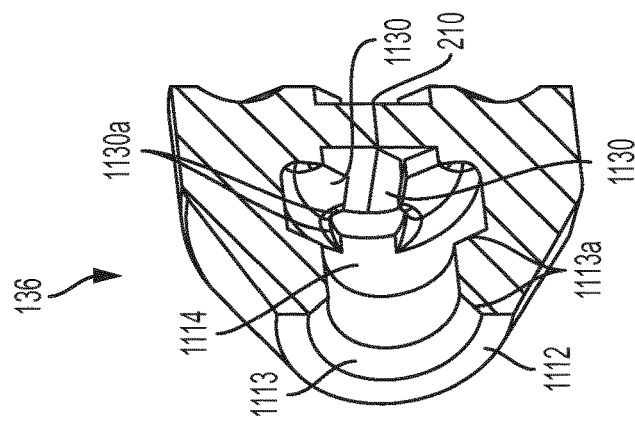
FIGS. 11A, 11B, and 11C show a valve having chamfering and filleting applied to various geometries.
Figure 11B:
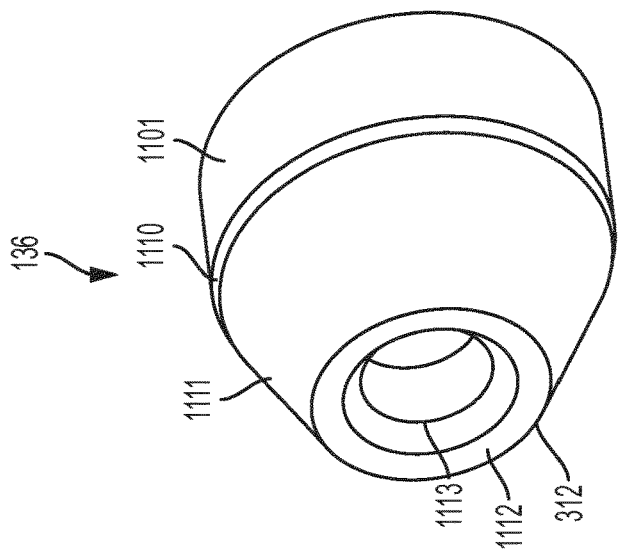
Figure 11A:
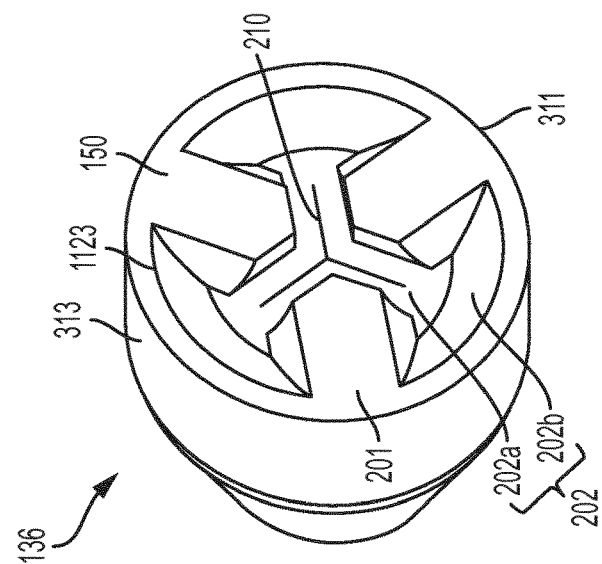

FIGS. 11A, 11B, and 11C illustrate a valve 136 (see FIGS. 2A and 2B for exemplary features) having chamfering and filleting applied to various geometries.

FIG. 11A shows the valve 136 from a first end 311. The first end 311 of the valve has a first portion 201 and a second portion 202, the first portion being arranged around the outside of the second portion 202. The first portion 201 is a first surface 150. The second portion 202 can form a void, or recess, extending into the first surface 150. The second portion 202 has a first region 202a set at a substantially constant depth into the central portion 314, and a second region 202b having a varying depth. The second region 202b can be located radially outward from the first region 202a near an outer perimeter 207. The first region 202a can have a surface substantially parallel to a surface of the first portion 201. The second region 202b can have a surface bridging the surface of the first region 202a and the first portion 201.

From the first portion 201, three ribs 208 extend radially inward towards the center 209 of the valve 136. The ribs 208 have a same depth as that of the first surface 150. Each of the ribs 208 comprises first edges 1120 that are substantially parallel to one another. The ribs 208 each extend inwardly with a substantially constant width between the first edges 1120. The ribs 208 each have second edges 1121, which converge towards a point 1122 at an inward most end of the rib 208.

The ribs 208 extend radially inward adjacent to the first region 202a and the second region 202b. The second portion 202 thus has a petal like arrangement formed from the first edges 1120 and second edges 1121. The second region 202b further has an outer arcuate edge 1123 and two radiused corners 1124. Accordingly, the outline of the arcuate edge 1123, two radiused cornered 1124, first edges 1120, and second edges 1121 delineate the first portion 201 and the second portion 202. The surfaces bridging the arcuate edge 1123, two radiused cornered 1124, and the first edges 1120 to the first region 202a are chamfered, such that they are inclined relative to the first surface 150.

FIG. 11B shows the valve 136 from a second end 312. The cylindrical portion 313 of the valve 136 can have a first cylindrical region 1101, which can transition to a fillet region 1110 and then to a conical portion 1111 at the second end 312. The second end can have a sidewall end surface 1112, which has a radially inward extending lip 1113.

FIG. 11C shows a cross sectional view of the valve 136. The lip 1113 can have inwardly tapering sidewalls 1113a. On an interior of the lip 1113 can be a cavity 1114. On the second surface 151 of the central portion 314 of the valve 136, interior ribs 1130 can be provided in the cavity 1114. The interior ribs 1130 can be dimensioned differently from the ribs 208. The interior ribs 1130 can be generally overlaid in the same position as the ribs 208 inside the valve, such that slits 210 can extend between adjacent ribs in thin areas of the central portion 314. Top edges of the interior ribs 1130 may be filleted 1130a or radiused. While a chamfer or a fillet is shown in specific areas of the valve, a fillet or radiusing could also be applied in place of the chamfer, and vice versa.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 12C:
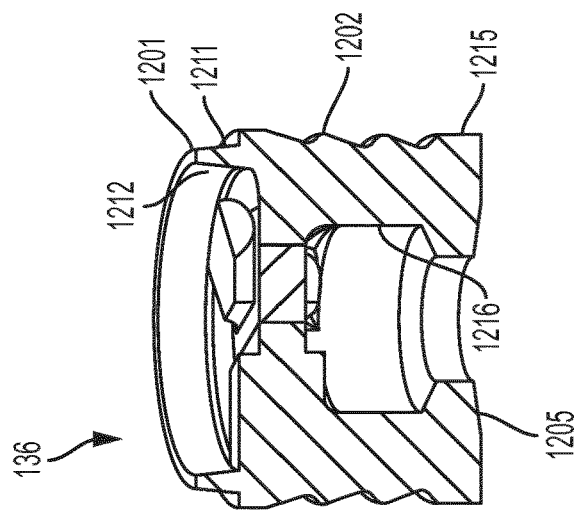
FIGS. 12A, 12B, and 12C show a valve having an externally ribbed surface.
Figure 12B:
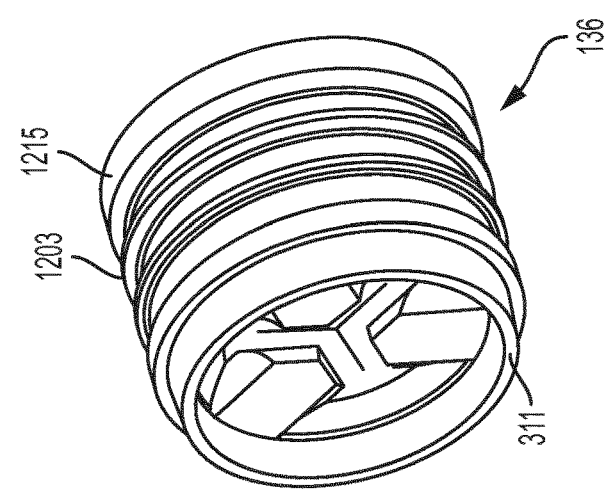
Figure 12A:
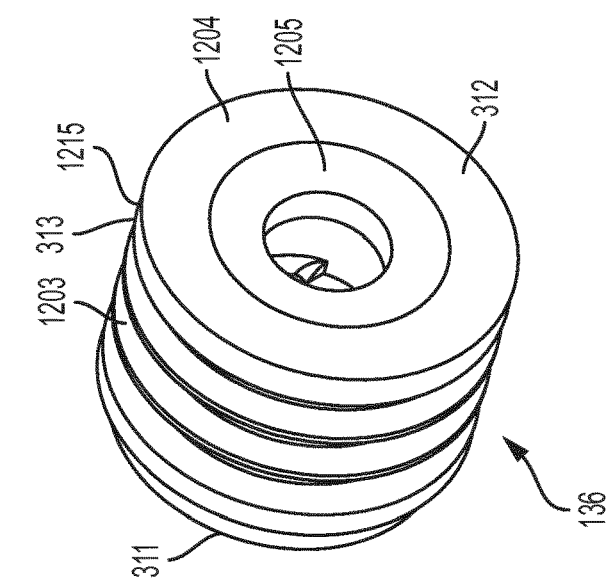

FIGS. 12A, 12B, and 12C illustrates an externally ribbed valve 136 (see FIGS. 2A and 2B for exemplary features). The structure of the ribs and central portion 314 are similar to the valve 136 shown in FIGS. 11A, 11B, and 11C. The cylindrical portion 313 has a first circumferential region 1201 and a second circumferential region 1202.

FIG. 12A shows the valve 136 from the second end 312. An outer surface 1215 can have external ribbing 1203. The external ribbing can vent air or gas but restrict or limit blood flow from flowing thereacross. Alternatively, the external ribbing can form multiple sealing sections with the interior surface of the catheter hub to prevent both gas and fluid flow from flowing thereacross. Also, the second end 312 can have a sidewall end surface 1204 with a lip 1205 defining a void to the opening of an interior of the valve 136. In FIG. 12C, the lip 1205 is further shown as having two inwardly tapering sidewalls 1205a.

FIG. 12B shows the valve 136 from the first end 311. The external ribbing 1203 can extend along the outer surface 1215 up to the sidewall 1213.

As shown in FIG. 12C, the first circumferential region 1201 can be on a first side of the central portion 314. The outer surface 1211 of the first circumferential region 1201 may be tapered inwardly towards the center 209 of the valve 136 towards a distal end of the cylindrical portion 313. The inner surface 1212 of the first circumferential region 1201 may be tapered outwardly away from the center 209 of the valve 136 towards a distal end of the cylindrical portion 313. In this way, the sidewall 1213 of the first circumferential region 1201 defined by the outer surface 1211 and the inner surface 1212 is tapered on both surfaces and narrows towards the distal end of the cylindrical portion 313. The first circumferential portion has a smaller diameter than the outer diameter of the second circumferential region 1202.

The second circumferential region 1202 can extend from the central portion 314 in a direction opposite to the first circumferential region 1201. The second circumferential region 1202 has a thicker sidewall 1214 than the sidewall 1213 of the first circumferential region 1201, having an outer surface 1215 with a diameter later than the outer surface 1211 and an inner surface 1216 with a diameter smaller than the inner surface 1212. The outer surface 1215 can have ribbing 1203 in a sawtooth pattern when viewed from a cross-section of a valve. The sawtooth pattern can be asymmetrical or symmetrical.

Although the valve 136 shown has radial ribs, the circumferential ribs may be axial and extend from one end to the other end of the valve 136.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 13B:
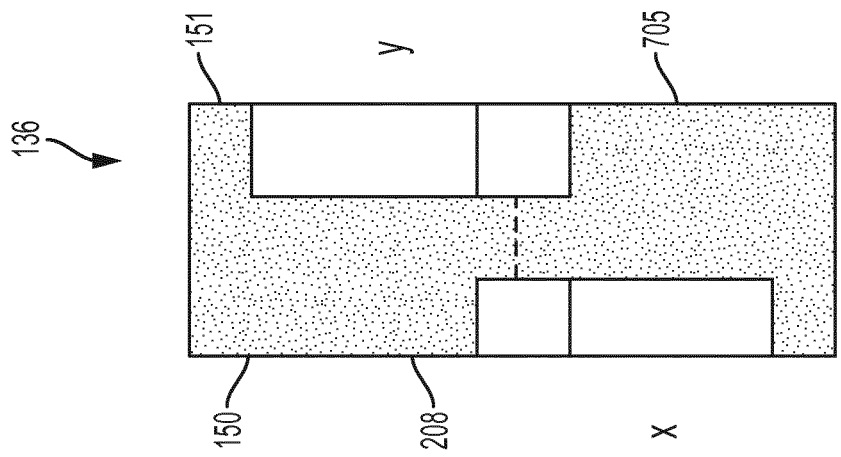
Figure 13A:
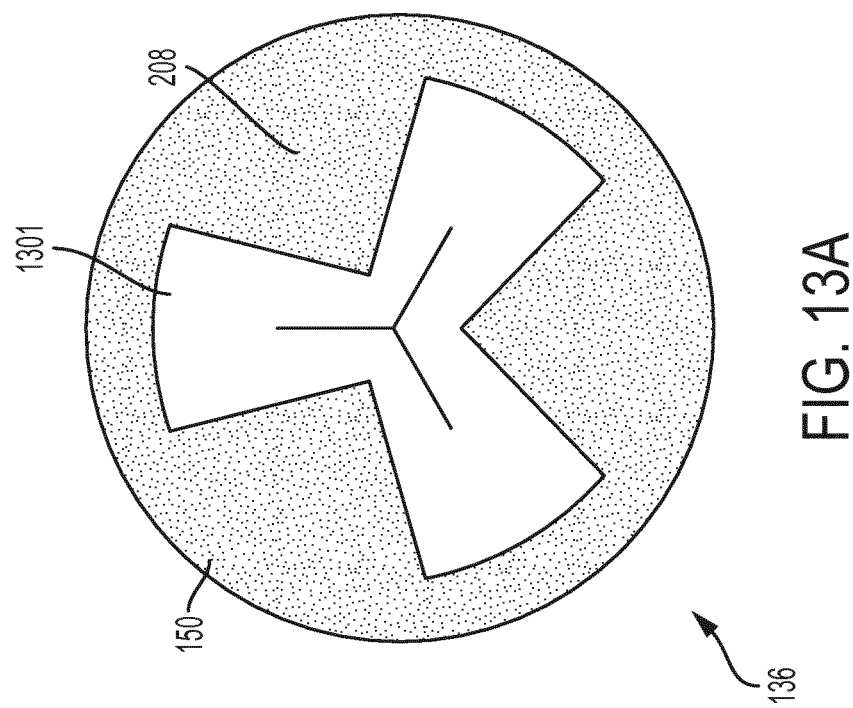

FIGS. 13A, 13B, and 13C illustrate where the ribs 208, 705 of the valve 136 (see FIGS. 2A and 2B for exemplary features) are not overlaid, but are rather offset from one another. FIG. 13A illustrates a first surface 150 having a void 1301 and three triangular ribs 208. FIG. 13B illustrates that the ribs on the first surface 150 may be oriented offset from the ribs 705 of the second surface 151. As such, a view of the cross section of the valve 136 will show that the first surface 150 and the second surface 151 are different. For example, the ribs on one surface may be rotated 180 degrees from the other surface. Alternatively, different numbers of ribs may be used on the opposed sides. FIG. 13C illustrates an embodiment where the thickness of the ribs on the opposed sides of the valve 136 may be different. In this case, the central portion 314 is offset from the medial plane 212.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 14B:
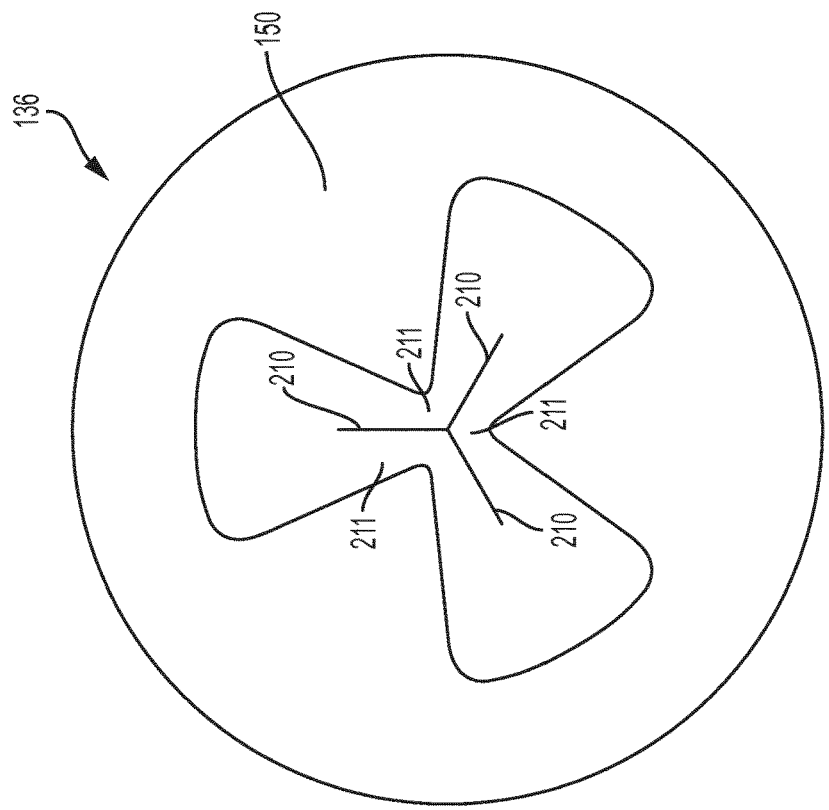
FIGS. 14A, 14B, 14C, and 14D show valves with sloping tear-drop shaped recesses.
Figure 14A:
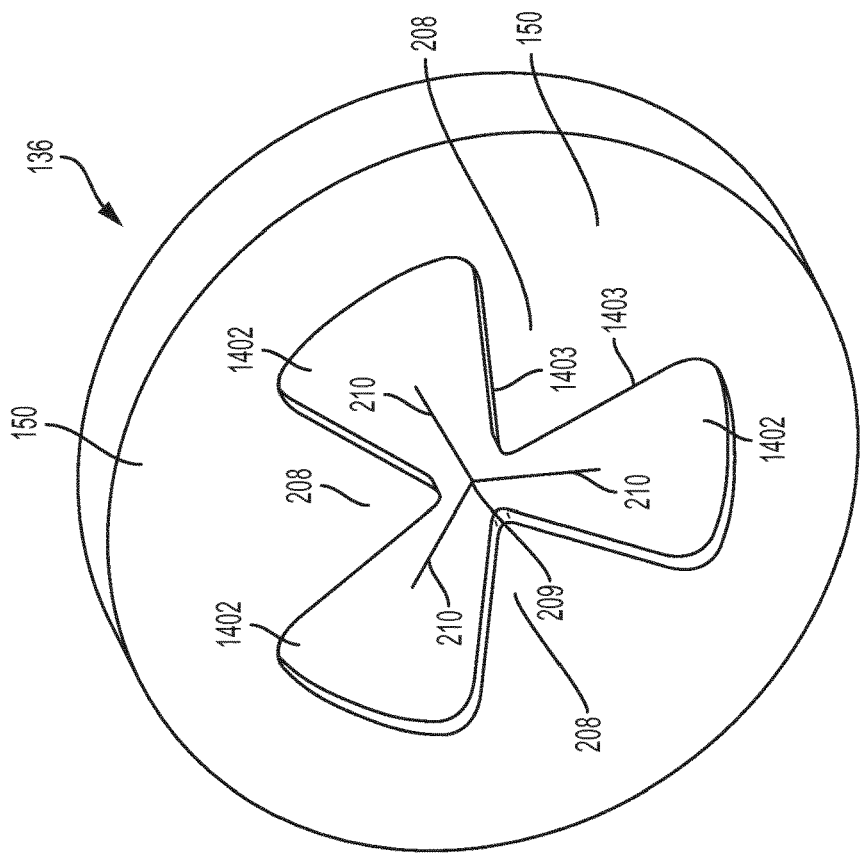

FIGS. 14A-D illustrate valves 136 (see FIGS. 2A and 2B for exemplary features) with a sloped recess. FIG. 14A shows a valve with three generally tear-drop shaped recesses 1402 having sloping surfaces, which also resemble a three-leaf clover. The three tear-drop shaped recesses 1402 can be coupled to each other at an inner area near the center 209. Each tear drop can have an enlarged end and a relatively smaller end. The three smaller ends of the three tear-drop shaped recesses can couple to one another at the relatively smaller ends. In other examples, there can be more than three tear-drop shaped recesses.

The tear-drop shaped recesses 1402 can gradually thin towards the center 209 of the valve 136. The outer part of the valve can have a greater thickness than the gradually thinning valve. The tear drop shaped recesses can each comprise an outer side region have a flatter curve than the arcuate side 203a of FIG. 2A and tapering sides compared to the sides 205 of the recess of FIG. 2A.

In an example, the sloped recesses of the present embodiment each comprises surface with a single slope instead of two or more distinct slope sections. In other examples, towards the center 209, the three tear-drop shaped recesses can have a generally flat area or a region with essentially zero slope.

Slits 210 are provided through the valve 136 in the tear-drop shaped recesses 1402, thus forming flaps 211. There can be one or more slits, such as three slits, forming two or more flaps. As shown, three slits 210 form three flaps 211. In some examples, a slit can be provided through each tear drop shaped recess. Each slit can extend from the relatively smaller end and partially along a length of each tear drop shaped recess. In some examples, each slit can extend through the thickness of the valve at a first region but not at a second region. In other examples, the slits can cut through at least part of the ribs 208. Ribs 208 can be defined by the sides 1403 of the tear-drop shaped recesses. The sloping surface of the tear-drop shaped recesses 1402 may be a constant slope from the first surface 150 to the center 209 or can be a complex slope or a variable slope.

Figure 14D:
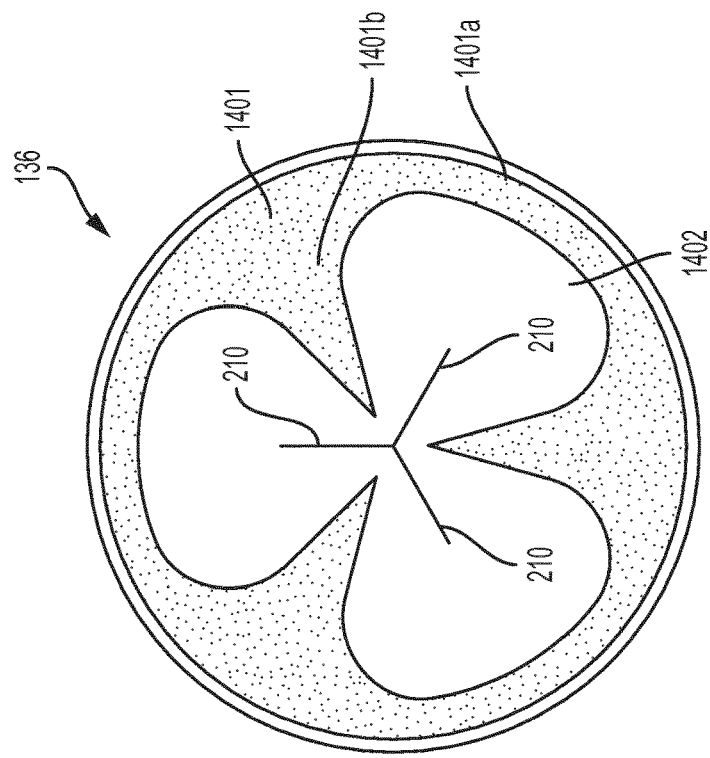
Figure 14C:
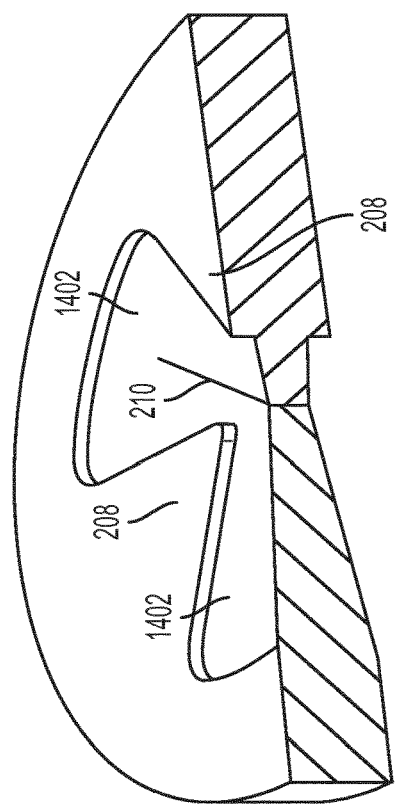

FIG. 14D illustrates a raised portion 1401 provided with a raised perimeter 1401a and three raised ribs 1401b above the tear-drop shaped recesses 1402. The raised ribs can have a uniform thickness, and accordingly can be angled towards the center due to the thinning tear-drop shaped recesses 1402. The tip of each rib can be pointed, rounded, or blunt. In some examples, the ribs can have the same thickness as the thickness of the valve along the outer periphery of the valve. The illustrated embodiment only shows the raised perimeter and triangular ribs on one surface of the valve 136, but the features can be understood as being provided on the opposed surface.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 15C:
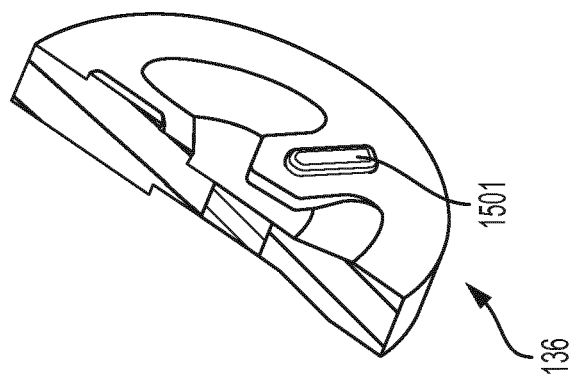
FIGS. 15A, 15B, and 15C show a valve where a secondary rib is formed on a rib.
Figure 15B:
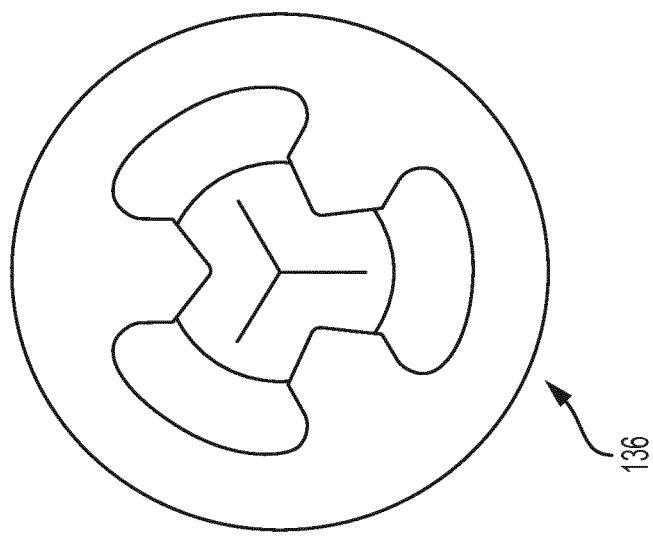
Figure 15A:
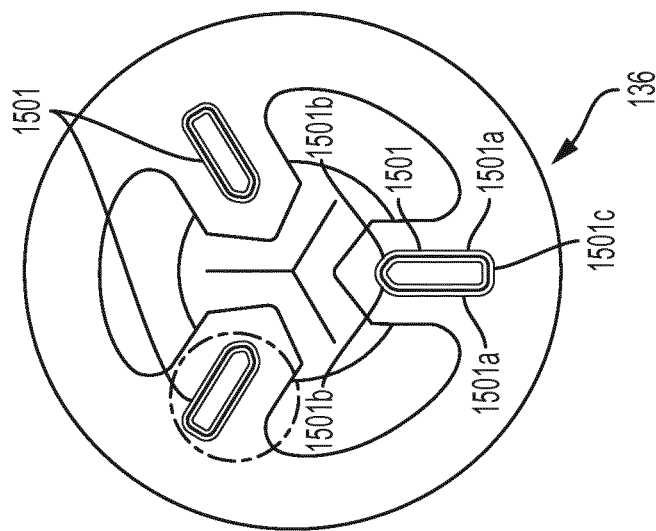

FIGS. 15A, 15B, and 15C illustrate an embodiment where a secondary rib 1501 is formed on a rib 208. FIG. 15 illustrates a valve 136 (see FIGS. 2A and 2B for exemplary features) in the style of the embodiment show in FIGS. 2A and 2B. Additionally, the valve 136 has secondary ribs 1501 on top of the ribs 208.

The secondary ribs 1501 can be inset over the ribs 208, protruding above the first surface 150. The secondary ribs 1501 generally have an arrow shape, defined by two side walls 1501a, two converging walls 1501b, and a rear wall 1501c. The two side walls 1501a can be parallel to each other and parallel to the first sides 204 of the respective rib 208 that the secondary rib 1501 is located on. The rear wall 1501c can be approximately located by the circumference of a circle taken around all of the outer arcuate sides 203a of the second region 202b of the second portion 202.

FIG. 15B shows the opposite side of the valve 136 without the secondary ribs 1501. However, the secondary ribs 1501 could be applied to both sides in addition to being on either side of the valve 136.

FIG. 15C shows a cross-sectional view of the valve 136 with the secondary ribs 1501. The secondary ribs 1501 are shown having filleted edges along the top and bottom. However, various edge finishes may be used as would be appropriate.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 16C:
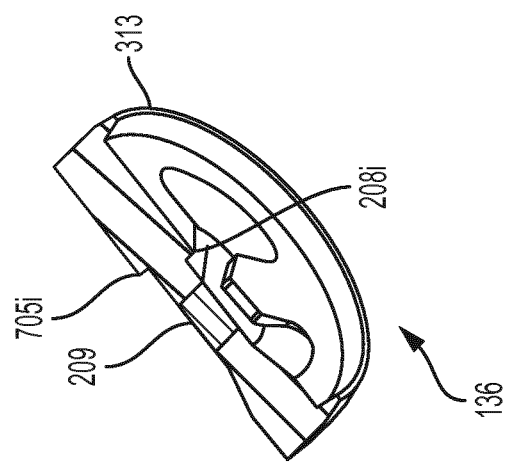
FIGS. 16A, 16B, and 16C show a valve where the dimensioning of the ribs on the first surface and the second surface are different, resulting in an asymmetrical valve.
Figure 16B:
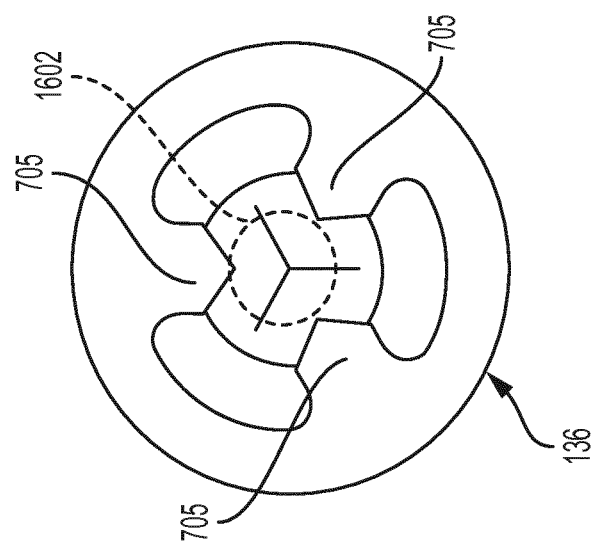
Figure 16A:
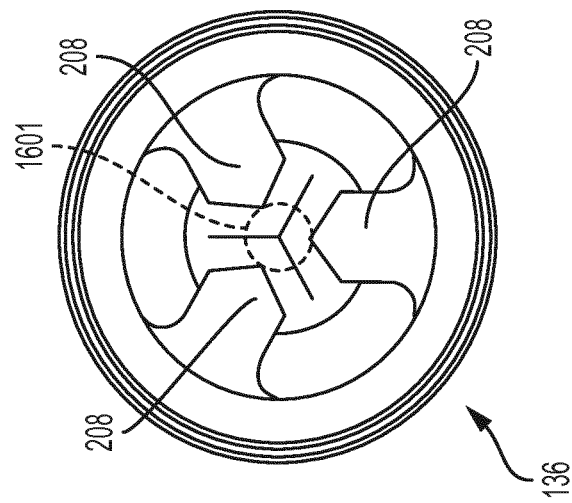

FIGS. 16A, 16B, and 16C illustrate embodiments of the valve 136 (see FIGS. 2A and 2B for exemplary features) where the dimensioning of the ribs on the first surface 150 and the second surface 151 are different, resulting in an asymmetrical valve 136.

FIG. 16A illustrates a first dimensioning of the ribs 208 on the first surface 150 of the valve 136. The innermost location 208i of the ribs 208 is indicated with the dotted circle 1601 as shown.

FIG. 16B shows the opposed side of the valve 136 with the second surface 151. Generally, the second surface 151 can have exterior ribs 705, opposed to the ribs 208 on the first surface 150. The innermost location 705i of the ribs 705 can be indicated with the dotted circle 1602 as shown. As drawn, the circle 1602 of the second surface 151 can be larger in diameter than the circle 1601 of the first surface 150.

FIG. 16C illustrates this difference between the ribs 208, 705 by showing the radial difference between the innermost location 705i of the exterior ribs 705 and the innermost location 208i of the ribs 208. Although FIG. 16C shows the ribs 208 of the first surface 150 as being larger by extending closer to the center 209 of the valve than the exterior ribs, the reverse is also possible.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

FIGS. 17A and 17B illustrate a valve actuator 134 configured to actuate the valve 136. The valve actuator 134 includes an actuator head 134a and an actuator leg 134b. The actuator head has a distal end having a distal end diameter 1731, a proximal end having a proximal end diameter 1730, and a head length 1732. In embodiments, the proximal end diameter 1730 is also a maximum diameter, or greatest diameter of the actuator 134. The distal end diameter 1731 is smaller than the proximal end diameter 1730.

FIGS. 18A and 18B illustrate contact between the valve actuator 134 and the valve 136 (see FIGS. 2A and 2B for exemplary features). FIG. 18A shows a first position of the valve where the valve 136 is in a closed position with the valve actuator 134 contacting the valve 136 without deforming the valve 136. A first line 1801 representing the line of contact between the actuator head 134a and a surface of the ribs 1802.

FIG. 18B shows a second position of the valve where the valve 136 is in an opened position with the valve actuator 134 contacting the valve 136 and deforming the valve 136 by pushing on the surface of the ribs 1802. A second line 1804 represents the line of contact between the actuator head 134a and the surface of the ribs 1802 in the opened position. The distance 1803 between the first line 1801 and the second line 1804 can be considered the rib travel distance.

Figure 19:
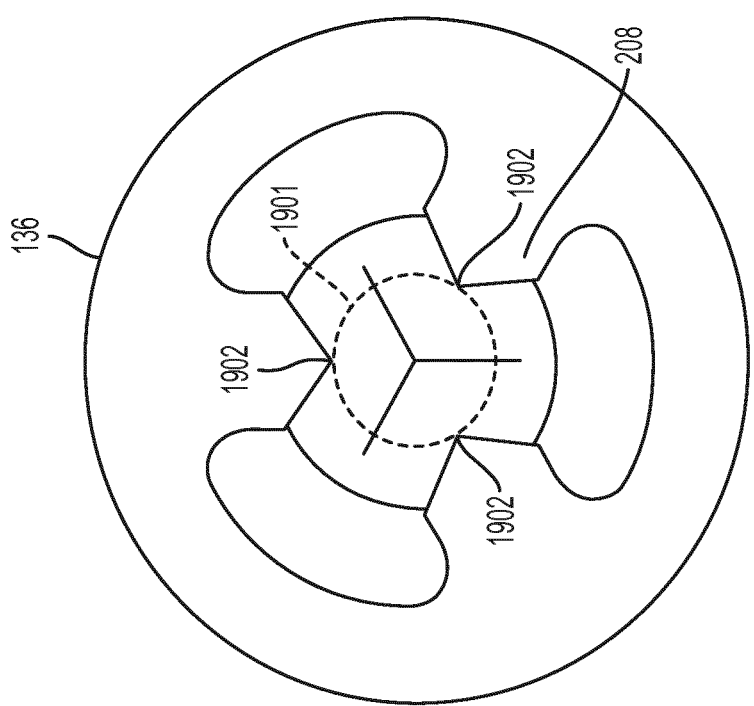
FIG. 19 shows a valve and a dotted circle representing what is termed as an area of reduced thickness.

FIG. 19 illustrates a valve (see FIGS. 2A and 2B for exemplary features) and a dotted circle 1901 representing what is termed as an area of reduced thickness. This area of reduced thickness can be understood as a portion of the area of the second portion 202 of a valve 136 where the thickness is less than the ribbed portion of the valve 136. The area of reduced thickness may be a circular area bounded by distal ends 1902 of the ribs 208. In embodiments, the diameter of the area of reduced thickness is equal to or less than the maximum diameter of the actuator head. In embodiments, the diameter of the area of reduced thickness is equal to or less than the actuator distal end diameter. In embodiments, the diameter of the area of reduced thickness is equal to or greater than the diameter of the needle shaft.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve.

Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 26B:
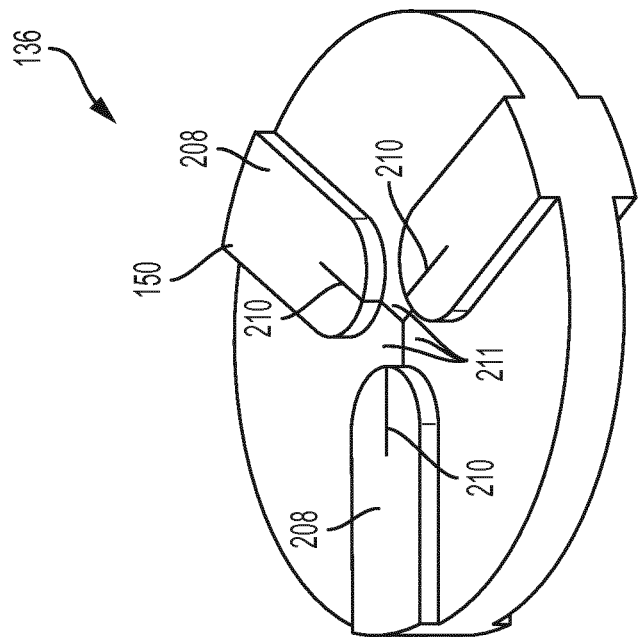
FIGS. 26A and 26B show a valve with a flat portion and ribs protruding from the flat portion.
Figure 26A:
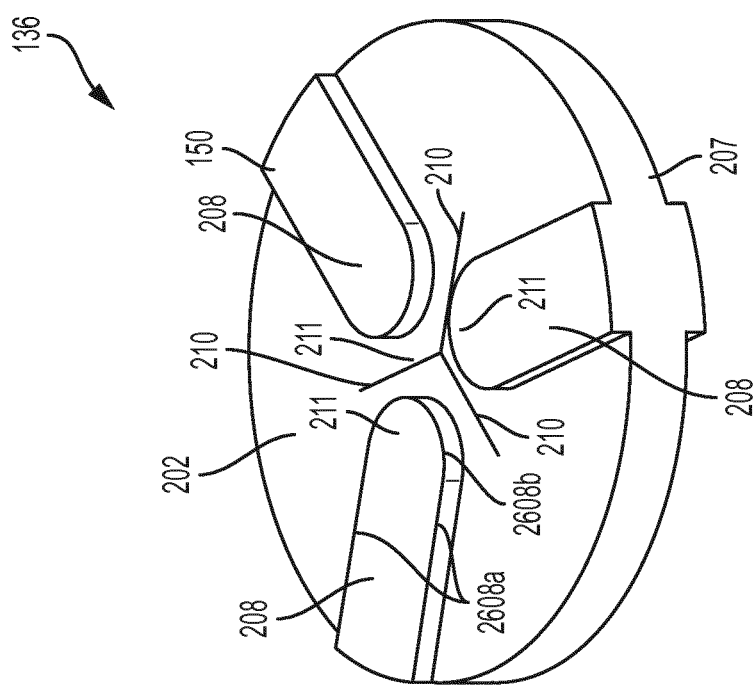

FIGS. 26A and 26B illustrate a valve 136 (see FIGS. 2A and 2B for exemplary features) with a substantially flat second portion 202 for use with a catheter assembly described elsewhere herein. A plurality of ribs 208 can project from the substantially flat second portion 202. The ribs 208 can be defined generally by two parallel sides 2608*a* extending radially inward and an arcuate end side 2608*b* near the center of the valve. The sides 2608*a*, 2608*b* can have substantially uniform thicknesses. The end side opposite the arcuate end side 2608*b* of each rib can be common or coincident with the outer perimeter 207 of the valve.

FIG. 26A illustrates where the slits 210 extend through the valve 136 in the second portion 202, between the ribs 208. In this way, three corresponding flaps 211 are formed by the three slits 210, the flaps 211 being configured to be moveable relative to the outer perimeter 207 of the valve 136 to allow for fluid flow. The valve of FIG. 26A can have similar surface features about the medial plane of the valve. FIG. 26B illustrates where the slits 210 extend into the ribs 208 from the second portion 202. The illustrated embodiment only shows the features on one surface of the valve 136, but the features can be understood as being provided on the opposed surface of the valve.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Figure 27B:
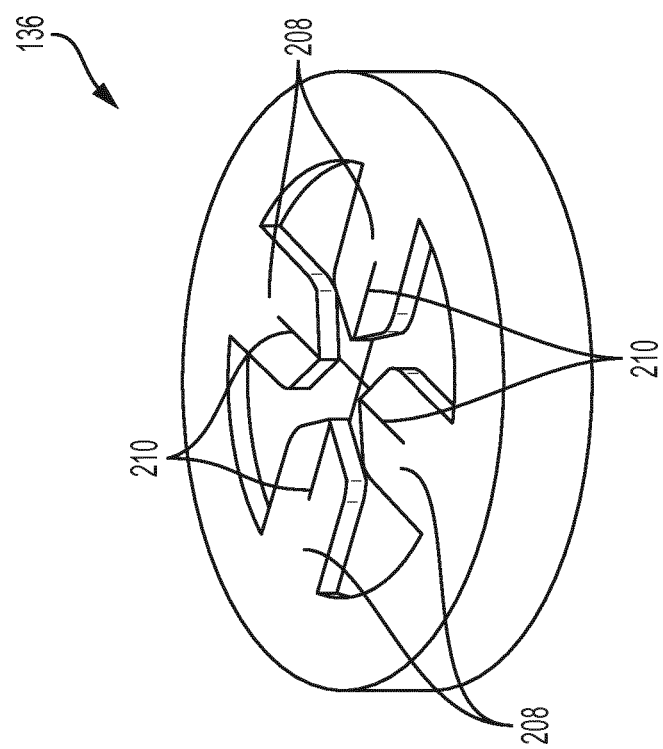
FIGS. 27A and 27B show a valve with four ribs.
Figure 27A:
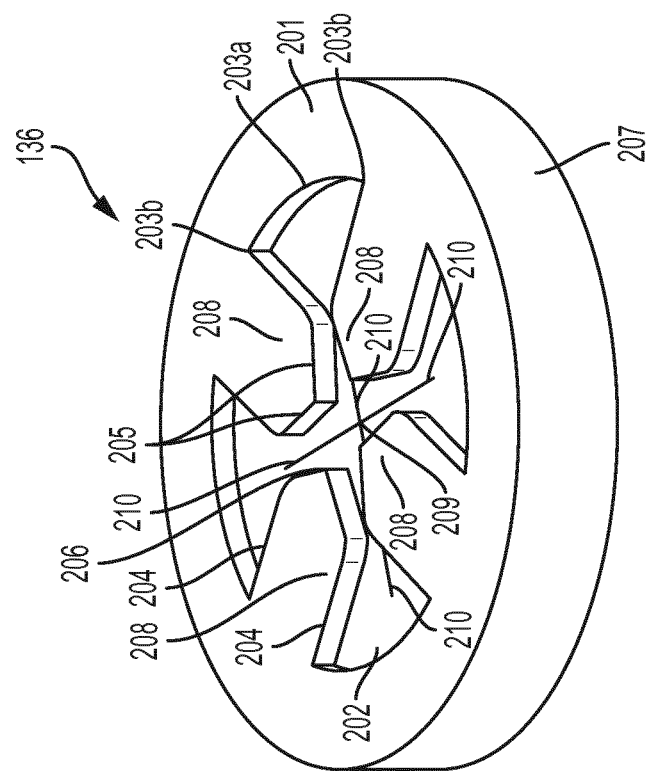

FIGS. 27A and 27B illustrate a valve 136 (see FIGS. 2A and 2B for exemplary features) having a cross shaped pattern formed by the recesses of the second portion 202 and useable in a catheter assembly described elsewhere herein. The second portion 202 can be substantially flat. From a first portion 201, four ribs 208 can extend radially inward towards the center 209 of the valve 136. The ribs 208 can have a same thickness as that of the first portion 201. Each of the ribs 208 can comprise of first sides 204 that are substantially parallel to one another. The ribs 208 can each extend inwardly with a substantially constant width between the first sides 204. The ribs 208 can each have second sides 205, which can converge towards a point 206 at an inward most end of the rib 208.

The ribs 208 extend radially inward adjacent to the second portion 202. The second portion 202 can therefore have a cross like arrangement formed from the first sides 204 and second sides 205. The second portion 202 can have an outer arcuate side 203*a* and two corners 203*b*. Accordingly, the outline of the arcuate side 203*a*, two cornered 203*b*, first sides 204, and second sides 205 can delineate the first portion 201 and the second portion 202. The outline can be of a substantially uniform thickness or width from the first portion 201 to the second portion 202.

The second portion 202 can resemble four funnel shaped recess sections joined to one another along or near the center of the valve. Each funnel shaped recess can have an outer arcuate end wall and two sidewalls that taper with each side wall having a generally straight edge. The ribs extending above or projecting beyond the surface of the second portion 202 can be generally constant.

FIG. 27A illustrates where the four slits 210 extend through the valve 136 in the second portion 202, between the ribs 208. In this way, four corresponding flaps 211 are formed, the flaps 211 being configured to be moveable relative to the outer perimeter 207 of the valve 136 to allow for fluid flow. FIG. 27B illustrates where the slits 210 extend into the ribs 208 from the second portion 202. The illustrated embodiment only shows the features on one surface of the valve 136, but the features can be understood as being provided on the opposed surface.

Embodiments of the present disclosure can provide an advantage of having arrow shaped ribs extending towards the slit is to have earlier contact between the valve opener and the valve upon insertion of a Luer connector, therefore allowing earlier opening of the valve (reduces the travel distance needed by the valve opener to open the valve). Said differently, the girth or thickness provided by the ribs allow the valve to be contacted earlier by a valve opener compared to a similar valve without the disclosed ribs.

Embodiments of the present disclosure with the rib joined to the outer or peripheral border of the valve 136 can help to prevent the actuator head from getting stuck in the open position when the actuator is used to open the valve. Additionally, joining the rib to the outer or peripheral border of the valve 136 can improve the ability of the valve flaps to return to a closed position to re-seal the slit post-actuation, e.g., after the removal of a Luer adapter.

Embodiments of the present disclosure where the outer or peripheral border is thicker than a central region can provide a greater surface area for contact with a catheter hub wall while preventing the higher drag force that would normally be associated with a thicker valve, since the central region, which is the region in contact with the needle shaft, will be thinner.

Although limited embodiments of the valve and its application in catheter assemblies have been specifically described and illustrated herein, many modifications and variations will be apparent to those skilled in the art. For example, the various parts of the valve may incorporate alternate materials, etc. Furthermore, it is understood and contemplated that features specifically discussed for one valve embodiment may be adopted for inclusion with another valve embodiment, provided the functions are compatible. Accordingly, it is to be understood that the valve and its application in catheter assemblies constructed according to principles of the disclosed device, system, and method may be embodied other than as specifically described herein. The disclosure is also defined in the following claims.

What is claimed is:

1. A catheter assembly comprising a catheter hub having a catheter tube extending from a distal end thereof, a needle hub having a needle extending from a distal end thereof and extending through the catheter hub in a ready to use position, and a valve located inside the catheter hub, the valve comprising:
   a first side having a first surface defining a first plane having a first portion and having a second portion on the first side recessed from the first plane;
   a second side having a second surface opposing the first surface and defining a second plane, the first surface and the second surface defining a thickness of the valve;
   a plurality of slits extending from the first side to the second side of the valve at the second portion, the plurality of slits defining a plurality of flaps with each of the plurality of slits having an inward-most slit point and a radially outward-most point and wherein an imaginary arc connects the radially outward-most points of the plurality of slits to define a circular boundary;
   at least two ribs on the first side, each of said at least two ribs having an exterior surface located on the first plane and extending from a point outside the circular boundary into the circular boundary;
   a valve actuator slidably disposed inside the catheter hub, said valve actuator having an actuator head with a surface for pushing into the valve to deflect the flaps when a surface on a plunger end of the valve actuator is pushed by a connector tip inserted into the catheter hub in a used position; and
   wherein the first surface defining the first plane extends radially outwardly of the exterior surface of each of the at least two ribs.

2. The catheter assembly according to claim 1, wherein the first surface has a circular outer boundary.

3. The catheter assembly according to claim 2, wherein the second portion of the first side comprises a first region and a second region, said first region having a recessed planar surface recessed from said first plane.

4. The catheter assembly according to claim 1, wherein the second portion is disposed over a central area of the first side; and each of the at least two ribs has a shape defined by a plurality of edges.

5. The catheter assembly according to claim 3, wherein the second region has a sloped surface bridging the first surface defining the first plane and the first region of the second portion.

6. The catheter assembly according to claim 1, wherein the at least two ribs are in a spaced relationship.

7. The catheter assembly according to claim 3, wherein the recessed planar surface of the first region of the second portion defines a diameter that is equal to or less than a maximum diameter of the actuator head of the actuator.

8. The catheter assembly according to claim 1, wherein the inward-most slit points of each of the plurality of slits converge at a single central point.

9. The catheter assembly according to claim 3, wherein each of the plurality of flaps comprises two edges that converge inwardly to an inward-most point to define a pointed tip.

10. The catheter assembly according to claim 1, wherein the plunger end comprises two plunger elements with each plunger element having a free end.

11. A catheter assembly comprising a catheter hub having a catheter tube extending from a distal end thereof, a needle hub having a needle extending from a distal end thereof and extending through the catheter hub in a ready to use position, and a valve located inside the catheter hub, the valve comprising:
   a first side having a first surface defining a first plane having a first portion;
   a second side having a second surface opposing the first surface and defining a second plane, the first surface and the second surface defining a thickness of the valve;
   a second portion on the first side recessed from the first plane;
   a plurality of slits extending from the first side to the second side of the valve at the second portion, the plurality of slits defining a plurality of flaps with each of the plurality of slits having an inward-most slit point and a radially outward-most point and wherein an imaginary arc connects the radially outward-most points of the plurality of slits to define a circular boundary;
   at least two ribs on the first side, each of said at least two ribs having an exterior surface extending from a point outside the circular boundary into the circular boundary;
   a valve actuator slidably disposed inside the catheter hub, said valve actuator having an actuator head with a surface for pushing into the valve to deflect the flaps when a surface on a plunger end of the valve actuator is pushed by a connector tip inserted into the catheter hub in a used position; and
   wherein each of the at least two ribs has an arrow shape or tapered shape located within the circular boundary.

12. A catheter assembly comprising a catheter hub having a catheter tube extending from a distal end thereof, a needle hub having a needle extending from a distal end thereof and extending through the catheter hub in a ready to use position, and a valve located inside the catheter hub, the valve comprising:
   a first side having a first surface defining a first plane having a first portion;
   a second side having a second surface opposing the first surface and defining a second plane, the first surface and the second surface defining a thickness of the valve;
   a second portion on the first side recessed from the first plane;
   a plurality of slits extending from the first side to the second side of the valve at the second portion, the plurality of slits defining a plurality of flaps with each of the plurality of slits having an inward-most slit point and a radially outward-most point and wherein an imaginary arc connects the radially outward-most points of the plurality of slits to define a circular boundary;
   at least two ribs on the first side, each of said at least two ribs having an exterior surface extending from a point outside the circular boundary into the circular boundary;
   a valve actuator slidably disposed inside the catheter hub, said valve actuator having an actuator head with a surface for pushing into the valve to deflect the flaps when a surface on a plunger end of the valve actuator is pushed by a connector tip inserted into the catheter hub in a used position; and wherein each of the at least two ribs has a thickness that equals the thickness of the valve.

13. The catheter assembly of claim 1, wherein the first side of the valve is oriented within the catheter hub to face a distal direction.

14. A catheter assembly comprising a catheter hub having a catheter tube extending from a distal end thereof, a needle hub having a needle extending from a distal end thereof and extending through the catheter hub in a ready to use position, and a valve located inside the catheter hub, the valve comprising:
- a first side having a first surface defining a first plane having a first portion;
- a second side having a second surface opposing the first surface and defining a second plane, the first surface and the second surface defining a thickness of the valve;
- a second portion on the first side recessed from the first plane;
- a plurality of slits extending from the first side to the second side of the valve at the second portion, the plurality of slits defining a plurality of flaps with each of the plurality of slits having an inward-most slit point and a radially outward-most point and wherein an imaginary arc connects the radially outward-most points of the plurality of slits to define a circular boundary;
- at least two ribs on the first side, each of said at least two ribs having an exterior surface extending from a point outside the circular boundary into the circular boundary;
- a valve actuator slidably disposed inside the catheter hub, said valve actuator having an actuator head with a surface for pushing into the valve to deflect the flaps when a surface on a plunger end of the valve actuator is pushed by a connector tip inserted into the catheter hub in a used position; and
- wherein the first side of the valve is oriented within the catheter hub to face a proximal direction.

15. A catheter assembly comprising a catheter hub having a catheter tube extending from a distal end thereof, a needle hub having a needle extending from a distal end thereof and extending through the catheter hub in a ready to use position, and a valve located inside the catheter hub, the valve comprising:
- a first side having a first surface defining a first plane having a first portion;
- a second side having a second surface opposing the first surface and defining a second plane, the first surface and the second surface defining a thickness of the valve;
- a second portion on the first side recessed from the first plane;
- a plurality of slits extending from the first side to the second side of the valve at the second portion, the plurality of slits defining a plurality of flaps with each of the plurality of slits having an inward-most slit point and a radially outward-most point and wherein an imaginary arc connects the radially outward-most points of the plurality of slits to define a circular boundary;
- at least two ribs on the first side, each of said at least two ribs having an exterior surface extending from a point outside the circular boundary into the circular boundary;
- a valve actuator slidably disposed inside the catheter hub, said valve actuator having an actuator head with a surface for pushing into the valve to deflect the flaps when a surface on a plunger end of the valve actuator is pushed by a connector tip inserted into the catheter hub in a used position; and
- wherein the second side comprises at least two ribs and wherein the at least two ribs of the second side are aligned with the at least two ribs on the first side.

16. The catheter assembly of claim 1, further comprising a needle guard located inside the catheter hub, said needle guard having a surface movable distal of a needle tip of the needle to prevent unintended needlesticks.

17. The catheter assembly of claim 1, wherein the second side of the valve further comprises:
- a first portion;
- a second portion recessed from the second plane; and
- an imaginary arc connects the radially outward-most points of the plurality of slits to define a circular boundary;
- a rib extending from a point outside the circular boundary into the circular boundary.

18. A method of assembling a catheter assembly having a catheter hub having a catheter tube extending from a distal end thereof, a needle hub, and a valve located inside the catheter hub for controlling fluid flow, the method comprising:
- positioning a valve inside an interior cavity of the catheter hub, the valve comprising:
  - a first side having a first surface defining a first plane having a first portion and having a second portion on the first side recessed from the first plane;
  - a second side having a second surface opposing the first surface and defining a second plane, the first surface and the second surface defining a thickness of the valve; and
  - a plurality of slits extending from the first side to the second side of the valve at the second portion, the plurality of slits defining a plurality of flaps with each the plurality of slits having an inward-most slit point and a radially outward-most point and wherein an imaginary arc connects the radially outward-most points of the plurality of slits to define a circular boundary;
  - wherein a rib on the first side has an exterior surface located on the first plane and extends from a point outside the circular boundary into the circular boundary; and
  - wherein the first surface defining the first plane extends radially outwardly of the exterior surface of the rib;
- coupling the needle hub, having a needle, with the catheter hub and extending the needle through the catheter tube in a ready to use position.

19. The method according to claim 18, wherein the rib is a first rib and further comprising a second rib and a third rib arranged in a spaced concentric orientation.

20. The method according to claim 19, wherein each of the first, second, and third ribs has an exterior surface that is co-planar with the first plane and extends from a point outside the circular boundary into the circular boundary.

21. The method according to claim 20, wherein the second portion of the first side comprises a first region and a second region and wherein the first region has a recessed planar surface.

22. The method according to claim 18, wherein the valve is disc-shaped and comprises a circumferential region extending axially away from the first surface or the second surface.

23. The method according to claim 18, further comprising placing a valve actuator inside the catheter hub, said valve actuator having an actuator head with a surface for pushing into the valve to deflect the flaps when a surface on a plunger end of the valve actuator is pushed by a connector tip inserted into the catheter hub in a used position.

24. The method according to claim 23, wherein the recessed planar surface of the first region of the second portion defines a diameter that is equal to or less than a maximum diameter of the actuator head of the actuator.

25. The method according to claim 23, wherein each of the first, second, and third ribs has a thickness that equals the thickness of the valve.

26. A catheter assembly comprising:
   a catheter hub having an interior cavity and a catheter tube extending from a distal end thereof;
   a needle hub having a needle extending from a distal end thereof and extending through the catheter hub and the catheter tube in a ready to use position;
   a needle guard located in the catheter hub for covering a needle tip of the needle in a protective position;
   a valve located in the interior cavity of the catheter hub, the valve comprising:
      a first side having a first surface defining a first plane that extends to an outer perimeter of the valve, the first side having a first portion located on the first plane and a second portion that is recessed from the first plane;
      a second side having a second surface opposing the first surface and defining a second plane, the first surface and the second surface defining a thickness of the valve;
      a plurality of slits extending from the first side to the second side of the valve at the second portion, the plurality of slits defining a plurality of flaps with each of the plurality of slits having an inward-most slit point and a radially outward-most point and wherein an imaginary arc connects the radially outward-most points of the plurality of slits to define a circular boundary;
      a rib located inwardly of the outer perimeter of the valve and having an exterior surface that is co-planar with the first plane, the rib extends from a point outside the circular boundary into the circular boundary; and
   a valve opener located in the catheter hub, said valve opener having an actuating head with a surface for deflecting the plurality of flaps when the valve opener is pushed by a connector tip connected to the catheter hub when in a used position.

27. The catheter assembly according to claim 11, wherein the first surface has a circular outer boundary.

28. The catheter assembly according to claim 11, wherein the second portion of the first side comprises a first region and a second region, said first region having a recessed planar surface recessed from said first plane.

29. The catheter assembly according to claim 28, wherein the second region has a sloped surface bridging the first surface defining the first plane and the first region of the second portion.

30. The catheter assembly according to claim 11, wherein the plunger end comprises two plunger elements with each plunger element having a free end.

31. The catheter assembly of claim 11, wherein the first side of the valve is oriented within the catheter hub to face a distal direction.

32. The catheter assembly according to claim 12, wherein the first surface has a circular outer boundary.

33. The catheter assembly according to claim 12, wherein the second portion of the first side comprises a first region and a second region, said first region having a recessed planar surface recessed from said first plane.

34. The catheter assembly according to claim 33, wherein the second region has a sloped surface bridging the first surface defining the first plane and the first region of the second portion.

35. The catheter assembly according to claim 12, wherein the plunger end comprises two plunger elements with each plunger element having a free end.

36. The catheter assembly of claim 12, wherein the first side of the valve is oriented within the catheter hub to face a distal direction.

37. The catheter assembly according to claim 14, wherein the first surface has a circular outer boundary.

38. The catheter assembly according to claim 14, wherein the second portion of the first side comprises a first region and a second region, said first region having a recessed planar surface recessed from said first plane.

39. The catheter assembly according to claim 38, wherein the second region has a sloped surface bridging the first surface defining the first plane and the first region of the second portion.

40. The catheter assembly according to claim 14, wherein the plunger end comprises two plunger elements with each plunger element having a free end.

41. The catheter assembly according to claim 14, wherein the first surface has a circular outer boundary.

42. The catheter assembly according to claim 26, wherein the first side of the valve is oriented within the catheter hub to face a distal direction.

43. The catheter assembly according to claim 26, wherein the first side of the valve is oriented within the catheter hub to face a proximal direction.

44. The catheter assembly according to claim 26, wherein the second region has a sloped surface bridging the first surface defining the first plane and the first region of the second portion.

45. The catheter assembly according to claim 26, wherein the valve opener has a plunger end comprising two plunger elements with each plunger element having a free end.

* * * * *